US006872735B2

(12) United States Patent
Burdick et al.

(10) Patent No.: US 6,872,735 B2
(45) Date of Patent: Mar. 29, 2005

(54) LFA-1 ANTAGONIST COMPOUNDS

(75) Inventors: Daniel J. Burdick, Burlingame, CA (US); Mark S. Stanley, Pacifica, CA (US); David Oare, Belmont, CA (US); Mark E. Reynolds, Millbrae, CA (US); Thomas R. Gadek, Oakland, CA (US); James C. Marsters, Oakland, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 10/618,178

(22) Filed: Jul. 11, 2003

(65) Prior Publication Data

US 2004/0058968 A1 Mar. 25, 2004

Related U.S. Application Data

(63) Continuation of application No. 09/994,546, filed on Nov. 26, 2001, now Pat. No. 6,667,318.
(60) Provisional application No. 60/253,682, filed on Nov. 28, 2000.

(51) Int. Cl.[7] .................. A61K 31/4525; C07D 405/12
(52) U.S. Cl. ...................... 514/326; 546/214; 546/225; 548/200; 548/517; 548/537; 514/330; 514/365; 514/422; 514/423
(58) Field of Search ................... 514/326, 330, 514/365, 422, 423; 546/214, 225; 548/200, 517, 537

(56) References Cited

U.S. PATENT DOCUMENTS 4,665,077 A  5/1987  Stringfellow et al.

FOREIGN PATENT DOCUMENTS

| EP | 0 849 256 A1 | 6/1998 |
|----|--------------|--------|
| WO | WO 97/08133 | 3/1997 |
| WO | WO 98/04247 | 2/1998 |
| WO | WO 99/49856 | 10/1999 |
| WO | WO 00/39081 | 7/2000 |

OTHER PUBLICATIONS

Morris, P., "Therapeutic Strategies in Immunosuppression after Renal Transplantation" *J. Pediatrics* 111:1004–1007 (1987).
U.S. Appl. No. 09/191,927, Burdick, D. et al, filed Nov. 13, 1998.

*Primary Examiner*—Charanjit S. Aulakh
(74) *Attorney, Agent, or Firm*—David W Evans

(57) ABSTRACT

The invention relates to novel compounds having formula (I)

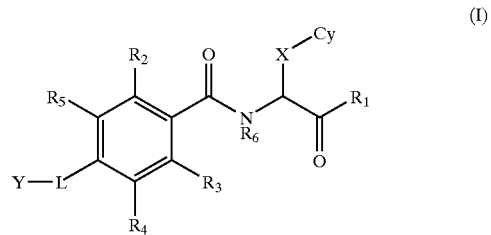

wherein Cy, X, Y, L and $R_{1-6}$ are as defined herein. The compounds bind CD11/CD18 adhesion receptors such as Lymphocyte Function-associated Antigen-1 (LFA-1) and are therefore useful for treating disorders mediated by LFA-1 such as inflammation and autoimmune diseases.

21 Claims, No Drawings

LFA-1 ANTAGONIST COMPOUNDS

This application is a continuation of application Ser. No. 09/994,546 filed on Nov. 26, 2001, issued Dec. 23, 2003 as U.S. Pat. No. 6,667,318, which claims priority to provisional application No. 60/253,682 filed Nov. 28, 2000, the entire disclosures of which are hereby incorporated by reference.

FIELD OF THE INVENTION

The invention relates to novel compounds which bind CD11/CD18 adhesion receptors, in particular Lymphocyte Function-associated Antigen-1 (LFA-1) as well as pharmaceutical compositions containing these compounds which are useful for treating disorders mediated thereby.

BACKGROUND OF THE INVENTION

Inflammation

Human peripheral blood is composed principally of red blood cells, platelets and white blood cells or leukocytes. The family of leukocytes are further classified as neutrophils, lymphocytes (mostly B- and T-cell subtypes), monocytes, eosinophils and basophils. Neutrophils, eosinophils and basophils are sometimes referred to as "granulocytes" or "polymorphonuclear (PMN) granulocytes" because of the appearance of granules in their cytoplasm and their multiple nuclei. Granulocytes and monocytes are often classified as "phagocytes" because of their ability to phagocytose or ingest micro-organisms and foreign mater referred to generally as "antigens". Monocytes are so called because of their large single nucleus and these cells may in turn become macrophages. Phagocytes are important in defending the host against a variety of infections and together with lymphocytes are also involved in inflammatory disorders. The neutrophil is the most common leukocyte found in human peripheral blood followed closely by the lymphocyte. In a microliter of normal human peripheral blood, there are about 6,000 leukocytes, of which about 4,000 are neutrophils, 1500 are lymphocytes, 250 are monocytes, 150 are eosinophils and 25 are basophils.

During an inflammatory response peripheral blood leukocytes are recruited to the site of inflammation or injury by a series of specific cellular interactions (see FIG. 1). The initiation and maintenance of immune functions are regulated by intercellular adhesive interactions as well as signal transduction resulting from interactions between leukocytes and other cells. Leukocyte adhesion to vascular endothelium and migration from the circulation to sites of inflammation is a critical step in the inflammatory response (FIG. 1). T-cell lymphocyte immune recognition requires the interaction of the T-cell receptor with antigen (in combination with the major histocompatibility complex) as well as adhesion receptors, which promote attachment of T-cells to antigen-presenting cells and transduce signals for T-cell activation. The lymphocyte function associated antigen-1 (LFA-1) has been identified as the major integrin that mediates lymphocyte adhesion and activation leading to a normal immune response, as well as several pathological states (Springer, T. A., Nature 346:425–434 (1990)). Intercellular adhesion molecules (ICAM) –1, –2, and –3, members of the immunoglobulin superfamily, are ligands for LFA-1 found on endothelium, leukocytes and other cell types. The binding of LFA-1 to ICAMs mediate a range of lymphocyte functions including lymphokine production of helper T-cells in response to antigen presenting cells, T-lymphocyte mediated target cells lysis, natural killing of tumor cells, and immunoglobulin production through T-cell-B-cell interactions. Thus, many facets of lymphocyte function involve the interaction of the LFA-1 integrin and its ICAM ligands. These LFA-1:ICAM mediated interactions have been directly implicated in numerous inflammatory disease states including; graft rejection, dermatitis, psoriasis, asthma and rheumatoid arthritis.

While LFA-1 (CD11a/CD18) on lymphocytes plays a key role in chronic inflammation and immune responses, other members of the leukocyte integrin family (CD11b/CD18, CD11c/CD18 and CD11d/CD18) also play important roles on other leukocytes, such as granulocytes and monocytes, particularly in early response to infective agents and in acute inflammatory response.

The primary function of polymorphonuclear leukocytes, derived from the neutrophil, eosinophil and basophil lineage, is to sense inflammatory stimuli and to emigrate across the endothelial barrier and carry out scavenger function as a first line of host defense. The integrin Mac-1 (CD11b/CD18) is rapidly upregulated on these cells upon activation and binding to its multiple ligands which results in the release of oxygen derived free radicals, protease's and phospholipases. In certain chronic inflammatory states this recruitment is improperly regulated resulting in significant cellular and tissue injury. (Harlan, J. M., *Acta Med Scand Suppl.*, 715:123 (1987); Weiss, S., *New England J. of Med.*, 320:365 (1989)).

LFA-1 (CD11a/CD18) and Mac-1 (CD11b/CD18)

The (CD11/CD18) family of adhesion receptor molecules comprises four highly related cell surface glycoproteins; LFA-1 (CD11a/CD18), Mac-1 (CD11b/CD18), p150.95 (CD11c/CD18) and (CD11d/CD18). LFA-1 is present on the surface of all mature leukocytes except a subset of macrophages and is considered the major lymphoid integrin. The expression of Mac-1, p150.95 and CD11d/CD18 is predominantly confined to cells of the myeloid lineage (which include neutrophils, monocytes, macrophage and mast cells). Functional studies have suggested that LFA-1 interacts with several ligands, including ICAM-1 (Rothleinet al., *J. Immunol.* 137:1270–1274 (1986), ICAM-2, (Staunton et al., *Nature* 339:361–364 (1989)), ICAM-3 (Fawcett et al., *Nature* 360:481–484 (1992); Vezeux et al., *Nature* 360:485–488, (1992); de Fougerolles and Springer, *J. Exp. Med.* 175:185–190 (1990)) and Telencephalin (Tian et al., *J. Immunol.* 158:928–936 (1997)).

The CD11/CD18 family is related structurally and genetically to the larger integrin family of receptors that modulate cell adhesive interactions, which include; embryogenesis, adhesion to extracellular substrates, and cell differentiation (Hynes, R. O., *Cell* 48:549–554 (1987); Kishimotoet al., *Adv. Immunol.* 46:149–182 (1989); Kishimotoet al., *Cell* 48:681–690 (1987); Ruoslahtiet al., *Science* 238:491–497 (1987).

Integrins are a class of membrane-spanning heterodimers comprising an α subunit in noncovalent association with a β subunit. The β subunits are generally capable of association with more than one α subunit and the heterodimers sharing a common β subunit have been classified as subfamilies within the integrin population (Larson and Springer, "Structure and function of leukocyte integrins," *Immunol. Rev.* 114:181–217 (1990)).

The integrin molecules of the CD11/CD18 family, and their cellular ligands, have been found to mediate a variety of cell-cell interactions, especially in inflammation. These proteins have been demonstrated to be critical for adhesive functions in the immune system (Kishimotoet al., *Adv. Immunol.* 46:149–182 (1989)). Monoclonal antibodies to LFA-1 have been shown to block leukocyte adhesion to endothelial cells (Dustin et al., *J. Cell. Biol.* 107:321–331

(1988); Smith et al., *J. Clin. Invest.* 83:2008–2017 (1989)) and to inhibit T-cell activation (Kuypers et al., *Res. Immunol.*, 140:461 (1989)), conjugate formation required for antigen-specific CTL killing (Kishimotoet al., *Adv. Immunol.* 46:149–182 (1989)), T. cell proliferation (Davignonet al., *J. Immunol.* 127:590–595 (1981)) and NK cell killing (Krenskyet al., *J. Immunol.* 131:611–616 (1983)).

ICAMs

ICAM-1 (CD54) is a cell surface adhesion receptor that is a member of the immunoglobulin protein super-family (Rothleinet al., *J. Immunol.* 137:1270–1274 (1986); Stauntonet al., *Cell* 52:925–933 (1988). Members of this super-family are characterized by the presence of one or more Ig homology regions, each consisting of a disulfide-bridged loop that has a number of anti-parallel β-pleated strands arranged in two sheets. Three types of homology regions have been identified, each with a typical length and having a consensus sequence of amino acid residues located between the cysteines of the disulfide bond (Williams, A. F. et al. *Ann Rev. Immunol.* 6:381–405 (1988); Hunkapillar, T. et al. *Adv. Immunol.* 44:1–63 (1989). ICAM-1 is expressed on a variety of hematopoietic and non-hematopoietic cells and is upregulated at sites of inflammation by a variety of inflammatory mediators (Dustin et al., *J. Immunol.*, 137:256–254 (1986)). ICAM-1 is a 90,000–110,000 $M_r$ glycoprotein with a low messenger RNA levels and moderate surface expression on unstimulated endothelial cells. LPS, IL-1 and TNF strongly upregulate ICAM-1 mRNA and surface expression with peak expression at approximately 18–24 hours (Dustinet al., *J. Cell. Biol.* 107:321–331 (1988); Stauntonet al., *Cell* 52:925–933 (1988)). ICAM-1 has five extracellular Ig like domains (designated Domains 1, 2, 3, 4 and 5 or D1, D2, D3, D4 and D5) and an intracellular or cytoplasmic domain. The structures and sequence of the domains is described by Staunton et al. (*Cell* 52:925–933 (1988)).

ICAM-1 was defined originally as a counter-receptor for LFA-1 (Springer et al., *Ann. Rev. Immunol*, 5:223–252 (1987); Marlin *Cell* 51:813–819 (1987); Simmonset al., *Nature* 331:624–627 (1988); Staunton *Nature* 339:61–64 (1989); Stauntonet al., *Cell* 52:925–933 (1988)). The LFA-1/ICAM-1 interaction is known to be at least partially responsible for lymphocyte adhesion (Dustinet al., *J. Cell. Biol.* 107:321–331 (1988); Mentzeret al., *J. Cell. Physiol.* 126:285–290 (1986)), monocyte adhesion (Amaoutet al., *J. Cell Physiol.* 137:305 (1988); Mentzeret al., *J. Cell. Physiol.* 130:410–415 (1987); te Veldeet al., *Immunology* 61:261–267 (1987)), and neutrophil adhesion (Loet al., *J. Immunol.* 143(10):3325–3329 (1989); Smith et al., *J. Clin. Invest.* 83:2008–2017 (1989)) to endothelial cells. Through the development of function blocking monoclonal antibodies to ICAM-1 additional ligands for LFA-1 were identified, ICAM-2 and ICAM-3 (Simmons, *Cancer Surveys* 24, Cell Adhesion and Cancer, 1995) that mediate the adhesion of lymphocytes to other leukocytes as well as non-hematopoietic cells. Interactions of LFA-1 with ICAM-2 are thought to mediate natural killer cell activity (Helander et al., *Nature* 382:265–267 (1996)) and ICAM-3 binding is thought to play a role in lymphocyte activation and the initiation of the immune response (Simmons, ibid). The precise role of these ligands in normal and aberrant immune responses remains to be defined.

Disorders Mediated by T Lymphocytes

Function blocking monoclonal antibodies have shown that LFA-1 is important in T-lymphocyte-mediated killing, T-helper lymphocyte responses, natural killing, and antibody-dependent killing (Springer et al., *Ann. Rev. Immunol* 5:223–252 (1987)). Adhesion to the target cell as well as activation and signaling are steps that are blocked by antibodies against LFA-1.

Many disorders and diseases are mediated through T lymphocytes and treatment of these diseases have been addressed through many routes. Rheumatoid arthritis (RA) is one such disorder. Current therapy for RA includes bed rest, application of heat, and drugs. Salicylate is the currently preferred treatment drug, particularly as other alternatives such as immunosuppressive agents and adrenocorticosteroids can cause greater morbidity than the underlying disease itself. Nonsteroidal anti-inflammatory drugs are available, and many of them have effective analgesic, antipyretic and anti-inflammatory activity in RA patients. These include cyclosporin, indomethacin, phenylbutazone, phenylacetic acid derivatives such as ibuprofen and fenoprofen, naphthalene acetic acids (naproxen), pyrrolealkanoic acid (tometin), indoleacetic acids (sulindac), halogenated anthranilic acid (meclofenamate sodium), piroxicam, and diflunisal. Other drugs for use in RA include anti-malarials such as chloroquine, gold salts and penicillamine. These alternatives frequently produce severe side effects, including retinal lesions and kidney and bone marrow toxicity. Immunosuppressive agents such as methotrexate have been used only in the treatment of severe and unremitting RA because of their toxicity. Corticosteroids also are responsible for undesirable side effects (e.g., cataracts, osteoporosis, and Cushing's disease syndrome) and are not well tolerated in many RA patients.

Another disorder mediated by T lymphocytes is host rejection of grafts after transplantation. Attempts to prolong the survival of transplanted allografts and xenografts, or to prevent host versus graft rejection, both in experimental models and in medical practice, have centered mainly on the suppression of the immune apparatus of the host/recipient. This treatment has as its aim preventive immunosuppression and/or treatment of graft rejection. Examples of agents used for preventive immunosuppression include cytotoxic drugs, anti-metabolites, corticosteroids, and anti-lymphocytic serum. Nonspecific immunosuppressive agents found particularly effective in preventive immunosuppression (azathioprine, bromocryptine, methylprednisolone, prednisone, and most recently, cyclosporin A) have significantly improved the clinical success of transplantation. The nephrotoxicity of cyclosporin A after renal transplantation has been reduced by co-administration of steroids such as prednisolone, or prednisolone in conjunction with azathioprine. In addition, kidneys have been grafted successfully using anti-lymphocyte globulin followed by cyclosporin A. Another protocol being evaluated is total lymphoid irradiation of the recipient prior to transplantation followed by minimal immunosuppression after transplantation.

Treatment of rejection has involved use of steroids, 2-amino-6-aryl-5-substituted pyrimidines, heterologous anti-lymphocyte globulin, and monoclonal antibodies to various leukocyte populations, including OKT-3. See generally *J. Pediatrics*, 111: 1004–1007 (1987), and specifically U.S. Pat. No. 4,665,077.

The principal complication of immunosuppressive drugs is infections. Additionally, systemic immunosuppression is accompanied by undesirable toxic effects (e.g., nephrotoxicity when cyclosporin A is used after renal transplantation) and reduction in the level of the hemopoietic stem cells. Immunosuppressive drugs may also lead to obesity, poor wound healing, steroid hyperglycemia, steroid psychosis, leukopenia, gastrointestinal bleeding, lymphoma, and hypertension.

In view of these complications, transplantation immunologists have sought methods for suppressing immune responsiveness in an antigen-specific manner (so that only the response to the donor alloantigen would be lost). In addition, physicians specializing in autoimmune disease strive for methods to suppress autoimmune responsiveness so that only the response to the self-antigen is lost. Such specific immunosuppression generally has been achieved by modifying either the antigenicity of the tissue to be grafted or the specific cells capable of mediating rejection. In certain instances, whether immunity or tolerance will be induced depends on the manner in which the antigen is presented to the immune system.

Pretreating the allograft tissues by growth in tissue culture before transplantation has been found in two murine model systems to lead to permanent acceptance across MHC barriers. Lafferty et al., *Transplantation*, 22:138–149 (1976); Bowen et al., *Lancet*, 2:585–586 (1979). It has been hypothesized that such treatment results in the depletion of passenger lymphoid cells and thus the absence of a stimulator cell population necessary for tissue immunogenicity. Lafferty et al., *Annu. Rev. Immunol.*, 1:143 (1983). See also Lafferty et al., *Science*, 188:259–261 (1975) (thyroid held in organ culture), and Gores et al., *J. Immunol.*, 137:1482–1485 (1986) and Faustman et al., *Proc. Natl. Acad. Sci. U.S.A.*, 78: 5156–5159 (1981) (islet cells treated with murine anti-Ia antisera and complement before transplantation). Also, thyroids taken from donor animals pretreated with lymphocytotoxic drugs and gamma radiation and cultured for ten days in vitro were not rejected by any normal allogeneic recipient (Gose and Bach, *J. Exp. Med.*, 149:1254–1259 (1979)). All of these techniques involve depletion or removal of donor lymphocyte cells.

In some models such as vascular and kidney grafts, there exists a correlation between Class II matching and prolonged allograft survival, a correlation not present in skin grafts (Pescovitz et al., *J. Exp. Med.*, 160:1495–1508 (1984); Conti et al., *Transplant. Proc.*, 19: 652–654 (1987)). Therefore, donor-recipient HLA matching has been utilized. Additionally, blood transfusions prior to transplantation have been found to be effective (Opelz et al., *Transplant. Proc.*, 4: 253 (1973); Persijn et al., *Transplant. Proc.*, 23:396 (1979)). The combination of blood transfusion before transplantation, donor-recipient HLA matching, and immunosuppression therapy (cyclosporin A) after transplantation was found to improve significantly the rate of graft survival, and the effects were found to be additive (Opelz et al., *Transplant. Proc.*, 17:2179 (1985)).

The transplantation response may also be modified by antibodies directed at immune receptors for MHC antigens (Bluestone et al., *Immunol. Rev.* 90:5–27 (1986)). Further, graft survival can be prolonged in the presence of antigraft antibodies, which lead to a host reaction that in turn produces specific immunosuppression (Lancaster et al., *Nature*, 315: 336–337 (1985)). The immune response of the host to MHC antigens may be modified specifically by using bone marrow transplantation as a preparative procedure for organ grafting. Thus, anti-T-cell monoclonal antibodies are used to deplete mature T-cells from the donor marrow inoculum to allow bone marrow transplantation without incurring graft-versus-host disease (Mueller-Ruchholtz et al., *Transplant Proc.*, 8:537–541 (1976)). In addition, elements of the host's lymphoid cells that remain for bone marrow transplantation solve the problem of immunoincompetence occurring when fully allogeneic transplants are used.

As shown in FIG. 1, lymphocyte adherence to endothelium is a key event in the process of inflammation. There are at least three known pathways of lymphocyte adherence to endothelium, depending on the activation state of the T-cell and the endothelial cell. T-cell immune recognition requires the contribution of the T-cell receptor as well as adhesion receptors, which promote attachment of—cells to antigen-presenting cells and transduce regulatory signals for T-cell activation. The lymphocyte function associated (LFA) antigen-1 (LFA-1, CD11a/CD18, $\alpha_L\beta_2$: where $\alpha_L$ is CD11a and $\beta_2$ is CD18) has been identified as the major integrin receptor on lymphocytes involved in these cell adherence interactions leading to several pathological states. ICAM-1, the endothelial cell immunoglobulin-like adhesion molecule, is a known ligand for LFA-1 and is implicated directly in graft rejection, psoriasis, and arthritis.

LFA-1 is required for a range of leukocyte functions, including lymphokine production of helper T-cells in response to antigen-presenting cells, killer T-cell-mediated target cell lysis, and immunoglobulin production through T-cell/B-cell interactions. Activation of antigen receptors on T-cells and B-cells allows LFA-1 to bind its ligand with higher affinity.

Monoclonal antibodies (MAbs) directed against LFA-1 led to the initial identification and investigation of the function of LFA-1 (Davignon et al., *J. Immunol.*, 127:590 (1981)). LFA-1 is present only on leukocytes (Krenskey et al., *J. Immunol.*, 131:611 (1983)), and ICAM-1 is distributed on activated leukocytes, dermal fibroblasts, and endothelium (Dustin et al., *J. Immunol.* 137:245 (1986)).

Previous studies have investigated the effects of anti-CD11a MAbs on many T-cell-dependent immune functions in vitro and a limited number of immune responses in vivo. In vitro, anti-CD11a MAbs inhibit T-cell activation (Kuypers et al., *Res. Immunol.*, 140:461 (1989)), T-cell-dependent B-cell proliferation and differentiation (Davignon et al., supra; Fischer et al., *J. Immunol.*, 136:3198 (1986)), target cell lysis by cytotoxic T-lymphocytes (Krensky et al., supra), formation of immune conjugates (Sanders et al., *J. Immunol.*, 137:2395 (1986); Mentzer et al., *J. Immunol.*, 135:9 (1985)), and the adhesion of T-cells to vascular endothelium (Lo et al., *J. Immunol.*, 143:3325 (1989)). Also, the antibody 5C6 directed against CD11b/CD18 was found to prevent intra-islet infiltration by both macrophages and T cells and to inhibit development of insulin-dependent diabetes mellitis in mice (Hutchings et al., *Nature*, 348: 639 (1990)).

The observation that LFA-1:ICAM-1 interaction is necessary to optimize T-cell function in vitro, and that anti-CD11a MAbs induce tolerance to protein antigens (Benjamin et al., *Eur. J. Immunol.*, 18:1079 (1988)) and prolongs tumor graft survival in mice (Heagy et al., *Transplantation*, 37: 520–523 (1984)) was the basis for testing the MAbs to these molecules for prevention of graft rejection in humans.

Experiments have also been carried out in primates. For example, based on experiments in monkeys it has been suggested that a MAb directed against ICAM-1 can prevent or even reverse kidney graft rejection (Cosimi et al., "Immunosuppression of Cynomolgus Recipients of Renal Allografts by R6.5, a Monoclonal Antibody to Intercellular Adhesion Molecule-1," in Springer et al. (eds.), *Leukocyte Adhesion Molecules* New York: Springer, (1988), p. 274; Cosimi et al., *J. Immunology*, 144:4604–4612 (1990)). Furthermore, the in vivo administration of anti-CD11a MAb to cynomolgus monkeys prolonged skin allograft survival (Berlin et al., *Transplantation*, 53: 840–849 (1992)).

The first successful use of a rat anti-murine CD11a antibody (25-3; IgG1) in children with inherited disease to prevent the rejection of bone-marrow-mismatched haploidentical grafts was reported by Fischer et al., *Lancet*, 2: 1058 (1986). Minimal side effects were observed. See also Fischer et al., *Blood*, 77: 249 (1991); van Dijken et al., *Transplantation*, 49:882 (1990); and Perez et al., *Bone Marrow Transplantation*, 4:379 (1989). Furthermore, the antibody 25-3 was effective in controlling steroid-resistant acute graft-versus-host disease in humans (Stoppa et al., *Transplant. Int.*, 4:3–7 (1991)).

However, these results were not reproducible in leukemic adult grafting with this MAb (Maraninchi et al., *Bone Marrow Transplant*, 4:147–150 (1989)), or with an anti-CD18 MAb, directed against the invariant chain of LFA-1, in another pilot study (Baume et al., *Transplantation*, 47: 472 (1989)). Furthermore, a rat anti-murine CD11a MAb, 25-3, was unable to control the course of acute rejection in human kidney transplantation (LeMauff et al., *Transplantation*, 52: 291 (1991)).

A review of the use of monoclonal antibodies in human transplantation is provided by Dantal and Soulillou, *Current Opinion in Immunology*, 3:740–747 (1991). An earlier report showed that brief treatment with either anti-LFA-1 or anti-ICAM-1 MAbs minimally prolonged the survival of primarily vascularized heterotopic heart allografts in mice (Isobe et al., *Science*, 255:1125 (1992)). However, combined treatment with both MAbs was required to achieve long-term graft survival in this model.

Independently, it was shown that treatment with anti-LFA-1 MAb alone potently and effectively prolongs the survival of heterotopic (ear-pinnae) nonprimarily vascularized mouse heart grafts using a maximum dose of 4 mg/kg/day and treatment once a week after a daily dose (Nakakura et al., *J. Heart Lung Transplant.*, 11:223 (1992)). Nonprimarily vascularized heart allografts are more immunogenic and more resistant to prolongation of survival by MAbs than primarily vascularized heart allografts (Warren et al., *Transplant. Proc.*, 5:717 (1973); Trager et al., *Transplantation*, 47:587 (1989)). The latter reference discusses treatment with L3T4 antibodies using a high initial dose and a lower subsequent dose.

Another study on treating a sclerosis-type disease in rodents using similar antibodies to those used by Nakakura et al., supra, is reported by Yednock et al., *Nature*, 356:63–66 (1992). Additional disclosures on the use of anti-LFA-1 antibodies and ICAM-1, ICAM-2, and ICAM-3 and their antibodies to treat LFA-1-mediated disorders include WO 91/18011 published Nov. 28, 1991, WO 91/16928 published Nov. 14, 1991, WO 91/16927 published Nov. 14, 1991, Can. Pat. Appln. 2,008,368 published Jun. 13, 1991, WO 90/03400, WO 90/15076 published Dec. 13, 1990, WO 90/10652 published Sep. 20, 1990, EP 387,668 published Sep. 19, 1990, WO 90/08187 published Jul. 26, 1990, WO 90/13281, WO 90/13316, WO 90/13281, WO 93/06864, WO 93/21953, WO 93/13210, WO 94/11400, EP 379,904 published Aug. 1, 1990, EP 346,078 published Dec. 13, 1989, U.S. Pat. No. 5,002,869, U.S. Pat. No. 5,071,964, U.S. Pat. No. 5,209,928, U.S. Pat. No. 5,223,396, U.S. Pat. No. 5,235,049, U.S. Pat. No. 5,284,931, U.S. Pat. No. 5,288,854, U.S. Pat. No. 5,354,659, Australian Pat. Appln. 15518/88 published Nov. 10, 1988, EP 289,949 published Nov. 9, 1988, and EP 303,692 published Feb. 22, 1989, EP 365,837, EP 314,863, EP 319,815, EP 468, 257, EP 362,526, EP 362, 531, EP 438,310.

Other disclosures on the use of LFA-1 and ICAM peptide fragments and antagonists include; U.S. Pat. No. 5,149,780, U.S. Pat. No. 5,288,854, U.S. Pat. No. 5,340,800, U.S. Pat. No. 5,424,399, U.S. Pat. No. 5,470,953, WO 90/03400, WO 90/13316, WO 90/10652, WO 91/19511, WO 92/03473, WO 94/11400, WO 95/28170, JP 4193895, EP 314,863, EP 362,526 and EP 362,531.

The above methods successfully utilizing anti-LFA-1 or anti-ICAM-1 antibodies, LFA-1 or ICAM-1 peptides, fragments or peptide antagonists represent an improvement over traditional immunosuppressive drug therapy. These studies demonstrate that LFA-1 and ICAM-1 are appropriate targets for antagonism. There is a need in the art to better treat disorders that are mediated by LFA-1 including autoimmune diseases, graft vs. host or host vs. graft rejection, and T-cell inflammatory responses, so as to minimize side effects and sustain specific tolerance to self- or xenoantigens. There is also a need in the art to provide a non-peptide antagonists to the LFA-1:ICAM-1 interaction.

Albumin is an abundant plasma protein which is responsible for the transport of fatty acids. However, albumin also binds and perturbs the pharmacokinetics of a wide range of drug compounds. Accordingly, a significant factor in the pharmacological profile of any drug is its binding characteristics with respect to serum plasma proteins such as albumin. A drug compound may have such great affinity for plasma proteins that it is not be available in serum to interact with its target tissue, cell or protein. For example, a compound for which 99% binds to plasma protein upon administration will have half the concentration available in plasma to interact with its target than a compound which binds only 98%. Accordingly it would be desirable to provide LFA antagonist compounds which have low serum plasma protein binding affinity.

SUMMARY OF THE INVENTION

In an aspect of the present invention, there is provided novel compounds of formula (I)

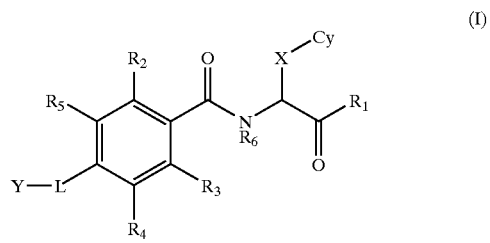

wherein
Cy is a non-aromatic carbocycle or heterocycle optionally substituted with hydroxyl, mercapto, thioalkyl, halogen, oxo, thio, amino, aminoalkyl, amidine, guanidine, nitro, alkyl, alkoxy or acyl;
X is a divalent hydrocarbon chain optionally substituted with hydroxyl, mercapto, halogen, amino, aminoalkyl, nitro, oxo or thio and optionally interrupted with N, O, S, SO or $SO_2$;
Y is a carbocycle or heterocycle optionally substituted with hydroxyl, mercapto, halogen, oxo, thio, a hydrocarbon, a halo-substituted hydrocarbon, amino, amidine, guanidine, cyano, nitro, alkoxy or acyl;
L is a bond or a divalent hydrocarbon optionally having one or more carbon atoms replaced with N, O, S, SO or $SO_2$ and optionally being substituted with hydroxyl, halogen oxo or thio; or three carbon atoms of the hydrocarbon are replaced with an amino acid residue;
$R_1$ is H, OH, amino, O-carbocycle or alkoxy optionally substituted with amino, a carbocycle or a heterocycle;
$R_{2-5}$ are independently H, hydroxyl, mercapto, halogen, cyano, amino, amidine, guanidine, nitro or alkoxy; or R₃ and R₄ together form a fused carbocycle or heterocycle optionally substituted with hydroxyl, halogen, oxo, thio, amino, amidine, guanidine or alkoxy;

R₆ is H or a hydrocarbon chain optionally substituted with a carbocycle or a heterocycle; and salts, solvates and hydrates thereof;

with the proviso that when Y is phenyl, R₂, R₄ and R₅ are H, R₃ is Cl and R₁ is OH then X is other than cyclohexyl.

In another aspect of the invention, there is provided pharmaceutical compositions comprising a compound of the invention and a pharmaceutically acceptable carrier.

In another aspect of the invention, there is provided a method of treating a disease or condition mediated by LFA-1 in a mammal comprising administering to said mammal an effective amount of a compound of the invention.

DETAILED DESCRIPTION OF THE INVENTION

The invention provides novel compounds of formula (I)

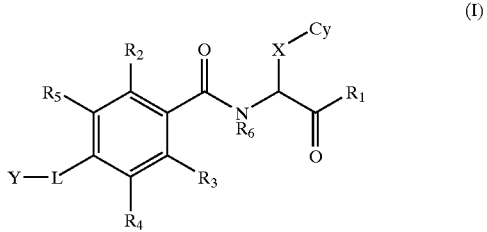

(I)

wherein Cy, X, Y, L and R₁₋₆ are as defined herein. Compounds of the invention exhibit reduced plasma protein binding affinity by virtue of a non-aromatic ring at substituent Cy in comparison to those having an aromatic ring at this portion of the molecule.

The term "non-aromatic" refers to carbocycle or heterocycle rings that do not have the properties which define aromaticity. For aromaticity, a ring must be planar, have p-orbitals that are perpendicular to the plane of the ring at each ring atom and satisfy the Huckel rule where the number of pi electrons in the ring is (4n+2) wherein n is an integer (i.e. the number of pi electrons is 2, 6, 10 or 14). Non-aromatic rings provided herein do not satisfy one or all of these criteria for aromaticity.

The term "alkoxy" as used herein includes saturated, i.e. O-alkyl, and unsaturated, i.e. O-alkenyl and O-alkynyl, group. Exemplary alkoxy groups include methoxy, ethoxy, propoxy, butoxy, i-butoxy, s-butoxy, t-butoxy, pentyloxy and hexyloxy.

The term "amino" refers to a primary (—NH₂), secondary —(NHR), tertiary (—N(R)₂) or quaternary (—N⁺(R)₄) amine wherein R is a hydrocarbon chain, hydroxy, a carbocycle, a heterocycle or a hydrocarbon chain substituted with a carbocycle or heterocycle.

The term "amino acid" refers to naturally and non-naturally occurring α-(alpha), β-(beta), D- and L-amino acid residues. Non-natural amino acids include those having side chains other than those occurring in nature.

By "carboxyl" is meant herein to be a free acid —COOH as well as esters thereof such as alkyl, aryl and aralkyl esters. Preferred esters are methyl, ethyl, propyl, butyl, i-butyl, s-butyl and t-butyl esters.

The term "carbocycle" refers to a mono-, bi- or tri-cyclic carbon ring or ring system having 4–16 members (including bridged) which is saturated, unsaturated or partially unsaturated including aromatic (aryl) ring systems (unless specified as non-aromatic). Preferred non-aromatic carbocyclic rings include cyclopropyl, cyclopropenyl, cyclobutyl, cyclobutenyl, cyclopentyl, cyclopentenyl, cyclohexyl and cyclohexenyl. Preferred aromatic carbocyclic rings include phenyl and naphthyl.

The term "heterocycle" refers to a mono-, bi- or tri-cyclic ring system having 5–16 members wherein at least one ring atom is a heteroatom (i.e. N, O and S as well as SO, or SO₂). The ring system is saturated, unsaturated or partially unsaturated and may be aromatic (unless specified as non-aromatic). Exemplary heterocycles include piperidine, piperazine, pyridine, pyrazine, pyrimidine, pyridazine, morpholine, pyran, pyrole, furan, thiophene (thienyl), imidazole, pyrazole, thiazole, isothiazole, dithiazole, oxazole, isoxazole, dioxazole, thiadiazole, oxadiazole, tetrazole, triazole, thiatriazole, oxatriazole, thiadiazole, oxadiazole, purine and benzofused derivatives thereof.

The term "hydrocarbon chain" refers to saturated, unsaturated, linear or branched carbon chains i.e. alkyl, alkenyl and alkynyl. Preferred hydrocarbon chains incorporate 1–12 carbon atoms, more preferably 1–6 and most preferably 1–4 carbon atoms i.e. methyl, ethyl, propyl, butyl and allyl.

The phrase "optionally substituted with" is understood to mean, unless otherwise stated, that one or more of the specified substituents is covalently attached to the substituted moiety. When more than one, the substituents may be the same or different group.

Cy is a non-aromatic carbocycle or heterocycle optionally substituted with hydroxyl (—OH), mercapto (—SH), thioalkyl, halogen (e.g. F, Cl, Br, I), oxo (═O), thio (═S), amino, aminoalkyl, amidine (—C(NH)—NH₂), guanidine (—NH₂—C(NH)—NH₂), nitro, alkyl or alkoxy. In a particular embodiment, Cy is a 3–5 member ring. In a preferred embodiment, Cy is a 5- or 6-member non-aromatic heterocycle optionally substituted with hydroxyl, mercapto, halogen (preferably F or Cl), oxo (═O), thio (═S), amino, amidine, guanidine, nitro, alkyl or alkoxy. In a more preferred embodiment, Cy is a 5-member non-aromatic heterocycle optionally substituted with hydroxyl, oxo, thio, Cl, C₁₋₄ alkyl (preferably methyl), or C₁₋₄ alkanoyl (preferably acetyl, propanoyl or butanoyl). More preferably the non-aromatic heterocycle comprises one or heteroatoms (N, O or S) and is optionally substituted with hydroxyl, oxo, mercapto, thio, methyl, acetyl, propanoyl or butyl. In particular embodiments the non-aromatic heterocycle comprises at least one nitrogen atom that is optionally substituted with methyl or acetyl. In a particularly preferred embodiment, the non-aromatic heterocycle is selected from the group consisting of piperidine, piperazine, morpholine, tetrahydrofuran, tetrahydrothiophene, oxazolidine, thiazolidine optionally substituted with hydroxy, oxo, mercapto, thio, alkyl or alkanoyl. In a most preferred embodiment Cy is a non-aromatic heterocycle selected from the group consisting of tetrahydrofuran-2-yl, thiazolidin-5-yl, thiazolidin-2-one-5-yl, and thiazolidin-2-thione-5-yl and cyclopropapyrrolidine.

In another preferred embodiment Cy is a 3–6 member carbocycle optionally substituted with hydroxyl, mercapto, halogen, oxo, thio, amino, amidine, guanidine, alkyl, alkoxy or acyl. In a particular embodiment the carbocycle is saturated or partially unsaturated. In particular embodiments Cy is a carbocycle selected from the group consisting of cyclopropyl, cyclopropenyl, cyclobutyl, cyclobutenyl, cyclopentyl, cyclopentenyl, cyclohexyl and cyclohexenyl.

X is a C₁₋₅ divalent hydrocarbon linker optionally having one or more carbon atoms replaced with N, O, S, SO or SO₂ and optionally being substituted with hydroxyl, mercapto, halogen, amino, aminoalkyl, nitro, oxo or thio. In a preferred embodiment X will have at least one carbon atom. Replacements and substitutions may form an amide moiety (—NRC(O)— or —C(O)NR—) within the hydrocarbon chain or at either or both ends. Other moieties include sulfonamide (—NRSO$_2$— or —SO$_2$NR), acyl, ether, thioether and amine. In a particularly preferred embodiment X is the group —CH$_2$—NR$_6$—C(O)— wherein the carbonyl —C(O)-portion thereof is adjacent (i.e. covalently bound) to Cy and R$_6$ is alkyl i.e. methyl and more preferably H.

Y is a carbocycle or heterocycle optionally substituted with hydroxyl, mercapto, halogen, oxo, thio, a hydrocarbon, a halo-substituted hydrocarbon, amino, amidine, guanidine, cyano, nitro, alkoxy or acyl. In particular embodiment, Y is aryl or heteroaryl optionally substituted with halogen or hydroxyl. In a particularly preferred embodiment, Y is phenyl, furan-2-yl, thiophene-2-yl, phenyl substituted with a halogen (preferably Cl) or hydroxyl, preferably at the meta position.

L is a divalent hydrocarbon optionally having one or more carbon atoms replaced with N, O, S, SO or SO$_2$ and optionally being substituted with hydroxyl, halogen oxo, or thio; or three carbon atoms of the hydrocarbon are replaced with an amino acid residue. Preferably L is less than 10 atoms in length and more preferably 5 or less and most preferably 5 or 3 atoms in length. In particular embodiments, L is selected from the group consisting of —CH=CH—C(O)—NR$_6$—CH$_2$—, —CH$_2$—NR$_6$—C(O)—, —C(O)—NR$_6$—CH$_2$—, —CH(OH)—(CH$_2$)$_2$—, —(CH$_2$)$_2$—CH(OH)—, —(CH$_2$)$_3$—, —C(O)—NR$_6$—CH(R$_7$)—C(O)—NR$_6$—, —NR$_6$—C(O)—CH(R$_7$)—NR$_6$—C(O)—, —CH(OH)—CH$_2$—O— and —CH(OH)—CF$_2$—CH$_2$— wherein each R$_6$ is independently H or alkyl and R$_7$ is an amino acid side chain. Preferred amino acid side chains include non-naturally occurring side chains such as phenyl or naturally occurring side chains. Preferred side chains are those from Phe, Tyr, Ala, Gln and Asn. In a preferred embodiments L is —CH=CH—C(O)—NR$_6$—CH$_2$— wherein the —CH=CH— moiety thereof is adjacent (i.e. covalently bound) to Y. In another preferred embodiment, L is —CH$_2$—NR$_6$—C(O)— wherein the methylene moiety (—CH$_2$—) thereof is adjacent to Y.

R$_1$ is H, OH, amino, O-carbocycle or alkoxy optionally substituted with amino, a carbocycle or a heterocycle. In a preferred embodiment, R$_1$ is H, phenyl or C$_{1-4}$ alkoxy optionally substituted with a carbocycle such as phenyl. In a particular embodiment R$_1$ is H. In another particular embodiment R$_1$ is methoxy, ethoxy, propyloxy, butyloxy, isobutyloxy, s-butyloxy, t-butyloxy, phenoxy or benzyloxy. In yet another particular embodiment R$_1$ is NH$_2$. In a particularly preferred embodiment R$_1$ is ethoxy. In another particularly preferred embodiment R$_1$ is isobutyloxy. In another particularly preferred embodiment R$_1$ is alkoxy substituted with amino, for example 2-aminoethoxy, N-morpholinoethoxy, N,N-dialkyaminoethoxy, quaternary ammonium hydroxy alkoxy (e.g. trimethylammoniumhydroxyethoxy).

R$_{2-5}$ are independently H, hydroxyl, mercapto, halogen, cyano, amino, amidine, guanidine, nitro or alkoxy; or R$_3$ and R$_4$ together form a fused carbocycle or heterocycle optionally substituted with hydroxyl, halogen, oxo, thio, amino, amidine, guanidine or alkoxy. In a particular embodiment R$_2$ and R$_3$ are independently H, F, Cl, Br or I. In another particular embodiment, R$_4$ and R$_5$ are both H. In another particular embodiment, one of R$_2$ and R$_3$ is a halogen while the other is hydrogen or a halogen. In a particularly preferred embodiment, R$_3$ is Cl while R$_2$, R$_4$ and R$_5$ are each H. In another particularly preferred embodiment, R$_2$ and R$_3$ are both Cl while R$_4$ and R$_5$ are both H.

R$_6$ is H or a hydrocarbon chain optionally substituted with a carbocycle or a heterocycle. In a preferred embodiment, R$_6$ is H or alkyl i.e. methyl, ethyl, propyl, butyl, i-butyl, s-butyl or t-butyl. In a particular embodiment R$_6$ is H.

In a preferred embodiment, compounds of the invention have the general formula (Ia)–(If)

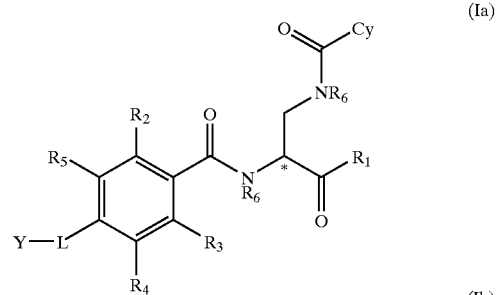
(Ia)

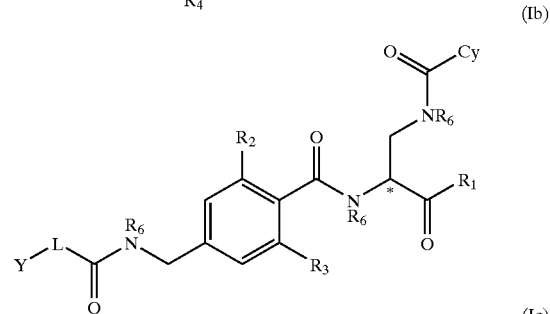
(Ib)

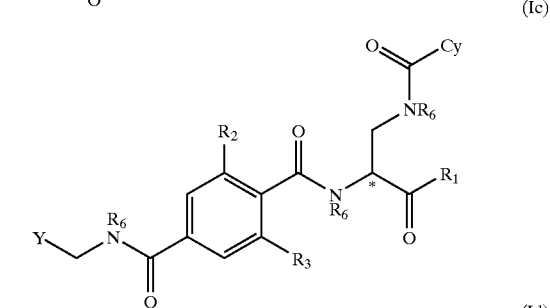
(Ic)

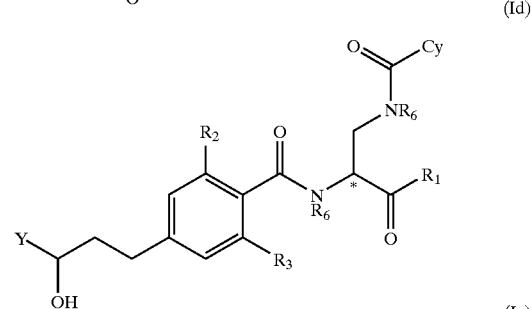
(Id)

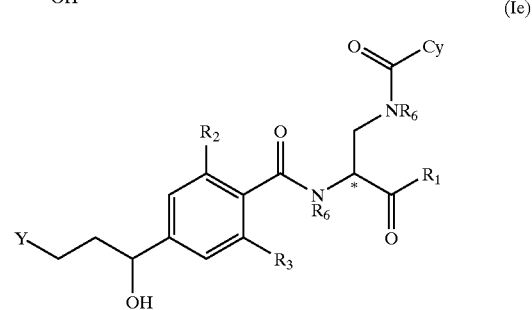
(Ie)

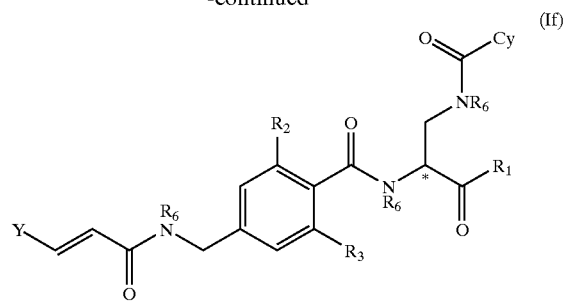
wherein Cy, Y, L and $R_{1-6}$ are as previously defined. In a particularly preferred embodiment, the carbon atom marked with an asterisk (*) in compounds of formula (Ia)–(If) is chiral. In a particular embodiment, the carbon atom has an R-configuration. In another particular embodiment, the carbon atom has an S-configuration.
Particular compounds of the invention include:
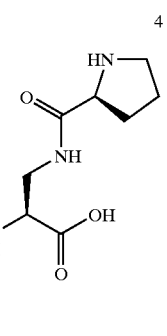
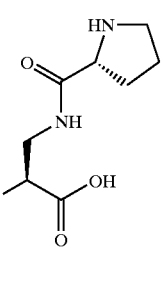
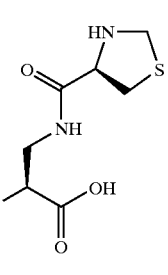
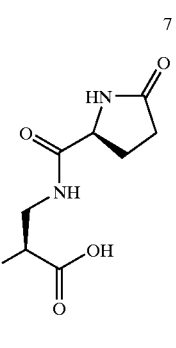
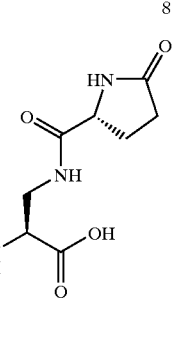

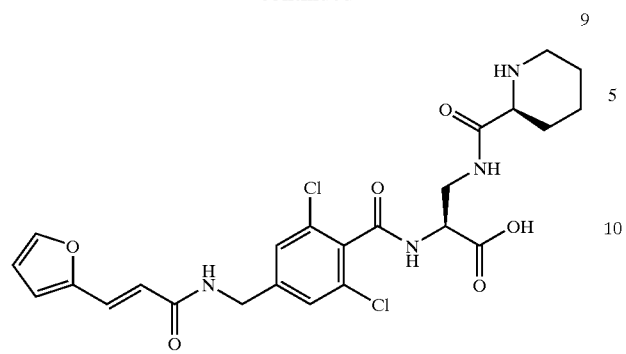
9
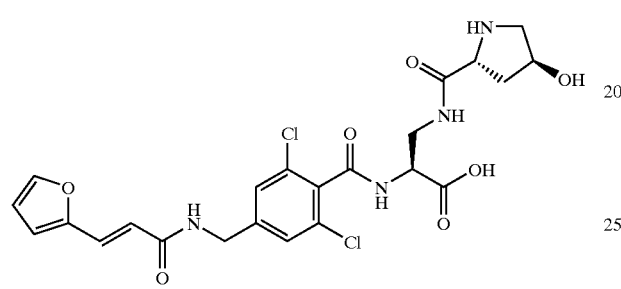
10
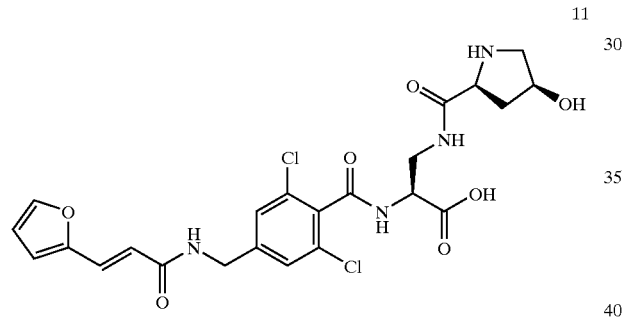
11
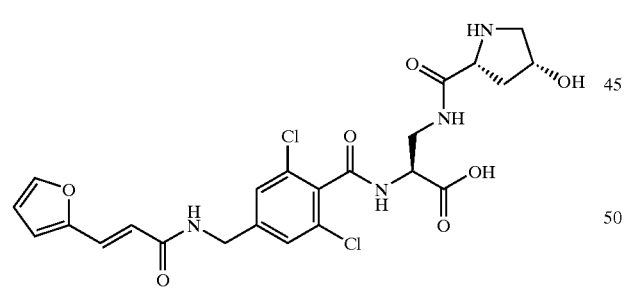
12
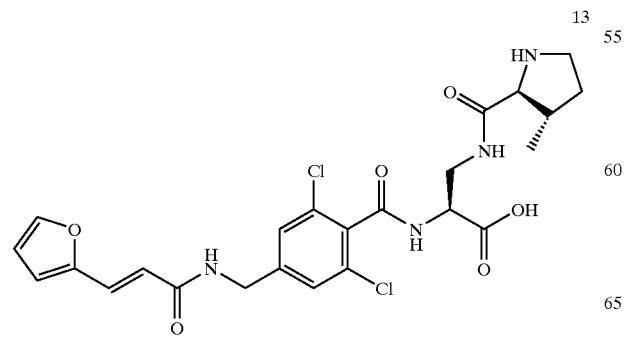
13
14
15
16
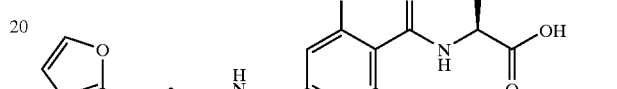
17
18

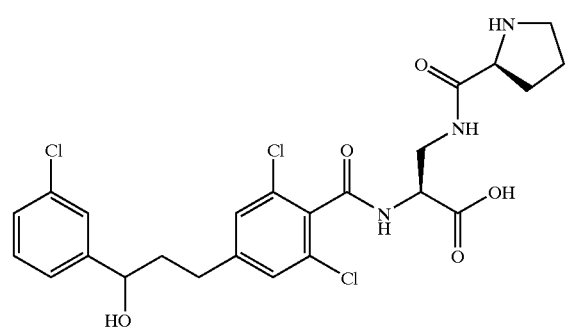
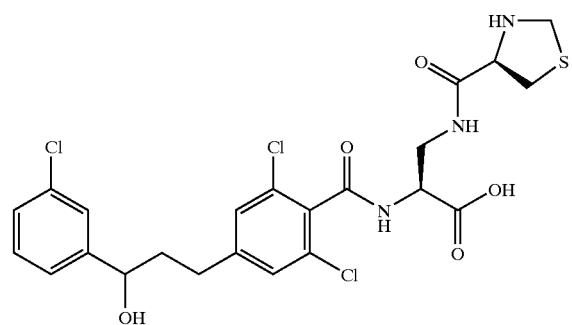
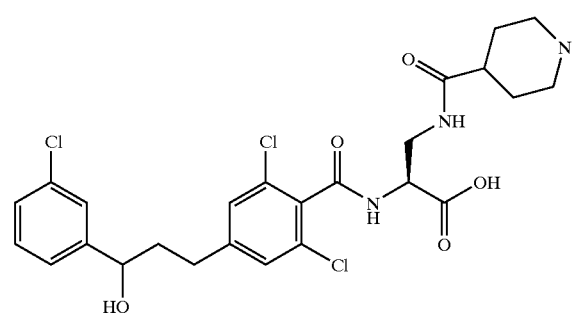
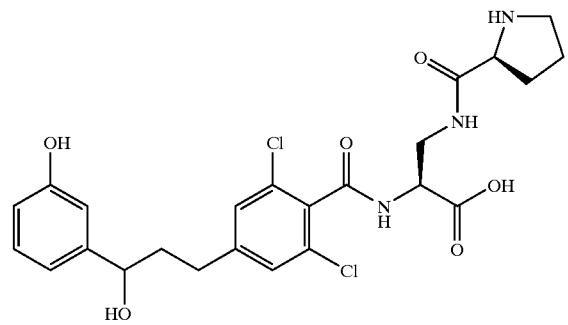
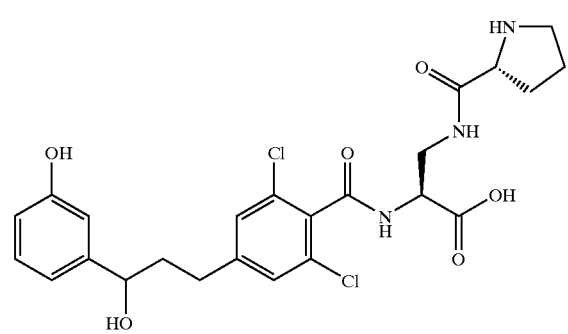
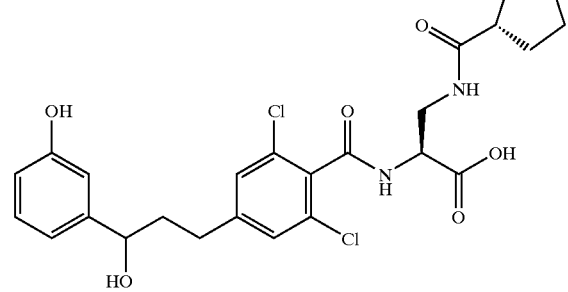

29
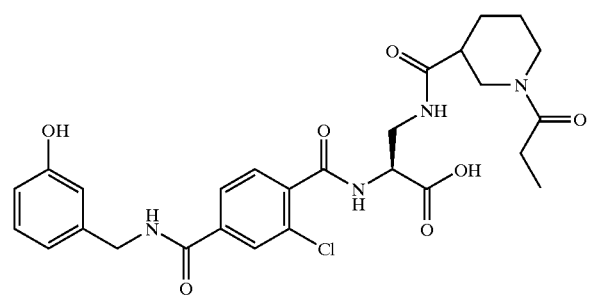
30
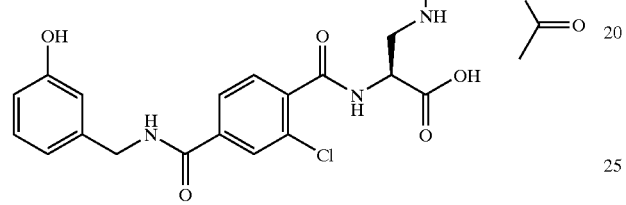
31
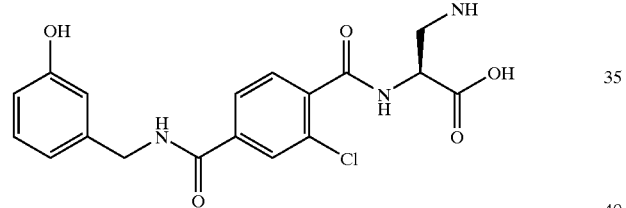
32
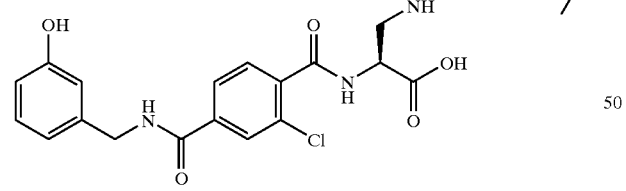
33
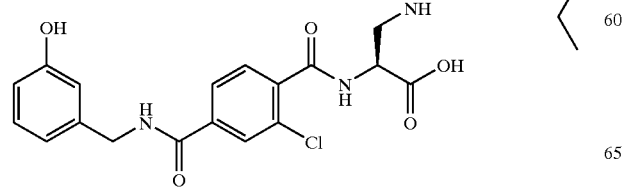
34
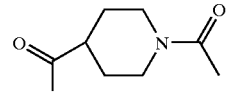
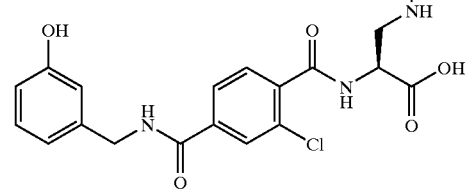
35
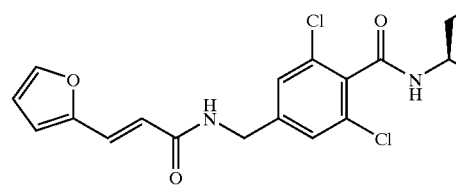
36
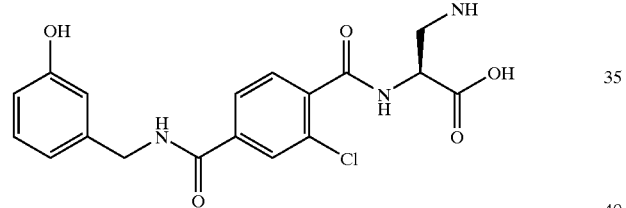
37
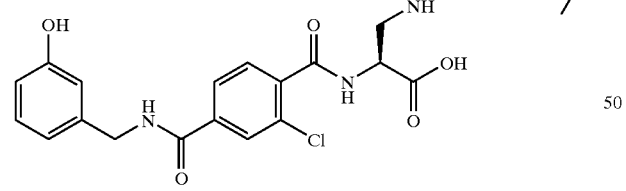
38
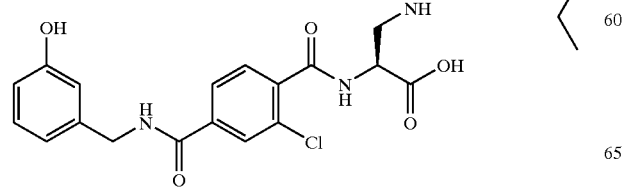

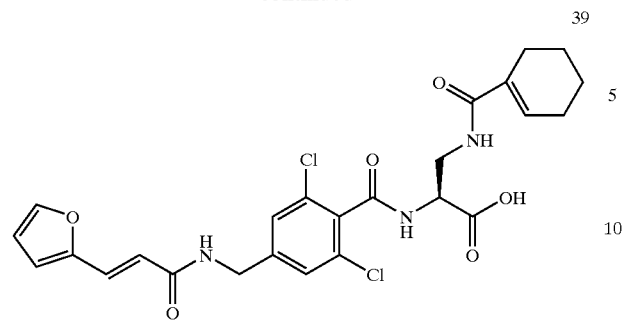
39
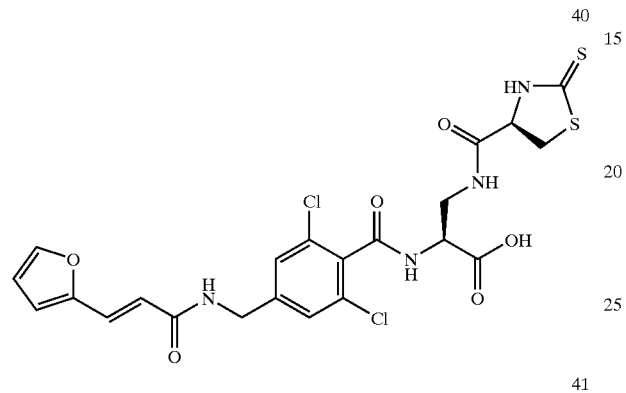
40
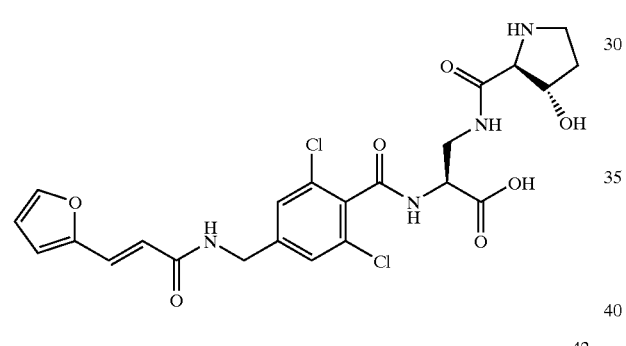
41
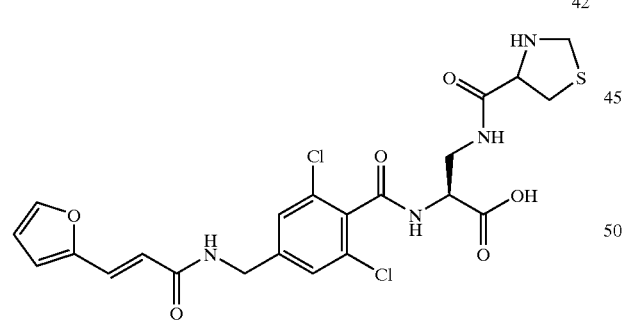
42
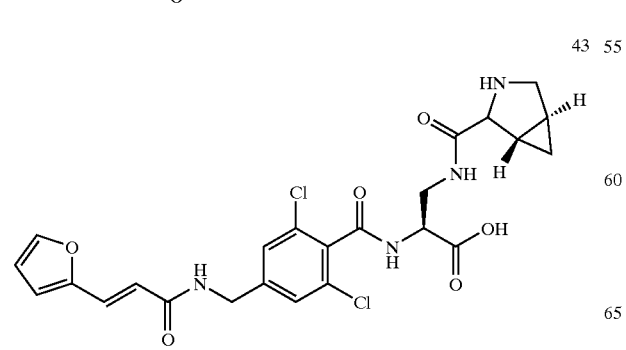
43
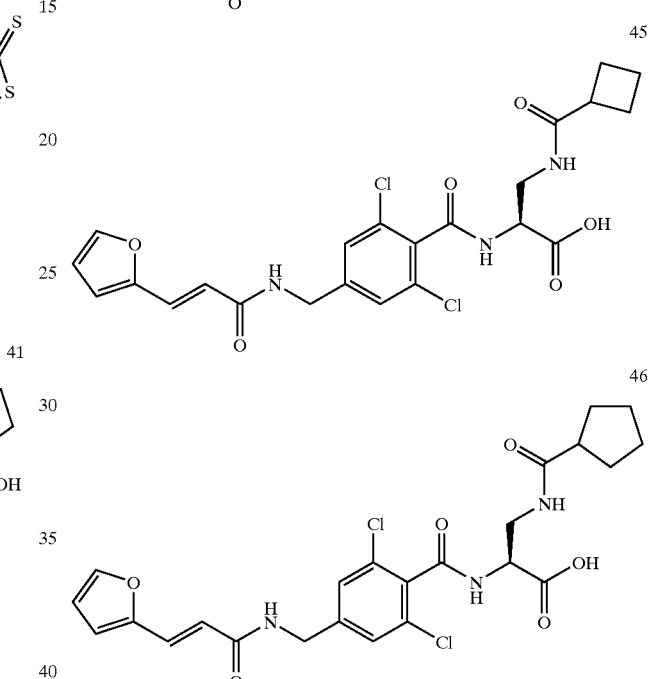
44
45
46
47
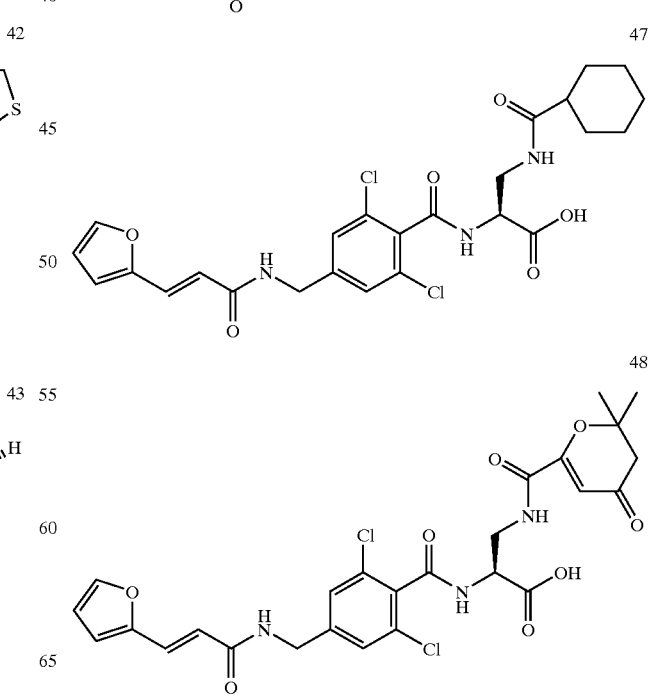
48

-continued

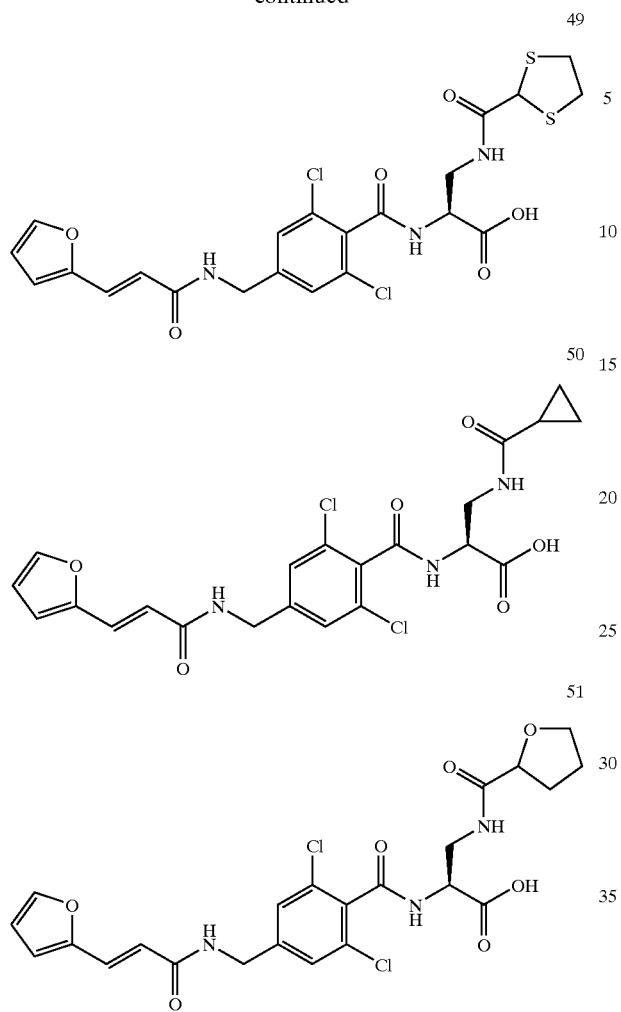

and salts, solvates, hydrates and esters thereof.

It will be appreciated that compounds of the invention may incorporate chiral centers and therefore exist as geometric and stereoisomers. All such isomers are contemplated and are within the scope of the invention whether in pure isomeric form or in mixtures of such isomers as well as racemates. Stereoisomeric compounds may be separated by established techniques in the art such as chromatography, i.e. chiral HPLC, or crystallization methods.

"Pharmaceutically acceptable" salts include both acid and base addition salts. Pharmaceutically acceptable acid addition salt refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, arylaliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicylic acid and the like.

Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Compounds of the invention may be prepared according to established organic synthesis techniques from starting materials and reagents that are commercially available or from starting materials that may be prepared from commercially available starting materials. Many standard chemical techniques and procedures are described in March, J., "Advanced Organic Chemistry" McGraw-Hill, New York, 1977; and Collman, J., "Principles and Applications of Organotransition Metal Chemistry" University Science, Mill Valley, 1987; and Larock, R., "Comprehensive Organic Transformations" Verlag, New York, 1989. It will be appreciated that depending on the particular substituents present on the compounds, suitable protection and deprotection procedures will be required in addition to those steps described herein. Numerous protecting groups are described in Greene and Wuts, Protective Groups in Organic Chemistry, 2d edition, John Wiley and Sons, 1991, as well as detailed protection and deprotection procedures. For example, suitable amino protecting groups include t-butyloxycarbonyl (Boc), fluorenylmethyloxycarbonyl (Fmoc), 2-trimethylsilylethyoxycarbonyl (Teoc), 1-methyl-1-(4-biphenylyl)ethoxycarbonyl (Bpoc), allyloxycarbonyl (Alloc), and benzyloxycarbonyl (Cbz). Carboxyl groups can be protected as fluorenylmethyl groups, or alkyl esters i.e. methyl or ethyl, or alkenyl esters such as allyl. Hydroxyl groups may be protected with trityl, monomethoxytrityl, dimethoxytrityl, and trimethoxytrityl groups.

Compounds may be prepared according to organic synthetic procedures described in U.S. patent application Ser. No. 09/6446,330 filed on 14 Sep. 2000, the entirety of which is incorporated herein by reference. Generally, compounds may be prepared according to reaction scheme 1.

Scheme 1

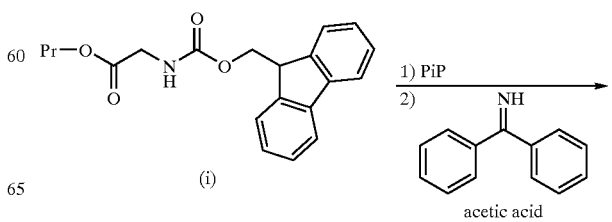

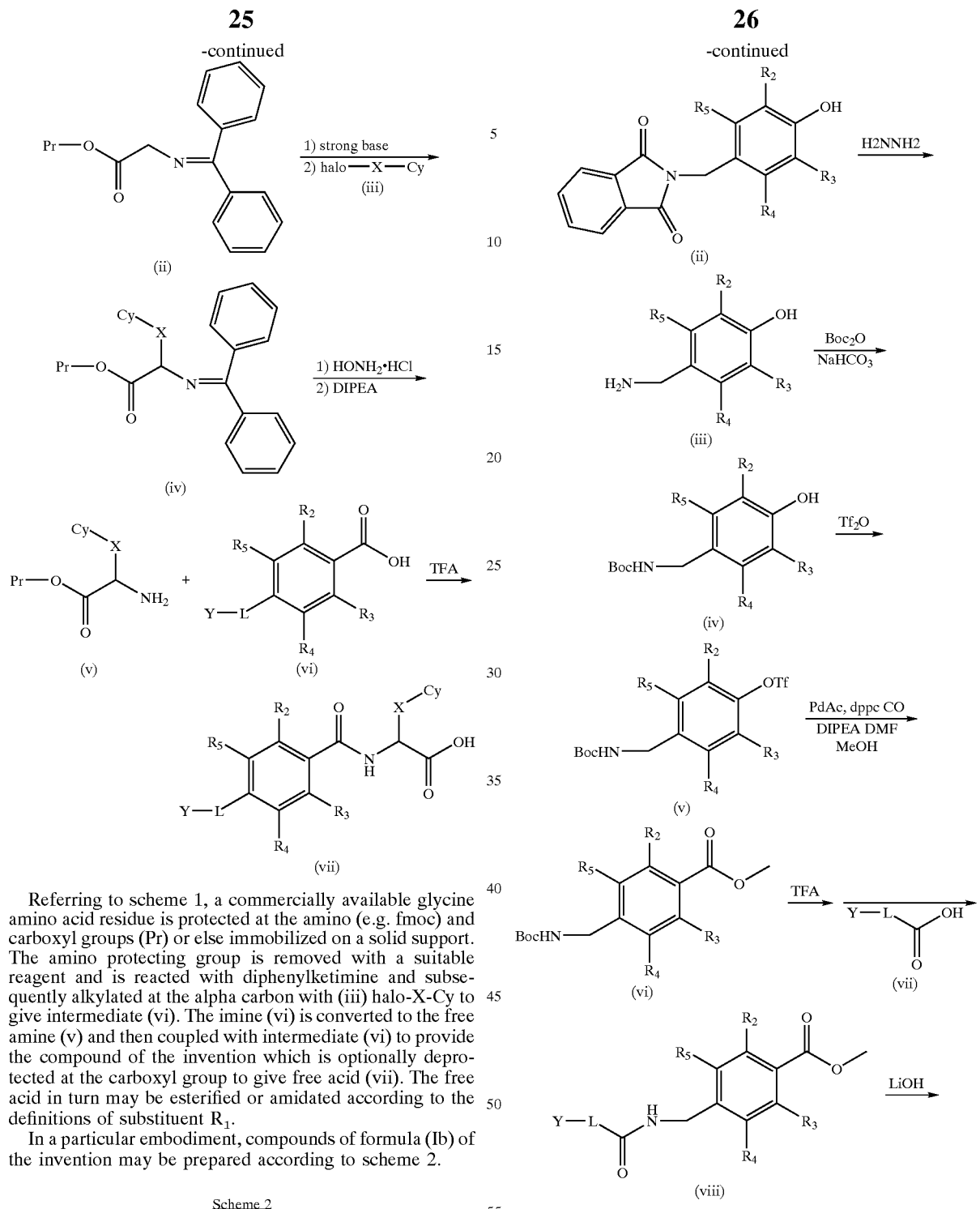

Referring to scheme 1, a commercially available glycine amino acid residue is protected at the amino (e.g. fmoc) and carboxyl groups (Pr) or else immobilized on a solid support. The amino protecting group is removed with a suitable reagent and is reacted with diphenylketimine and subsequently alkylated at the alpha carbon with (iii) halo-X-Cy to give intermediate (vi). The imine (vi) is converted to the free amine (v) and then coupled with intermediate (vi) to provide the compound of the invention which is optionally deprotected at the carboxyl group to give free acid (vii). The free acid in turn may be esterified or amidated according to the definitions of substituent $R_1$.

In a particular embodiment, compounds of formula (Ib) of the invention may be prepared according to scheme 2.

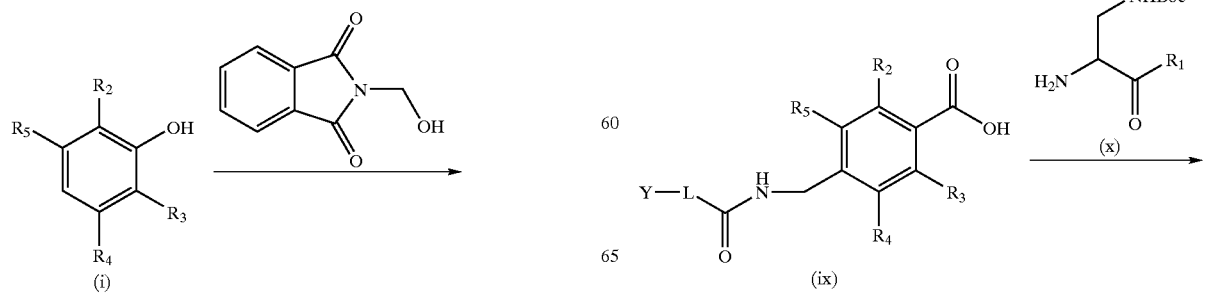

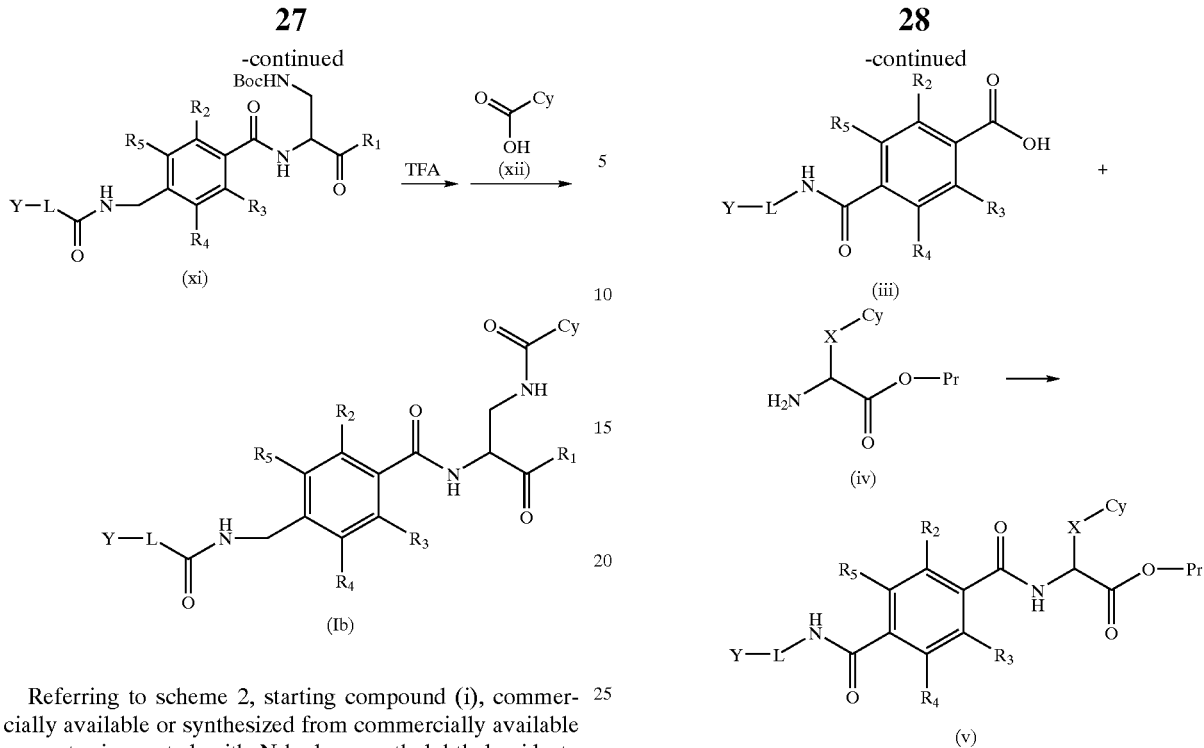

Referring to scheme 2, starting compound (i), commercially available or synthesized from commercially available reagents, is reacted with N-hydroxymethylphthalamide to give intermediate (ii) which is reacted with hydrazine to yield the free amine (iii). The amine is Boc protected (iv) by reacting with Boc₂O and sodiumbicarbonate and then reacted with triflic anhydride to give intermediate (v). The triflate intermediate (v) is then converted to the methyl ester intermediate (vi) by reacting with palladium(II) acetate and 1,3-bi(diphenylphosphino propane (dppp) and subsequently with diisopropyl ethylamine (DIPEA). The Boc group of (vi) is removed with TFA and then reacted with carboxylic acid (vii) to give intermediate (viii). In a preferred embodiment of scheme 2, intermediate (vii) Y-L-C(O)OH is furylacrylic acid or thienylacrylic acid. The methyl ester of (viii) is removed with LiOH to give the free acid which is reacted with the N-Boc protected diaminopropanoic acid/ester (x) to yield intermediate (xi). The Boc group of (xi) is removed with TFA and then reacted with carboxyl-substituted non-aromatic ring (xii) to give final compound (Ib) of the invention.

In another particular embodiment compounds of formula (Ic) of the invention may be prepared according to scheme 3.

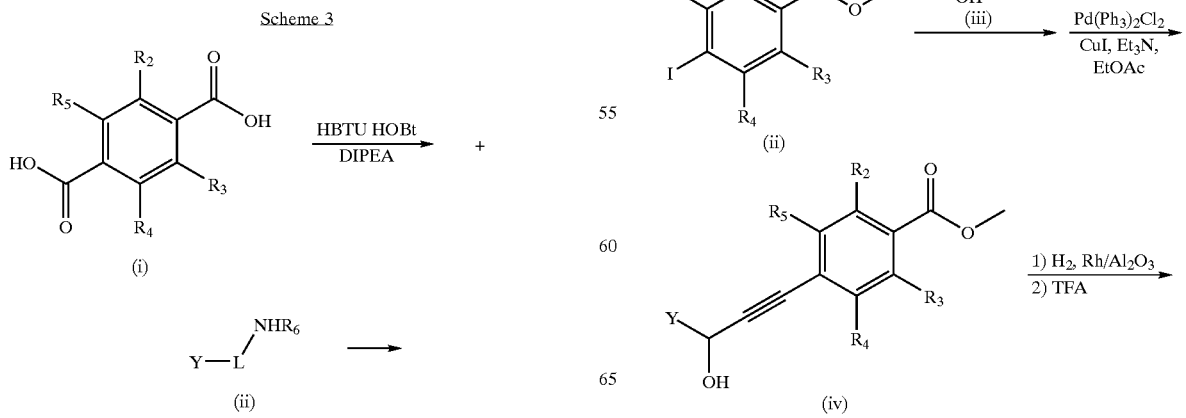

Referring to scheme 3, carboxylate starting reagent (i) is coupled with amine reagent (ii) Y-L-NHR₆ to give intermediate (iii) which is coupled with (iv) to yield compound of the invention (v). In a preferred embodiment of scheme 3, Y-L- is benzyl, optionally substituted with hydroxy, halogen, alkyl or alkoxy. More preferably Y-L- is 3-hydroxy-benzyl.

In another particular embodiment, compounds of formula (Id) of the invention may be prepared according to scheme 4.

Scheme 4

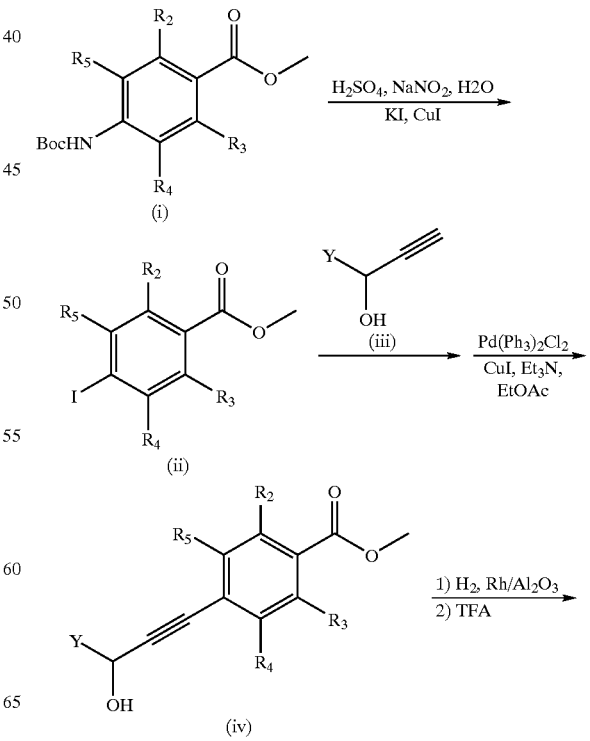

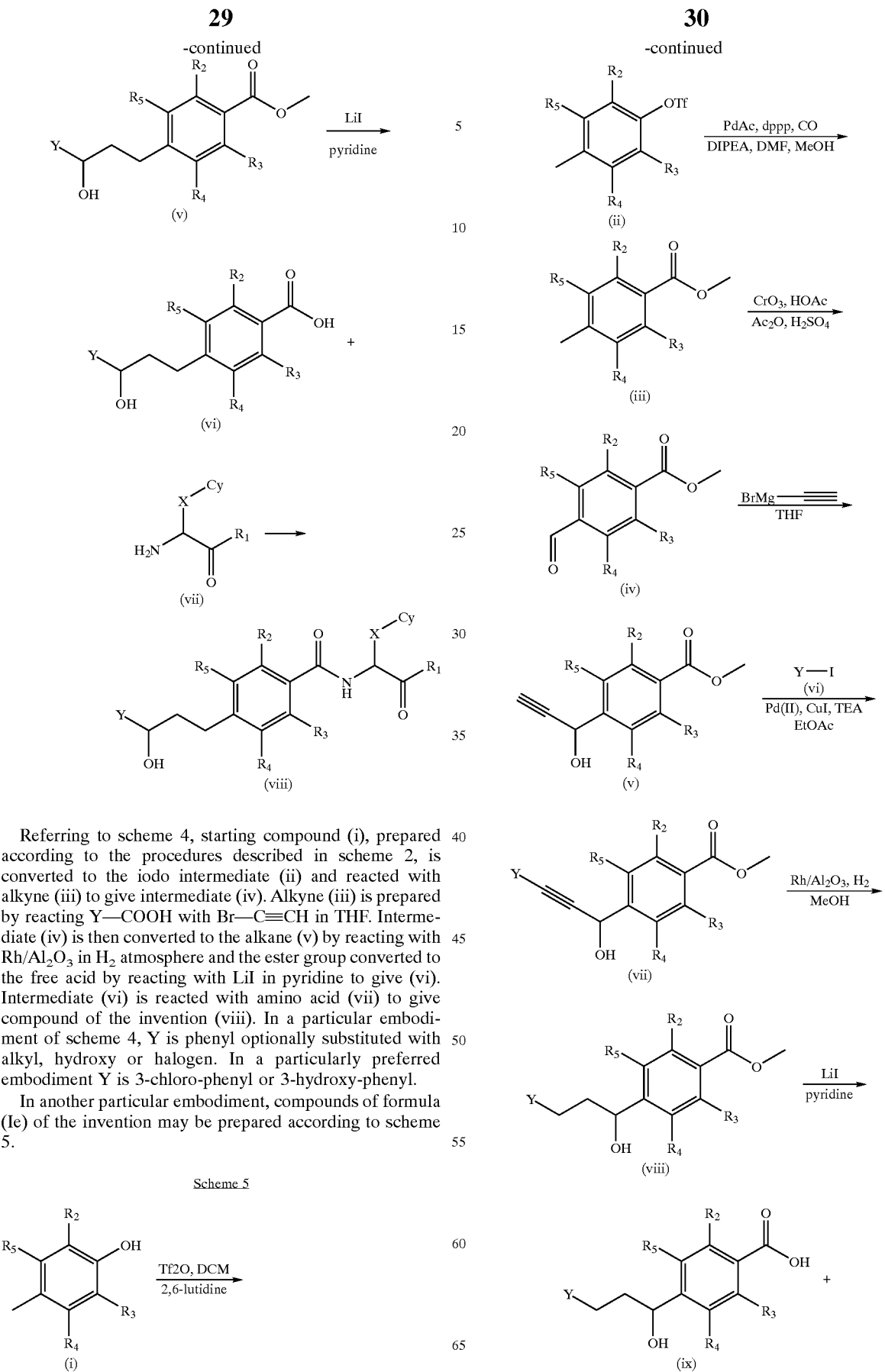

Referring to scheme 4, starting compound (i), prepared according to the procedures described in scheme 2, is converted to the iodo intermediate (ii) and reacted with alkyne (iii) to give intermediate (iv). Alkyne (iii) is prepared by reacting Y—COOH with Br—C≡CH in THF. Intermediate (iv) is then converted to the alkane (v) by reacting with Rh/Al$_2$O$_3$ in H$_2$ atmosphere and the ester group converted to the free acid by reacting with LiI in pyridine to give (vi). Intermediate (vi) is reacted with amino acid (vii) to give compound of the invention (viii). In a particular embodiment of scheme 4, Y is phenyl optionally substituted with alkyl, hydroxy or halogen. In a particularly preferred embodiment Y is 3-chloro-phenyl or 3-hydroxy-phenyl.

In another particular embodiment, compounds of formula (Ie) of the invention may be prepared according to scheme 5.

Scheme 5

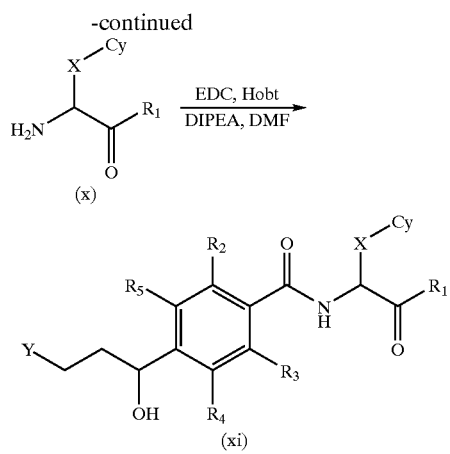

Referring to scheme 5, starting compound (i) is reacted with triflic anhydride and 2,6-lutidine to give intermediate (ii) which is converted to methyl ester (iii) by reacting with palladium(II)acetate, 1,3-bi(diphenylphosphino propane (dppp) and subsequently with diisopropyl ethylamine (DIPEA) in DMF and methanol. The ester (iii) is then reacted with $CrO_3$ in acetic acid and anhydride to give aldehyde (iv) which is reacted with Grignard reagent ethynyl-magnesium bromide in THF to give alkyne intermediate (v). Iodo reagent (vi) Y—I is reacted with (v) to give intermediate (vii) which is converted to the alkane (viii) by reacting with $Rh/Al_2O_3$ under hydrogen atmosphere. The methyl ester is converted to free acid (ix) with LiI in pyridine which is then coupled to amino acid residue (x) to give compound of the invention (xi). In preferred embodiments of scheme 5, Y is phenyl, optionally substituted with hydroxy, halogen, alkyl or alkoxy. In more preferred embodiments, Y is 3-hydroxy-phenyl or 3-chloro-phenyl.

Compounds of the invention bind to LFA-1 preferentially over Mac-1. Accordingly, in an aspect of the invention, there is provided a method of inhibiting the binding of LFA-1 to ICAMs (cellular adhesion molecules), the method comprising contacting LFA-1 with a compound of formula (I). The method may be carried out in vivo or ex vivo as a solution based or cell based assay wherein the compound of the invention is introduced to LFA-1 in the presence of a putative or known ligand (such as ICAM-1). The compound of the invention may be labeled, for example isotopically radiolabeled, or labeled with a fluorophore such as fluorescein isothiocyanate (FITC), to facilitate detection of ligand binding or reduction thereof to the protease. Thus compounds of the invention are useful for diagnostic and screening assays.

Compounds of the invention are therapeutically and/or prophylactically useful for treating diseases or conditions mediated by LFA-1 activity. Accordingly in an aspect of the invention, there is provided a method of treating a disease or condition mediated by LFA-1 in a mammal, i.e. a human, comprising administering to said mammal an effective amount of a compound of the invention. By "effective amount" is meant an amount of compound which upon administration is capable of reducing the activity of LFA-1; or the amount of compound required to prevent, inhibit or reduce the severity of any symptom associated with an LFA-1 mediated condition or disease upon administration.

Compounds of the invention or compositions thereof are useful in treating conditions or diseases including: psoriasis; responses associated with inflammatory bowel disease (such as Crohn's disease and ulcerative colitis), dermatitis, meningitis, encephalitis, uveitis, allergic conditions such as eczema and asthma, conditions involving infiltration of T-cells and chronic inflammatory responses, skin hypersensitivity reactions (including poison ivy and poison oak); atherosclerosis, autoimmune diseases such as rheumatoid arthritis, systemic lupus erythematosis (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis; pernicious anemia; diseases involving leukocyte diapedesis; CNS inflammatory disorder, multiple organ injury syndrome secondary to septicaemia or trauma; autoimmune hemolytic anemia; myasthemia gravis; antigen-antibody complex mediated diseases; all types of transplantations, including graft vs. host or host vs. graft disease, HIV and rhinovirus infection, pulmonary fibrosis, alopecia, scleredoma, endometriosus, vitiligo, ischemic reperfusion injury mediated by neutrophils such as acute myocardial infarction, restenosis following PTCA, invasive procedures such as cardiopulmanary bypass surgery, cerebral edema, stroke, traumatic brain injury, hemorragic shock, burns, ischemic kidney disease, multi-organ failure, wound healing and scar formation, atherosclerosis.

The actual amount of compound administered and the route of administration will depend upon the particular disease or condition as well as other factors such as the size, age, sex and ethnic origin of the individual being treated and is determined by routine analysis. In general, intravenous doses will be in the range from about 0.01–1000 mg/kg of patient body weight per day, preferably 0.1 to 20 mg/kg and more preferably 0.3 to 15 mg/kg. Administration may be once or multiple times per day for several days, weeks or years or may be a few times per week for several weeks or years. The amount of compound administered by other routes will be that which provides a similar amount of compound in plasma compared to the intravenous amounts described which will take into consideration the plasma bioavailability of the particular compound administered.

In methods of the invention, the compound may be administered orally (including buccal, sublingual, inhalation), nasally, rectally, vaginally, intravenously (including intra-arterially), intradermally, subcutaneously, intramuscularly and topically. Compounds will be formulated into compositions suitable for administration for example with carriers, diluents, thickeners, adjuvants etc. as are routine in the formulation art. Accordingly, another aspect of the invention provides pharmaceutical compositions comprising a compound of formula (I) and a pharmaceutically acceptable carrier, excipient or adjuvant and may also include additional active ingredients such as anti-inflammatories e.g. NSAIDs.

Dosage forms include solutions, powders, tablets, capsules, gel capsules, suppositories, topical ointments and creams and aerosols for inhalation. Formulations for non-parenteral administration may include sterile aqueous solutions which may also contain buffers, diluents and other suitable additives. Pharmaceutically acceptable organic or inorganic carrier substances suitable for non-parenteral administration which do not deleteriously react with compounds of the invention can be used. Suitable pharmaceutically acceptable carriers include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with compounds of the invention. Aqueous suspensions may contain substances which increase the viscosity of the suspension including, for example, sodium carboxymethylcellulose, sorbitol and/or dextran. optionally, the suspension may also contain stabilizers.

Compounds of the invention exhibit high oral bioavailability. Accordingly, in a preferred embodiment, compounds of the invention are administered via oral delivery. Compositions for oral administration include powders or granules, suspensions or solutions in water or non-aqueous media, capsules, sachets, troches, tablets or SECs (soft elastic capsules or caplets). Thickeners, flavoring agents, diluents, emulsifiers, dispersing aids, carrier substances or binders may be desirably added to such formulations. Such formulations may be used to effect delivering the compounds to the alimentary canal for exposure to the mucosa thereof. Accordingly, the formulation can consist of material effective in protecting the compound from pH extremes of the stomach, or in releasing the compound over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing formulations for alimentary delivery are well known in the art. See, generally *Remington's Pharmaceutical Sciences*, 18th Ed., Gennaro, ed., Mack Publishing Co., Easton, Pa., 1990. The formulations of the invention can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present in a concentration of about 0.1% to about 99% by weight of the total mixture, that is to say in amounts which are sufficient to achieve the desired dosage range. The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Compositions may also be formulated with binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods well known in the art. The preparations may also contain flavoring, coloring and/or sweetening agents as appropriate.

Formulations of the present invention suitable for oral administration may be presented as discrete units such as capsules, cachets or tablets each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

EXAMPLES

Abbreviations used in the following section: Boc=t-butyloxycarbonyl; Boc$_2$O=t-butyloxycarbonyl anhydride; DMA=dimethylacetimide; DMF=dimethylformamide; Hobt=1-hydroxybenztriazole; TFA=trifluoroacetic acid; DCM=dichloromethane; MeOH=methanol; HOAc=acetic acid; HCl=hydrochloric acid; H$_2$SO$_4$=sulfuric acid; K$_2$CO$_3$=potassium carbonate; THF=tetrahydrofuran; EtOAc=ethyl acetate; DIPEA=diisopropylethylamine; NaHCO$_3$=sodium bicarbonate; ACN=acetonitrile; Na$_2$.EDTA=ethylenediaminetetraacetic acid sodium salt; TBAF=tetrabutyl ammonium fluoride; EDC=1-(3-dimethylaminopropyl)-3-ethylcarbodiimide.HCl; TEA=triethylamine; MgSO$_4$=magnesium sulfate; TES=triethylsilane; Et$_2$O=diethyl ether; BBr$_3$=boron tribromide Example 1

Synthesis of Compounds 16, 17, 38–40, 46–50

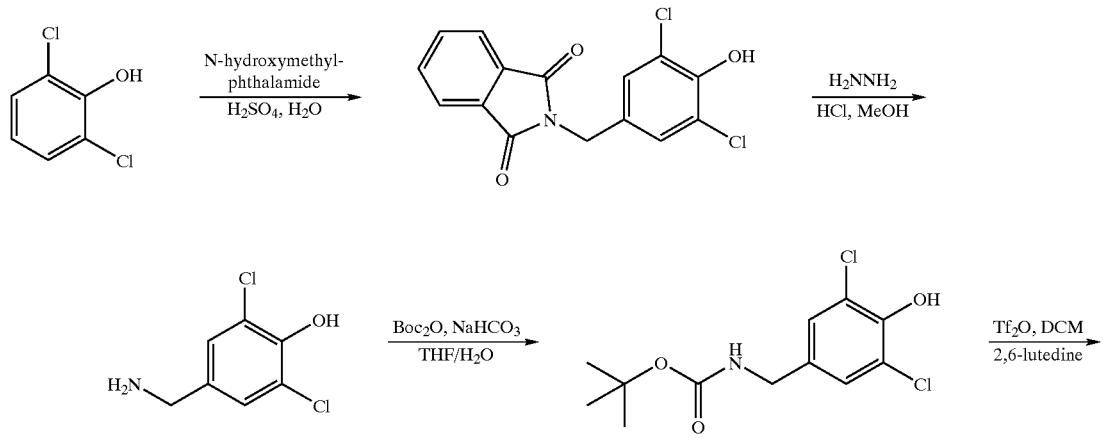

-continued
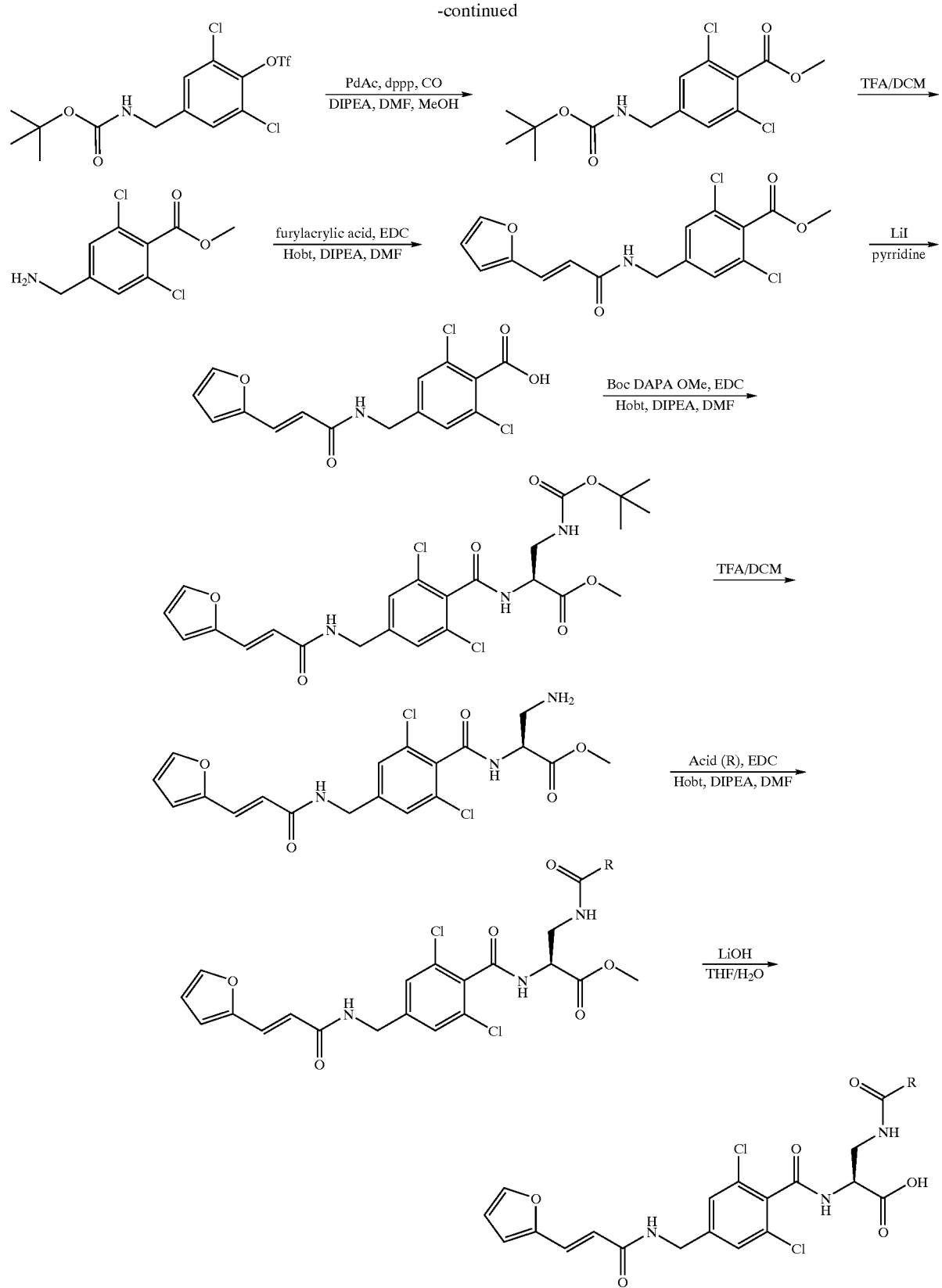
A round bottom flask was equipped with an efficient overhead stirrer and charged with concentrated $H_2SO_4$ (2.7× volume of $H_2O$) and $H_2O$ and cooled to ~−5° C. with an ethanol/ice bath. Once cool, 1 equivalent 2.6 dichloro phenol and 1 equivalent of N-(hydroxymethyl)phthalimide were added with vigorous stirring. The reaction was kept cool for 4 hours and then allowed to warm to room temperature overnight with constant stirring. The reaction generally proceeded to a point where there was just a solid in the round bottom flask. At that point EtOAc and $H_2O$ were added and stirred into the solid. Large chunks were broken up and then the precipitate was filtered and washed with more EtOAc and $H_2O$. The product was then used without further purification after drying overnight under vacuum.

1 equivalent of the dry product and methanol (22.5 ml×#g of starting material) was added to a round bottom flask equipped with a $H_2O$ condenser and stirring bar. 1.2 equivalents of hydrazine mono hydrate was added and the mixture refluxed for 4 hours. After cooling to room temperature, concentrated HCl (4.5 ml×#g of starting material) was carefully added. Upon completion of the addition, the mixture was refluxed overnight (>8 hours).

The reaction was cooled to 0° C. and the precipitated by-product was removed by filtration. The filtrate was then concentrated in vacuo.

The crude amine residue was dissolved in a 3:2 $THF/H_2O$ solution. 1.1 equivalents of solid $NaHCO_3$ and 1.1 equivalents of $Boc_2O$ were added and the mixture was stirred overnight. The reaction was concentrated, and the residue was partitioned between $H_2O$ and $Et_2O$. The aqueous layer was extracted with $Et_2O$ and the combined organic layers were dried over $MgSO_4$ and concentrated in vacuo to a solid. Recrystallization from hot methanol and $H_2O$ provided pure product.

1 equivalent of the Boc protected amine and 1.5 equivalents of 2,6-lutidine was dissolved, with mild heating when necessary, in DCM in a round bottom flask. Once the starting material had completely dissolved, the mixture was cooled to −78° C. under $N_2$ with a dry ice ethanol bath. Once cool, 2.5 equivalents of triflic anhydride was added and the reaction was allowed to slowly come to room temperature with stirring. The reaction was monitored by TLC and was generally done in 4 hours. Upon completion, the reaction was concentrated in vacuo and the residue partitioned between EtOAc and $H_2O$. The organic layer was washed twice with 0.1N $H_2SO_4$, twice with saturated $NaHCO_3$, once with brine, dried over $MgSO_4$ and concentrated in vacuo. The residue was then purified on silica gel using DCM as eluent to provide pure triflate.

1 equivalent of triflate was dissolved in DMF and MeOH in the glass insert of a high pressure Parr bomb. The starting material was then degassed while stirring with CO for 10 minutes. 0.15 equivalents palladium(II) acetate and 0.15 equivalents of 1,3-bis(diphenylphosphino)propane were then added and the mixture was then degassed while stirring with CO for another 10 minutes at which time 2.5 equivalents of diisopropyl ethyl amine was added. After properly assembling. the bomb, it was charged with 300 psi CO gas and heated to 70° C. with stirring overnight. The bomb was then cooled and vented. The mixture was transferred to a round bottom flask and concentrated in vacuo. The residue was then purified on silica gel using DCM with 1% acetone and 1% TEA as eluent to provide pure methyl ester.

The Boc protected amine was dissolved in a solution of TFA in DCM (1:1). After 20 minutes, the reaction was concentrated in vacuo. The resulting oil was dissolved in toluene and then reconcentrated in vacuo. The TFA salt of the amine was dissolved in $Et_2O$ and washed twice with a 10% solution of $K_2CO_3$ in $H_2O$ and once with brine. The organic layer was then dried over $MgSO_4$, filtered and concentrated in vacuo.

1 equivalent of the free based amine, 3 equivalents of furylacrylic acid, 3 equivalents of EDC and 1 equivalent of Hobt were dissolved DMA. The reaction was stirred at room temperature and monitored by TLC (9/1 DCM/MeOH). Upon completion, the mixture was concentrated in vacuo. The resulting oil was re suspended in $Et_2O$ and washed twice with 0.1 N $H_2SO_4$, twice with saturated $NaHCO_3$, and once with brine. The organic layer was then dried over $MgSO_4$, filtered and concentrated in vacuo. The residue was then purified on silica get using 5% methanol in DCM as eluent to provide pure methyl ester.

2.3 equivalents of lithium iodide was added to 1 equivalent of the methyl ester in pyridine, and the mixture heated at reflux for 8 hours. The reaction was concentrated in vacuo and the residue was partitioned between EtOAc and 1N HCl. The aqueous layer was extracted three times with EtOAc, and the combined organic layers were washed with 1M $NaHCO_3$, dried over $MgSO_4$ and concentrated in vacuo. The residue was dissolved in NMM and the solution concentrated in vacuo. The residue was taken up in DCM and then washed three times with 1N HCl. The organic layer was dried over $MgSO_4$ and concentrated in vacuo to provide the benzoic acid in high enough purity to be used without further purification.

1 equivalent of the acid, 2 equivalents of commercially available β-Boc-diaminopropionic acid methyl ester, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in $Et_2O$ and washed twice with 0.1 N $H_2SO_4$, twice with saturated $NaHCO_3$, and once with brine. The organic layer was then dried over $MgSO_4$, filtered and concentrated in vacuo. The residue was then purified on silica get using 5% methanol in DCM as eluent to provide pure methyl ester.

The Boc protected amine was dissolved in a solution of TFA in DCM (1:1). After 20 minutes, the reaction was concentrated in vacuo. The resulting oil was dissolved in toluene and then reconcentrated in vacuo. 1 equivalent of this amine, 2 equivalents of the appropriate commercially available carboxylic acid (compound 16, N-acetyl-D-proline; compound 17, N-acetyl-L-proline; compound 38, (−)-2-oxo-4-thiazolidinecarboxylic acid; compound 39, 1-cyclohexene-1-carboxylic acid; compound 40, (4R)-(−)-2-thioxo-4-thiazolidinecarboxylic acid; compound 45, cyclobutanecarboxylic acid; compound 46, cyclopentanecarboxylic acid; compound 47, cyclohexanecarboxylic acid; compound 48, 3,4-dihydro-2,2-dimethyl-4-oxo-2-H-pyran-6-carboxylic acid; compound 49, ethyl 1,3-dithiolane-2-carboxylate (2 equivalents of the ethyl ester was saponified with 3 equivalents of $LiOH·H_2O$ in $THF/H_2O$ (3/1) The reaction was monitored by TLC (9/1 DCM/MeOH). Upon completion, the mixture was acidified to pH 2 with 1M HCl and then concentrated in vacuo. The resulting solid was used without further purification); compound 50, cyclopropanecarboxylic acid; compound 51, tetrahydro-2-furoic acid), 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in $Et_2O$ and washed twice with 0.1 N $H_2SO_4$, twice with saturated $NaHCO_3$, and once with brine. The organic layer was then dried over $MgSO_4$, filtered and concentrated in vacuo. The residue was then purified on silica get using 5% methanol in DCM as eluent to provide pure methyl ester.

1 equivalent of the resultant methyl ester was dissolved in THF/H₂O (3/1) and 3 equivalents of LiOH·H₂O was added. The reaction was monitored by TLC (9/1 DCM/MeOH). Upon completion, the mixture was acidified to pH 2 with 1M HCl and then concentrated in vacuo. The resulting solid was resuspended in Et₂O and washed twice with 0.1 M HCl and once with brine. The organic layer was then dried over MgSO₄, filtered and concentrated in vacuo. The resulting acid was then purified by reverse phase HPLC, verified by electrospray mass spectrometry and lyophilized to a powder.

Example 2

Synthesis of Compounds 1–15, 41, 43

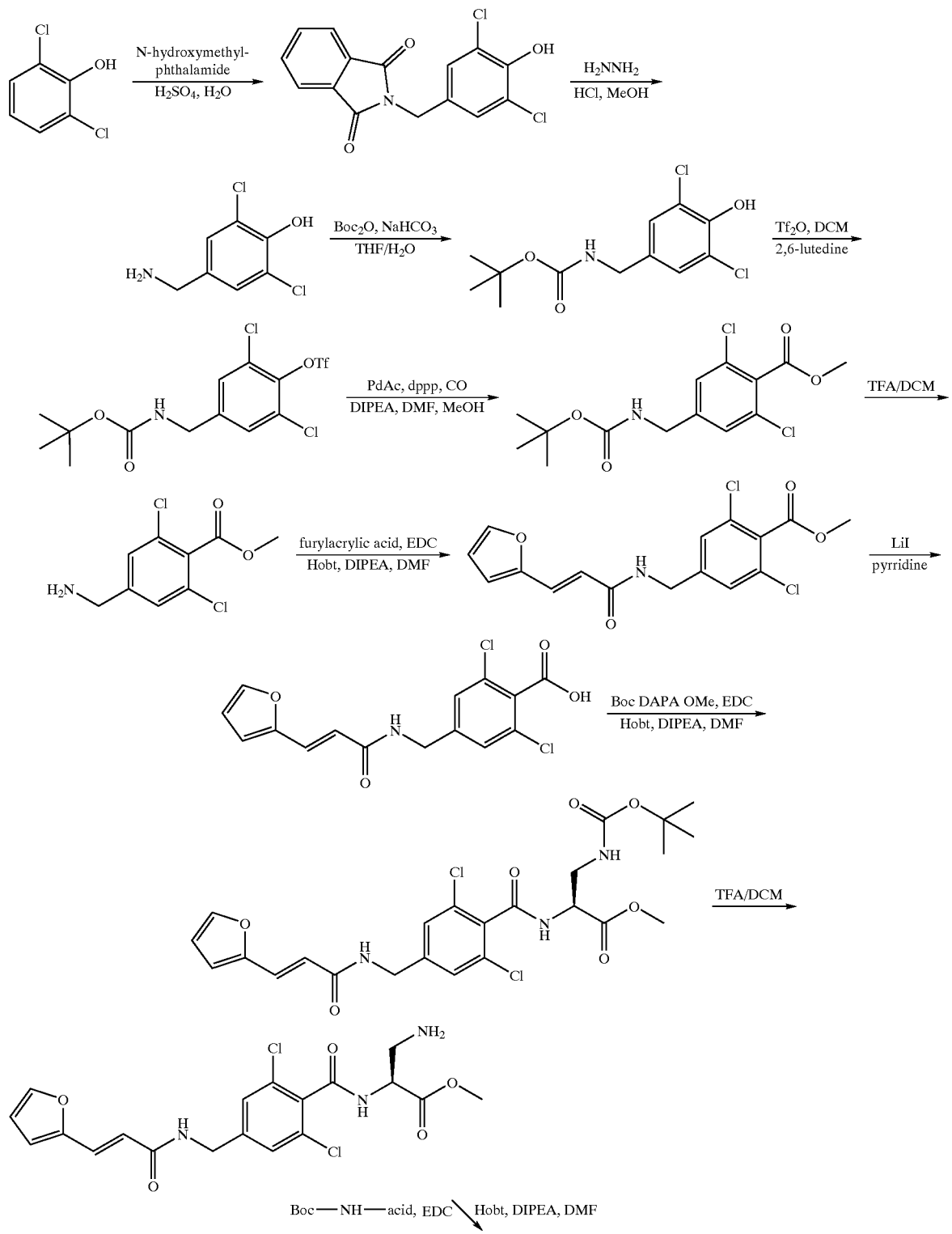

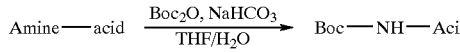

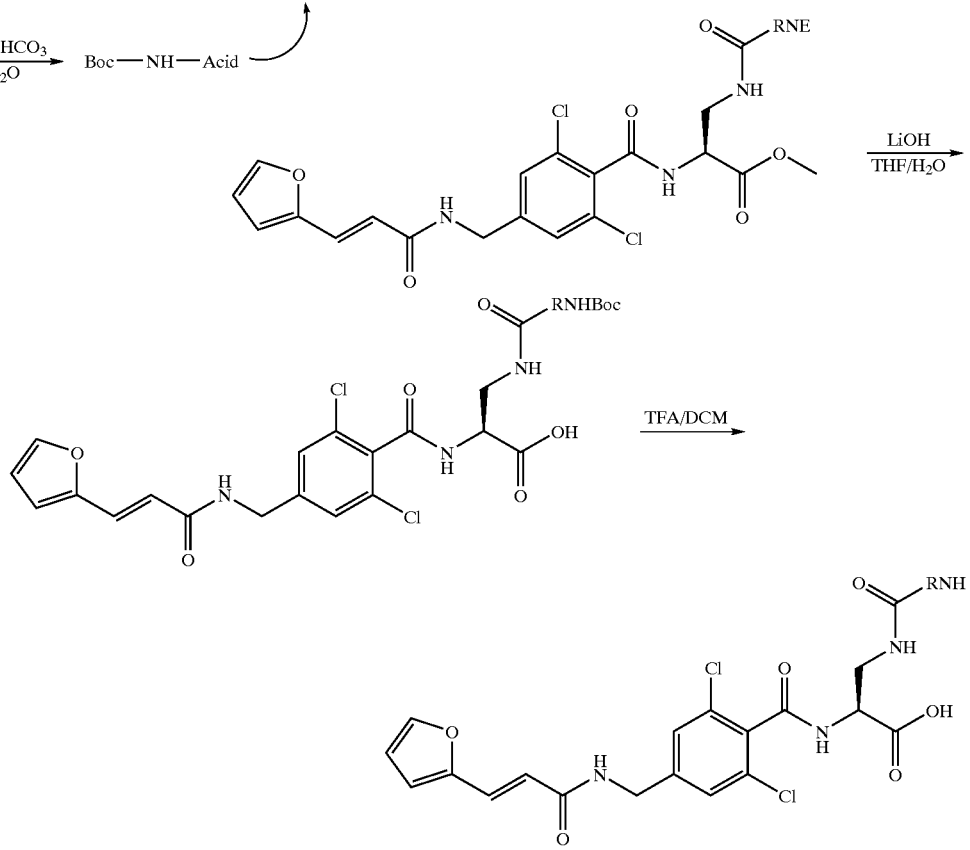

A round bottom flask was equipped with an efficient overhead stirrer and charged with concentrated $H_2SO_4$ (2.7× volume of $H_2O$) and $H_2O$ and cooled to ~−5° C. with an ethanol/ice bath. Once cool, 1 equivalent 2.6 dichloro phenol and 1 equivalent of N-(hydroxymethyl)phthalimide were added with vigorous stirring. The reaction was kept cool for 4 hours and then allowed to warm to room temperature overnight with constant stirring. The reaction generally proceeds to a point where there was just a solid in the round bottom flask. At this point EtOAc and $H_2O$ were added and stirred into the solid. Large chunks were broken up and then the precipitate was filtered and washed with more EtOAc and $H_2O$. The product was then used without further purification after drying overnight under vacuum.

1 equivalent of the dry product and methanol (22.5 ml×#g of starting material) was added to a round bottom flask equipped with a $H_2O$ condenser and stirring bar. 1.2 equivalents of hydrazine mono hydrate was added and the mixture refluxed for 4 hours. After cooling to room temperature, concentrated HCl (4.5 ml×#g of starting material) was carefully added. Upon completion of the addition, the mixture was refluxed overnight (>8 hours). The reaction was cooled to 0° C. and the precipitated by-product was removed by filtration. The filtrate was then concentrated in vacuo.

The crude amine residue was dissolved in a 3:2 THF/$H_2O$ solution. 1.1 equivalents of solid $NaHCO_3$ and 1.1 equivalents of $Boc_2O$ were added and the mixture was stirred overnight. The reaction was concentrated, and the residue was partitioned between $H_2O$ and $Et_2O$. The aqueous layer was extracted with $Et_2O$ and the combined organic layers were dried over $MgSO_4$ and concentrated in vacuo to a solid. Recrystallization from hot methanol and $H_2O$ provided pure product.

1 equivalent of the Boc protected amine and 1.5 equivalents of 2,6-lutidine was dissolved, with mild heating when necessary, in DCM in a round bottom flask. Once the starting material had completely dissolved, the mixture was cooled to −78° C. under $N_2$ with a dry ice ethanol bath. Once cool, 2.5 equivalents of triflic anhydride was added and the reaction was allowed to slowly come to room temperature with stirring. The reaction was monitored by TLC and was generally done in 4 hours. Upon completion, the reaction was concentrated in vacuo and the residue partitioned between EtOAc and $H_2O$. The organic layer was washed twice with 0.1N $H_2SO_4$, twice with saturated $NaHCO_3$, once with brine, dried over $MgSO_4$ and concentrated in vacuo. The residue was then purified on silica gel using DCM as eluent to provide pure triflate.

1 equivalent of triflate was dissolved in DMF and MeOH in the glass insert of a high pressure Parr bomb. The starting material was then degassed while stirring with CO for 10 minutes. 0.15 equivalents palladium(II) acetate and 0.15 equivalents of 1,3-bis(diphenylphosphino)propane were then added and the mixture was then degassed while stirring with CO for another 10 minutes at which time 2.5 equivalents of diisopropyl ethyl amine was added. After properly assembling the bomb, it was charged with 300 psi CO gas and heated to 70° C. with stirring overnight. The bomb was then cooled and vented. The mixture was transferred to a round bottom flask and concentrated in vacuo. The residue was then purified on silica gel using DCM with 1% acetone and 1% TEA as eluent to provide pure methyl ester.

The Boc protected amine was dissolved in a solution of TFA in DCM (1:1). After 20 minutes, the reaction was concentrated in vacuo. The resulting oil was dissolved in toluene and then reconcentrated in vacuo. The TFA salt of the amine was dissolved in Et₂O and washed twice with a 10% solution of K₂CO₃ in H₂O and once with brine. The organic layer was then dried over MgSO₄, filtered and concentrated in vacuo.

1 equivalent of the free based amine, 3 equivalents of furylacrylic acid, 3 equivalents of EDC and 1 equivalent of Hobt were dissolved DMA. The reaction was stirred at room temperature and monitored by TLC (9/1 DCM/MeOH). Upon completion, the mixture was concentrated in vacuo. The resulting oil was re suspended in Et₂O and washed twice with 0.1 N H₂SO₄, twice with saturated NaHCO₃, and once with brine. The organic layer was then dried over MgSO₄, filtered and concentrated in vacuo. The residue was then purified on silica get using 5% methanol in DCM as eluent to provide pure methyl ester.

2.3 equivalents of lithium iodide was added to 1 equivalent of the methyl ester in pyridine, and the mixture heated at reflux for 8 hours. The reaction was concentrated in vacuo and the residue was partitioned between EtOAc and 1N HCl. The aqueous layer was extracted three times with EtOAc, and the combined organic layers were washed with 1M NaHCO₃, dried over MgSO₄ and concentrated in vacuo. The residue was dissolved in NMM and the solution concentrated in vacuo. The residue was taken up in DCM and then washed three times with 1N HCl. The organic layer was dried over MgSO₄ and concentrated in vacuo to provide the benzoic acid in high enough purity to be used without further purification.

1 equivalent of the acid, 2 equivalents of commercially available β-Boc-diaminopropionic acid methyl ester, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et₂O and washed twice with 0.1 N H₂SO₄, twice with saturated NaHCO₃, and once with brine. The organic layer was then dried over MgSO₄, filtered and concentrated in vacuo. The residue was then purified on silica get using 5% methanol in DCM as eluent to provide pure methyl ester.

The Boc protected amine was dissolved in a solution of TFA in DCM (1:1). After 20 minutes, the reaction was concentrated in vacuo. The resulting oil was dissolved in toluene and then reconcentrated in vacuo. 1 equivalent of this amine, 2 equivalents of the appropriate commercially available carboxylic acid ((N-Boc acids were purchased where available. Other acids were purchased as the free amine and Boc protected by the following procedure: The amine was dissolved in a 3:2 THF/H₂O solution. 1.1 equivalents of solid NaHCO₃ and 1.1 equivalents of Boc₂O were added and the mixture was stirred overnight. The reaction was concentrated to remove the THF, and the resulting aqueous layer was partitioned with hexanes. The aqueous layer was then acidified to pH 2 with 1N HCl and then partitioned twice with EtOAc. The combined organic layers were dried over MgSO₄ and concentrated in vacuo. The resulting product was used without further purification) compound 1 D,L-pipecolinic acid; compound 2, nipecotic acid; compound 3, isonipecotic acid; compound 4, N-Boc-L-proline; compound 5, N-Boc-D-proline; compound 6, Boc-L-thiazolidine-4-carboxylic acid; compound 7, N-Boc-L-pyroglutamic acid; compound 8, N-Boc-D-pyroglutamic acid; compound 9, L-pipecolinic acid; compound 10, D-cis-4-hydroxyproline; compound 11, L-cis-4-hydroxyproline; compound 12, D-hydroxyproline; compound 13, (2S, 3S)-3-methylpyrrolidine-2-carboxylic acid; compound 14, N-Boc-L-hydroxyproline; compound 15, Boc-D-thiazolidine-4-carboxylic acid; compound 41, L-3-hydroxyproline; compound 43, trans-3-azabicyclo[3.1.0]hexane-2-carboxylic acid), 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et₂O and washed twice with 0.1 N H₂SO₄, twice with saturated NaHCO₃, and once with brine. The organic layer was then dried over MgSO₄, filtered and concentrated in vacuo. The residue was then purified on silica get using 5% methanol in DCM as eluent to provide pure methyl ester.

1 equivalent of the resultant methyl ester was dissolved in THF/H₂O (3/1) and 3 equivalents of LiOH·H₂O was added. The reaction was monitored by TLC (9/1 DCM/MeOH). Upon completion, the mixture was acidified to pH 2 with 1M HCl and then concentrated in vacuo. The resulting solid was re suspended in Et₂O and washed twice with 0.1 M HCl and once with brine. The organic layer was then dried over MgSO₄, filtered and concentrated in vacuo.

Where appropriate the Boc protected residue was dissolved in a solution of TFA in DCM (1:1). After 20 minutes, the reaction was concentrated in vacuo. The resulting oil was dissolved in toluene and then reconcentrated in vacuo. The resulting acid was then purified by reverse phase HPLC, verified by electrospray mass spectrometry and lyophilized to a powder.

Example 3

Synthesis of Compounds 18–21

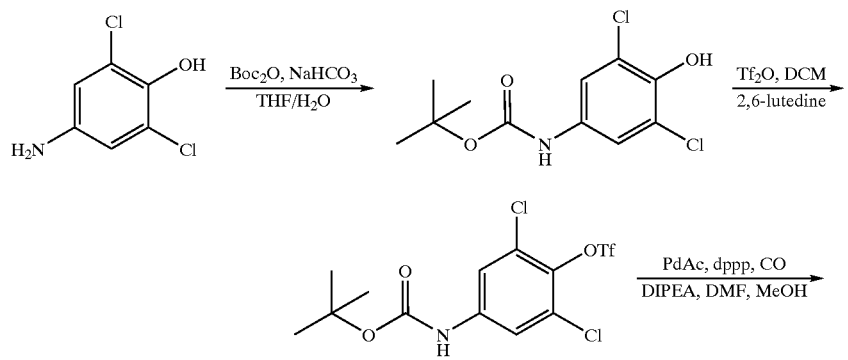

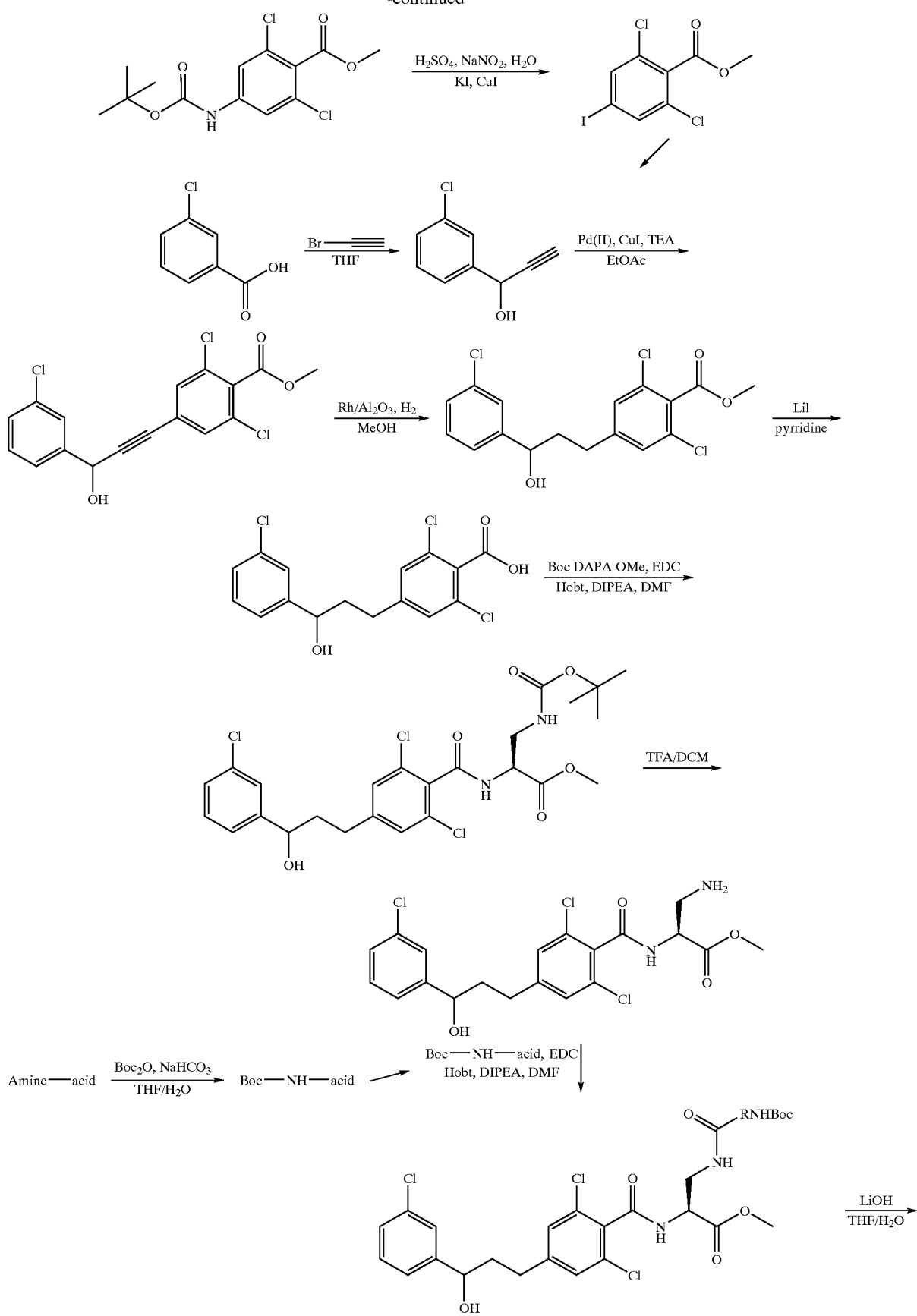

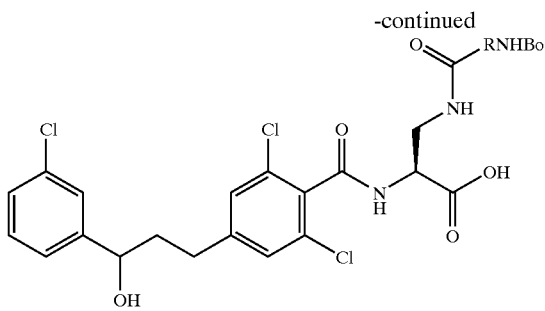

-continued

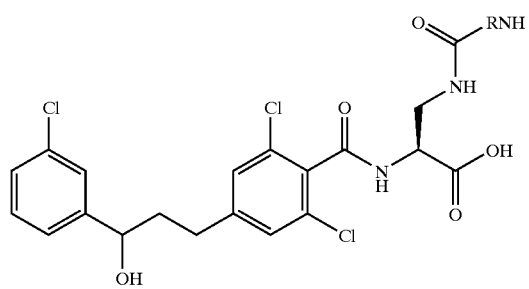

TFA/DCM 1 equivalent of 4-amino-2,6-dichlorophenol was dissolved in a 3:2 THF/H$_2$O solution. 1.1 equivalents of solid NaHCO$_3$ and 1.1 equivalents of Boc$_2$O were added and the solution was stirred overnight. The reaction was concentrated, and the residue was partitioned between H$_2$O and Et$_2$O. The aqueous layer was extracted with Et$_2$O and the combined organic layers were dried over MgSO$_4$ and concentrated in vacuo to a solid. Recrystallization out of Et$_2$O/hexane provided pure product.

1 equivalent of the phenol was dissolved in DCM containing 2.6 equivalents of 2,6-lutidine and the mixture was cooled to −78° C. After adding 1.25 equivalents of triflic anhydride the stirring reaction was allowed to warm to room temperature overnight. The reaction was then concentrated, and the residue was partitioned between Et$_2$O and H$_2$O. The aqueous layer was extracted with Et$_2$O and the combined organic layers were dried over MgSO$_4$ and concentrated in vacuo. The residue was purified by silica gel flash chromatography (9:1 hexane/Et$_2$O) to provide the pure triflate.

To a stirring solution of 1 equivalent of the triflate in a 2/1 mixture of DMF/MeOH was added 0.15 equivalents of 1,3-bis(diphenylphosphino)-propane and 2.5 equivalents of TEA. Carbon monoxide gas was bubbled through this solution for 15 minutes, then 0.15 equivalents of Pd(OAc)2 was added and the reaction was stirred at 70° C. for 5–7 hours under an atmosphere of CO (using a balloon filled with CO). The reaction was then concentrated in vacuo, and the residue was partitioned between Et$_2$O and H$_2$O. The aqueous layer was extracted twice with Et$_2$O and the combined organic layers were dried over MgSO$_4$, filtered through a plug of silica gel and concentrated in vacuo. The residue was purified by silica gel flash chromatography (9:1:0.02 hexane/DCM/Et$_2$O) to provide the pure methyl ester.

1 equivalent of the Boc-aniline was dissolved in methanol and the solution saturated with HCl. The reaction was heated at 50° C. for 3 h, then concentrated in vacuo. The pale yellow solid was heated in 35% H$_2$SO$_4$ until complete dissolution occurred. Upon cooling the mixture by the addition of ice H$_2$O the amine bisulfate precipitated. The reaction flask was cooled in an ice bath and the mixture stirred vigorously while 1.1 equivalents of sodium nitrite in H$_2$O was added drop wise. The reaction was stirred at 0° C. for another 1.5 hours. An aqueous solution of 10 equivalents of KI was added, followed immediately with 17 equivalents CuI. The reaction was stirred at room temperature for 14 hours, then extracted 3 times with Et$_2$O. The combined organic layers were washed with 1M NaHCO$_3$, brine, and dried over MgSO$_4$, then concentrated in vacuo. The residue was purified by silica gel flash chromatography (95:5 hexane/Et$_2$O) to provide the pure aryl iodide methyl ester.

A solution of 1 equivalent of 3-Chlorobenzaldehyde in THF was cooled to −78° C. and 1.1 equivalents of 0.5M ethynylmagnesium bromide/THF was added. After stirring the reaction at room temperature for 3 hours, it was diluted with Et$_2$O and washed twice with 10% citric acid. The combined aqueous layers were back-extracted once with Et$_2$O. The combined organic layers were washed twice with saturated aqueous NaHCO$_3$, dried over MgSO$_4$ and concentrated in vacuo. The residue was purified by silica gel flash chromatography (4:1 to 3:2 hexane/Et$_2$O) to provide the pure alkyne.

1 equivalent of the aryl iodide methyl ester was dissolved in EtOAc and the solution was degassed by passing N2 through a pipette and into the solution for 10 minutes. 1.25 equivalents of the alkyne was added, followed by 0.02 equivalents of dichlorobis(triphenylphosphine)palladium (II), 0.04 equivalents of CuI and 5 equivalents TEA. The reaction was stirred for 14 hours, diluted with EtOAc, washed twice with 5% Na$_2$.EDTA, brine and then dried over MgSO$_4$ and concentrated in vacuo. The residue was purified by silica gel flash chromatography (gradient elution, using Et$_2$O to EtOAc) to provide the pure aryl alkyne.

1 equivalent of the aryl alkyne was dissolved in MeOH and the solution was degassed by passing N2 through a pipette and into the solution for 10 minutes. The 5% Rh/Al$_2$O$_3$ was added, one balloon-full of hydrogen was passed through the solution, and the reaction was stirred under an atmosphere of H$_2$ (using a balloon) for 7 hours, after which the reaction was filtered through a pad of celite and concentrated in vacuo. The residue was purified by silica gel flash chromatography (gradient elution, using Et$_2$O to EtOAc) to provide the pure product.

2.3 equivalents of lithium iodide was added to 1 equivalent of the methyl ester in pyridine, and the mixture heated at reflux for 8 hours. The reaction was concentrated in vacuo and the residue was partitioned between EtOAc and 1N HCl. The aqueous layer was extracted three times with EtOAc, and the combined organic layers were washed with 1M NaHCO$_3$, dried over MgSO$_4$ and concentrated in vacuo. The residue was dissolved in NMM and the solution concentrated in vacuo. The residue was taken up in DCM and then washed three times with 1N HCl. The organic layer was dried over MgSO$_4$ and concentrated in vacuo to provide the benzoic acid in high enough purity to be used without further purification.

1 equivalent of the acid, 2 equivalents of commercially available β-Boc-diaminopropionic acid methyl ester, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et$_2$O and washed twice with 0.1 N H$_2$SO$_4$, twice with saturated NaHCO$_3$, and once with brine. The organic layer was then dried over MgSO$_4$, filtered and concentrated in vacuo. The residue was then purified on silica get using 5% methanol in DCM as eluent to provide pure methyl ester.

The Boc protected amine was dissolved in a solution of TFA in DCM (1:1). After 20 minutes, the reaction was concentrated in vacuo. The resulting oil was dissolved in toluene and then reconcentrated in vacuo. 1 equivalent of this amine, 2 equivalents of the appropriate commercially available carboxylic acid ((N-Boc acids were purchased where available. Other acids were purchased as the free amine and Boc protected by the following procedure: The amine was dissolved in a 3:2 THF/H$_2$O solution. 1.1 equivalents of solid NaHCO$_3$ and 1.1 equivalents of Boc$_2$O were added and the mixture was stirred overnight. The reaction was concentrated to remove the THF, and the resulting aqueous layer was partitioned with hexanes. The aqueous layer was then acidified to pH 2 with 1N HCl and then partitioned twice with EtOAc. The combined organic layers were dried over MgSO$_4$ and concentrated in vacuo. The resulting product was used without further purification) example 18, N-Boc-D-proline; example 19, N-Boc-L-proline; example 20, Boc-L-thiazolidine-4-carboxylic acid; example 21, isonipecotic acid; 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et$_2$O and washed twice with 0.1 N H$_2$SO$_4$, twice with saturated NaHCO$_3$, and once with brine. The organic layer was then dried over MgSO$_4$, filtered and concentrated in vacuo. The residue was then purified on silica get using 5% methanol in DCM as eluent to provide pure methyl ester.

1 equivalent of the resultant methyl ester was dissolved in THF/H$_2$O (3/1) and 3 equivalents of LiOH·H$_2$O was added. The reaction was monitored by TLC (9/1 DCM/MeOH). Upon completion, the mixture was acidified to pH 2 with 1M HCl and then concentrated in vacuo. The resulting solid was re suspended in Et$_2$O and washed twice with 0.1 M HCl and once with brine. The organic layer was then dried over MgSO$_4$, filtered and concentrated in vacuo.

The Boc protected residue was dissolved in a solution of TFA in DCM (1:1). After 20 minutes, the reaction was concentrated in vacuo. The resulting oil was dissolved in toluene and then reconcentrated in vacuo. The resulting acid was then purified by reverse phase HPLC, verified by electrospray mass spectrometry and lyophilized to a powder.

Example 4

Synthesis of Compounds 22–25

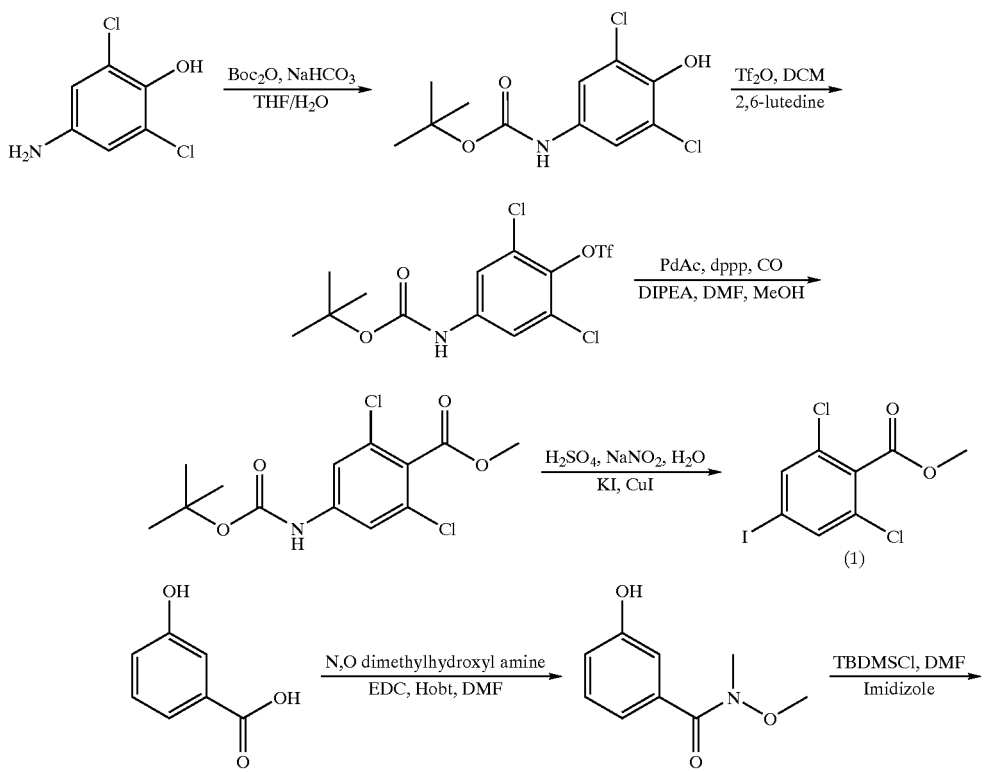

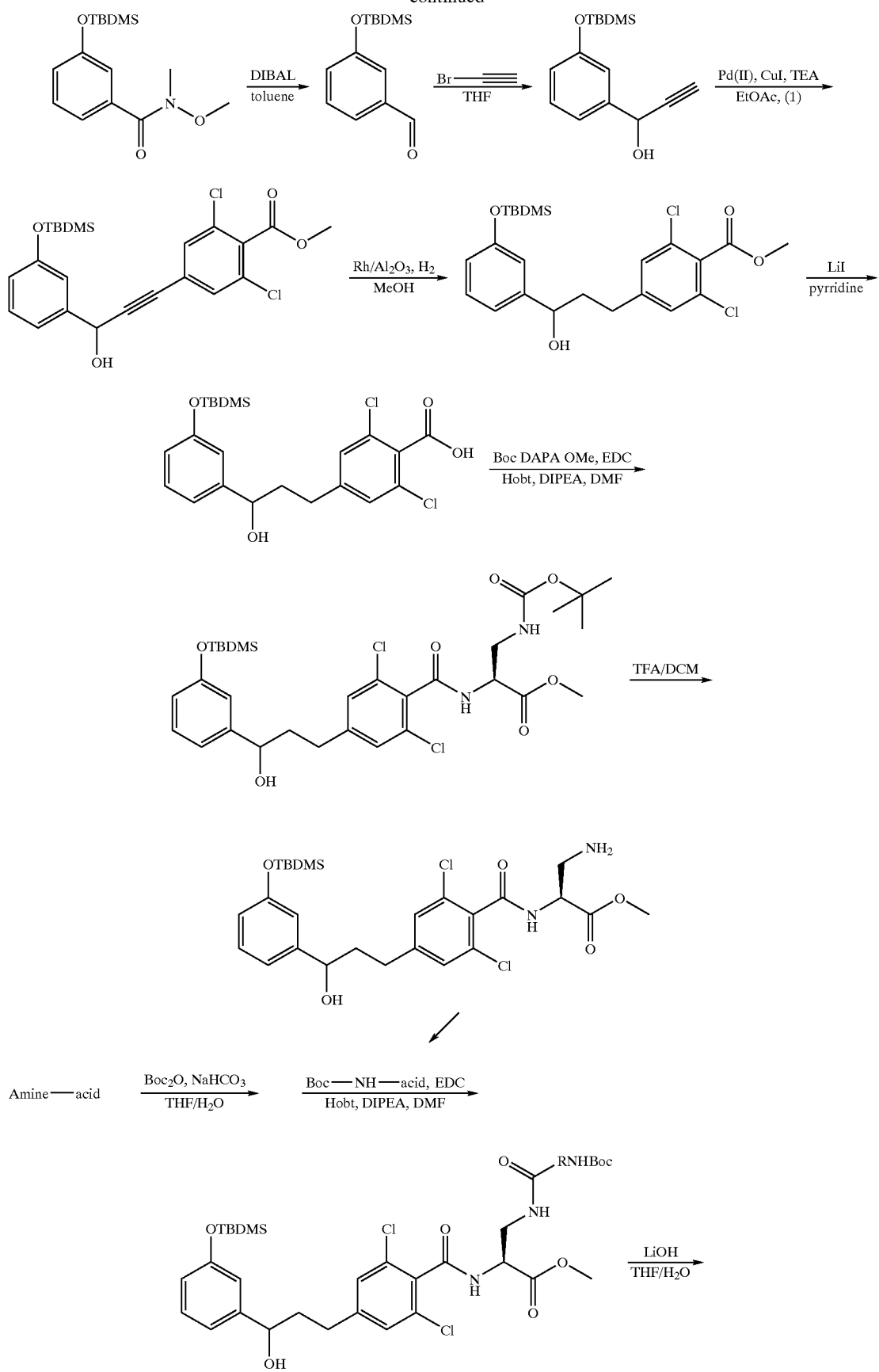

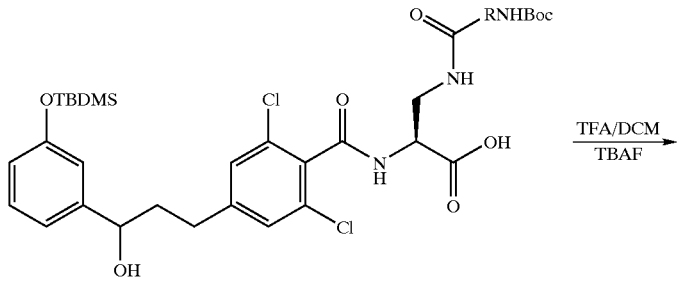

$\xrightarrow{\text{TFA/DCM}}_{\text{TBAF}}$

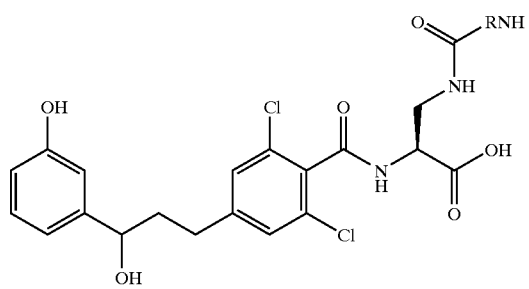

1 equivalent of 4-amino-2,6-dichlorophenol was dissolved in a 3:2 THF/H$_2$O solution. 1.1 equivalents of solid NaHCO$_3$ and 1.1 equivalents of Boc$_2$O were added and the solution was stirred overnight. The reaction was concentrated, and the residue was partitioned between H$_2$O and Et$_2$O. The aqueous layer was extracted with Et$_2$O and the combined organic layers were dried over MgSO$_4$ and concentrated in vacuo to a solid. Recrystallization out of Et$_2$O/hexane provided pure product.

1 equivalent of the phenol was dissolved in DCM containing 2.6 equivalents of 2,6-lutidine and the mixture was cooled to −78° C. After adding 1.25 equivalents of triflic anhydride the stirring reaction was allowed to warm to room temperature overnight. The reaction was then concentrated, and the residue was partitioned between Et$_2$O and H$_2$O. The aqueous layer was extracted with Et$_2$O and the combined organic layers were dried over MgSO$_4$ and concentrated in vacuo. The residue was purified by silica gel flash chromatography (9:1 hexane/Et$_2$O) to provide the pure triflate.

To a stirring solution of 1 equivalent of the triflate in a 2/1 mixture of DMF/MeOH was added 0.15 equivalents of 1,3-bis(diphenylphosphino)-propane and 2.5 equivalents of TEA. Carbon monoxide gas was bubbled through this solution for 15 minutes, then 0.15 equivalents of Pd(OAc)2 was added and the reaction was stirred at 70° C. for 5–7 hours under an atmosphere of CO (using a balloon filled with CO). The reaction was then concentrated in vacuo, and the residue was partitioned between Et$_2$O and H$_2$O. The aqueous layer was extracted twice with Et$_2$O and the combined organic layers were dried over MgSO$_4$, filtered through a plug of silica gel and concentrated in vacuo. The residue was purified by silica gel flash chromatography. (9:1:0.02 hexane/DCM/Et$_2$O) to provide the pure methyl ester.

1 equivalent of the Boc-aniline was dissolved in methanol and the solution saturated with HCl. The reaction was heated at 50° C. for 3 h, then concentrated in vacuo. The pale yellow solid was heated in 35% H$_2$SO$_4$ until complete dissolution occurred. Upon cooling the mixture by the addition of ice H$_2$O the amine bisulfate precipitated. The reaction flask was cooled in an ice bath and the mixture stirred vigorously while 1.1 equivalents of sodium nitrite in H$_2$O was added drop wise. The reaction was stirred at 0° C. for another 1.5 hours. An aqueous solution of 10 equivalents of KI was added, followed immediately with 17 equivalents CuI. The reaction was stirred at room temperature for 14 hours, then extracted 3 times with Et$_2$O. The combined organic layers were washed with 1M NaHCO$_3$, brine, and dried over MgSO$_4$, then concentrated in vacuo. The residue was purified by silica gel flash chromatography (95:5 hexane/Et$_2$O) to provide the pure aryl iodide methyl ester.

1.3 equivalents of DIPEA was added to a heterogeneous mixture of 1 equivalent of 3-hydroxybenzoic acid, 1.3 equivalents of N, O-dimethylhydroxylamine hydrochloride, 1.3 equivalents of HOBt and 1.3 equivalents of EDC stirring in DMF. All solids eventually dissolved as the mixture was stirred at room temperature for 28 hours. After concentrating the mixture, the residue was partitioned between Et$_2$O and H$_2$O. The aqueous layer was extracted three times with Et$_2$O and the combined organic layers were dried over MgSO$_4$, and concentrated in vacuo. The residue was purified by silica gel flash chromatography (Et$_2$O) to provide the pure hydroxamate.

1 equivalent of the hydroxamate, 2.2 equivalents of t-butyldimethyl silyl chloride and 3 equivalents of imidizole were dissolved in DMF and stirred at room temperature. The reaction was monitored by TLC (9/1 DCM/MeOH). Upon reaction completion, the mixture was concentrated in vacuo. The resulting oil was re suspended in Et$_2$O and washed twice with saturated NaHCO$_3$, and once with brine. The organic layer was then dried over MgSO$_4$, filtered and concentrated in vacuo. The product was then used with out further purification.

To a stirred −78° C. solution of 1 equivalent of the protected hydroxamate in THF was added a solution of 1.2 equivalents of 1.5 M DIBAL in toluene drop wise. The reaction mixture was stirred for an additional 3 hours at −78° C. or until TLC showed clean formation of product, with only a trace of starting material. The reaction was quenched by adding to a separatory funnel containing Et$_2$O and 0.35M NaHSO$_4$. The layers were separated. The aqueous layer was extracted three times with ethyl ether. The combined organic layers were washed twice with 1N HCl, saturated aqueous NaHCO$_3$, and over MgSO$_4$, filtered through a plug of silica gel, and concentrated in vacuo. No further purification of the aldehyde was necessary.

A solution of 1 equivalent of the protected aldehyde in THF was cooled to −78° C. and 1.1 equivalents of 0.5M ethynylmagnesium bromide/THF was added. After stirring the reaction at room temperature for 3 hours, it was diluted with Et$_2$O and washed twice with 10% citric acid. The combined aqueous layers were back-extracted once with Et$_2$O. The combined organic layers were washed twice with saturated aqueous NaHCO$_3$, dried over MgSO$_4$ and concentrated in vacuo. The residue was purified by silica gel flash chromatography (4:1 to 3:2 hexane/Et$_2$O) to provide the pure alkyne.

1 equivalent of the aryl iodide methyl ester was dissolved in EtOAc and the solution was degassed by passing N2 through a pipette and into the solution for 10 minutes. 1.25 equivalents of the alkyne was added, followed by 0.02 equivalents of dichlorobis(triphenylphosphine)palladium (II), 0.04 equivalents of CuI and 5 equivalents TEA. The reaction was stirred for 14 hours, diluted with EtOAc, washed twice with 5% Na$_2$.EDTA, brine and then dried over MgSO$_4$ and concentrated in vacuo. The residue was purified by silica gel flash chromatography (gradient elution, using Et$_2$O to EtOAc) to provide the pure aryl alkyne.

1 equivalent of the aryl alkyne was dissolved in MeOH and the solution was degassed by passing N2 through a pipette and into the solution for 10 minutes. The 5% Rh/Al$_2$O$_3$ was added, one balloon-full of hydrogen was passed through the solution, and the reaction was stirred under an atmosphere of H$_2$ (using a balloon) for 7 hours, after which the reaction was filtered through a pad of celite and concentrated in vacuo. The residue was purified by silica gel flash chromatography (gradient elution, using Et$_2$O to EtOAc) to provide the pure product.

2.3 equivalents of lithium iodide was added to 1 equivalent of the methyl ester in pyridine, and the mixture heated at reflux for 8 hours. The reaction was concentrated in vacuo and the residue was partitioned between EtOAc and 1N HCl. The aqueous layer was extracted three times with EtOAc, and the combined organic layers were washed with 1M NaHCO$_3$, dried over MgSO$_4$ and concentrated in vacuo. The residue was dissolved in NMM and the solution concentrated in vacuo. The residue was taken up in DCM and then washed three times with 1N HCl. The organic layer was dried over MgSO$_4$ and concentrated in vacuo to provide the benzoic acid in high enough purity to be used without further purification.

1 equivalent of the acid, 2 equivalents of commercially available β-Boc-diaminopropionic acid methyl ester, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et$_2$O and washed twice with 0.1 N H$_2$SO$_4$, twice with saturated NaHCO$_3$, and once with brine. The organic layer was then dried over MgSO$_4$, filtered and concentrated in vacuo. The residue was then purified on silica get using 5% methanol in DCM as eluent to provide pure methyl ester.

The Boc protected amine was dissolved in a solution of TFA in DCM (1:1). After 20 minutes, the reaction was concentrated in vacuo. The resulting oil was dissolved in toluene and then reconcentrated in vacuo. 1 equivalent of this amine, 2 equivalents of the appropriate commercially available carboxylic acid ((N-Boc acids were purchased where available. Other acids were purchased as the free amine and Boc protected by the following procedure: The amine was dissolved in a 3:2 THF/H$_2$O solution. 1.1 equivalents of solid NaHCO$_3$ and 1.1 equivalents of Boc$_2$O were added and the mixture was stirred overnight. The reaction was concentrated to remove the THF, and the resulting aqueous layer was partitioned with hexanes. The aqueous layer was then acidified to pH 2 with 1N HCl and then partitioned twice with EtOAc. The combined organic layers were dried over MgSO$_4$ and concentrated in vacuo. The resulting product was used without further purification) example 22, N-Boc-L-proline; example 23, N-Boc-D-proline; example 24, Boc-L-thiazolidine-4-carboxylic acid; example 25, D-hydroxy proline; 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et$_2$O and washed twice with 0.1 N H$_2$SO$_4$, twice with saturated NaHCO$_3$, and once with brine. The organic layer was then dried over MgSO$_4$, filtered and concentrated in vacuo. The residue was then purified on silica get using 5% methanol in DCM as eluent to provide pure methyl ester.

1 equivalent of the resultant methyl ester was dissolved in THF/H$_2$O (3/1) and 3 equivalents of LiOH·H$_2$O was added. The reaction was monitored by TLC (9/1 DCM/MeOH). Upon completion, the mixture was acidified to pH 2 with 1M HCl and then concentrated in vacuo. The resulting solid was re suspended in Et$_2$O and washed twice with 0.1 M HCl and once with brine. The organic layer was then dried over MgSO$_4$, filtered and concentrated in vacuo. The Boc, silyl residue was dissolved in a solution of TFA in DCM (1:1) with 3 equivalents of TBAF. After 20 minutes, the reaction was concentrated in vacuo. The resulting oil was dissolved in toluene and then reconcentrated in vacuo. The resulting acid was then purified by reverse phase HPLC, verified by electrospray mass spectrometry and lyophilized to a powder.

Example 5

Synthesis of Compounds 26–28, 31

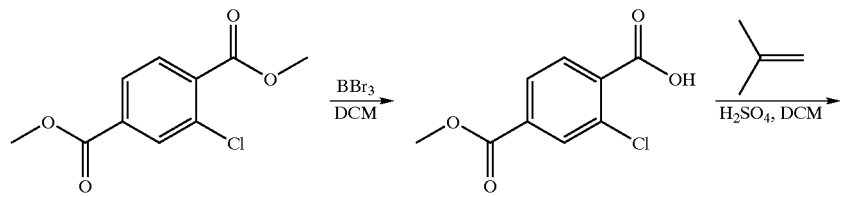

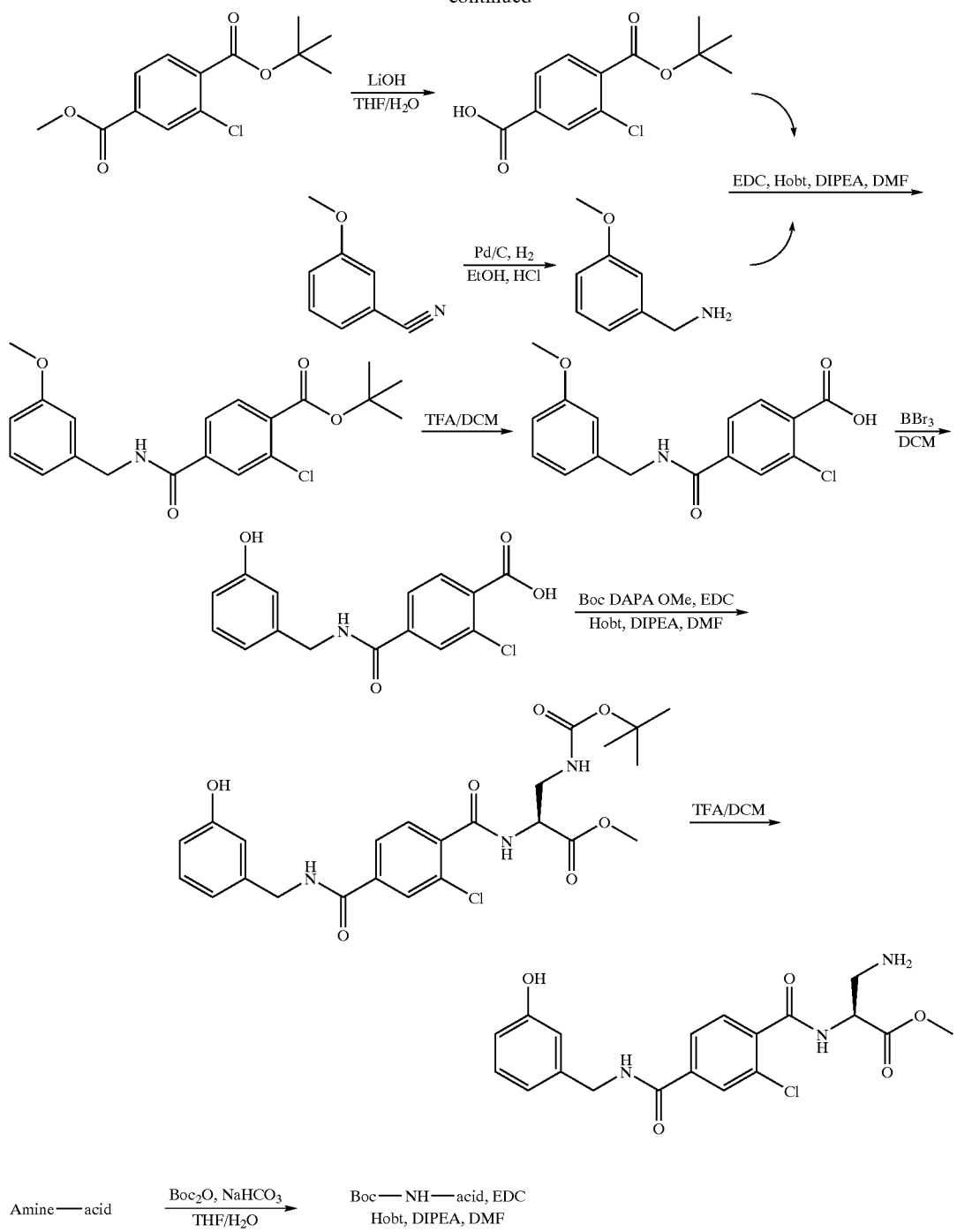
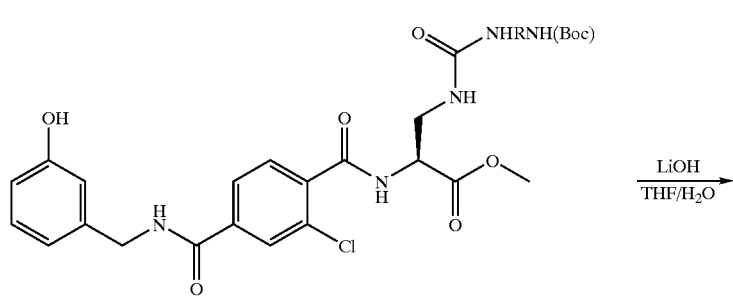

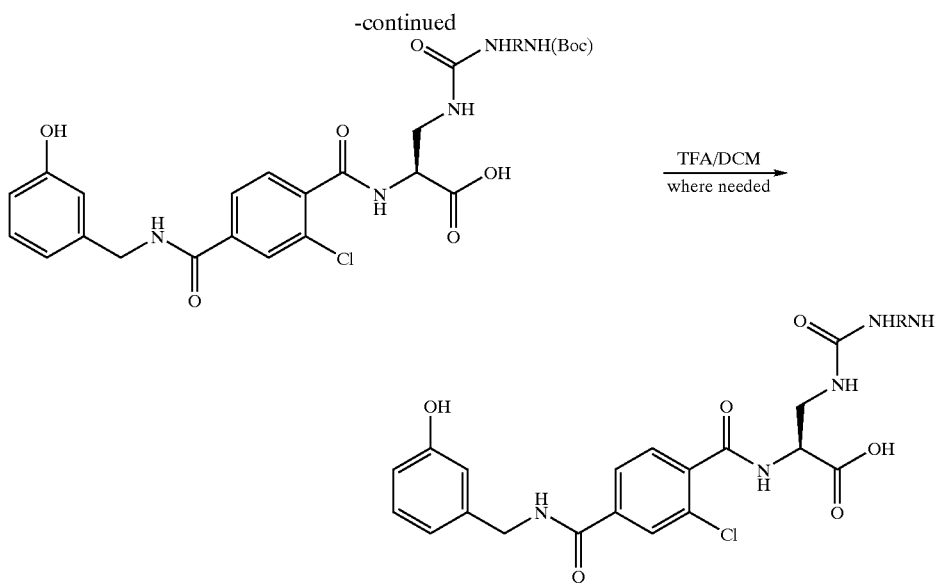

1 equivalent of dimethyl 2-chloroterephthalic acid was dissolved in DCM and cooled to −5° C. in an ice/acetone bath under nitrogen. 1 equivalent of BBr₃ was added drop wise as a solution in DCM over 30 minutes. The reaction was warmed to room temperature and stirred until complete by TLC (DCM/2% HOAc/2% MeOH). The solution was poured onto ice, and the ice was allowed to melt. The mixture was then partitioned with EtOAc and concentrated in vacuo. This product was dissolved in H₂O with the addition of saturated NaHCO₃ until the pH remained above 8. This solution was partitioned one time with and equal volume of DCM to remove unreacted diester. The basic solution was acidified at 0° C. with concentrated HCl to pH=1–1.5, and precipitate was extracted twice with equal volumes of EtOAc. The oraganics were partitioned once with brine and dried over MgSO₄, filtered and concentrated in vacuo. Product was 7:1 of the correct regioisomer by HPLC.

The monoester was dissolved in DCM and transferred to a pre-weighed Parr flask containing a stirring bar. The flask was cooled to −5° C. with a dry ice/alcohol bath under nitrogen. Once cool, ~30 equivalents of isobutylene was pumped into solution with stirring. 2.1 equivalents of concentrated sulfuric acid was added and the flask was sealed with a wired rubber stopper and allowed to warm to room temperature with stirring. The solution was stirred until clarification (1–2 days). Once the solution was clear, it was cooled to 0° C. in an ice bath. The stopper was removed and the excess isobutylene was blown off with nitrogen bubbling. Saturated NaHCO₃ was added to neutralize the acid and the mixture was concentrated in vacuo until no DCM remained. The solution was then partitioned into EtOAc. The oraganics were partitioned twice with dilute HCl, twice with saturated NaHCO₃, once with brine, dried over MgSO₄, filtered and concentrated in vacuo. The resulting product was used with no further purification.

1 equivalent of the methyl ester was dissolved in THF/H₂O (3/1) and 3 equivalents of LiOH·H₂O was added. The reaction was monitored by TLC (9/1 DCM/MeOH). Upon completion, the mixture was acidified carefully to pH 2 with concentrated HCl and then concentrated in vacuo to remove the THF. The resulting aqueous layer was washed twice with Et₂O and the combined organic layers were washed once with brine. The organic layer was then dried over MgSO₄, filtered and concentrated in vacuo. The benzoic acid t-butyl ester was used without further purification.

1 equivalent of 3-methoxybenzonitrile was placed in a Parr bottle with EtOH, 0.02 equivalents of HCl and 10% (w/w) of 10% Pd on carbon. The vessel was placed in the Parr shaker, charged with 50 psi H2, and shaken for 12 hours. The reaction filtered through a pad of celite and diluted 1:10 with Et₂O. Upon standing over night, fine white needles form. The product was filtered, washed with Et₂O and dried in vacuo. The resulting amine hydrochloride salt was then used with out further purification.

3 equivalents of the benzoic acid t-butyl ester was coupled to 1 equivalent of the amine hydrochloride salt using 3 equivalents EDC, 1 equivalent of Hobt and 3 equivalents of DIPEA in DMA. The reaction was monitored by TLC (9/1 DCM/MeOH). Upon completion, the mixture was concentrated in vacuo. The resulting oil was re suspended in Et₂O and washed twice with 0.1 N H₂SO₄, twice with saturated NaHCO₃, and once with brine. The organic layer was then dried over MgSO₄, filtered and concentrated in vacuo. The product was then purified on silica get using 5% methanol in DCM as eluent to provide pure t-butyl ester.

The t-butyl ester was dissolved in a solution of TFA in DCM (1:1). After 20 minutes, the reaction was concentrated in vacuo. The resulting oil was dissolved in toluene and then concentrated in vacuo twice.

The resulting compound was dissolved in DCM and cooled to −5° C. in an ice/acetone bath under nitrogen. 2 equivalents of BBr₃ were added drop wise as a solution in DCM over 30 minutes. The reaction was warmed to room temperature and stirred until complete by TLC (DCM/2% HOAc/2% MeOH). The solution was poured onto ice, and the ice was allowed to melt. The mixture was then partitioned twice with EtOAc and the combined organic layers were dried over MgSO₄. The filtrate was then passed over a plug of silica gel and concentrated in vacuo to afford pure benzoic acid.

1 equivalent of the benzoic acid, 2 equivalents of commercially available β-Boc-diaminopropionic acid methyl ester, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et$_2$O and washed twice with 0.1 N H$_2$SO$_4$, twice with saturated NaHCO$_3$, and once with brine. The organic layer was then dried over MgSO$_4$, filtered and concentrated in vacuo. The residue was then purified on silica gel using 5% methanol in DCM as eluent to provide pure methyl ester.

The Boc protected amine was dissolved in a solution of TFA in DCM (1:1). After 20 minutes, the reaction was concentrated in vacuo. The resulting oil was dissolved in toluene and then re concentrated in vacuo. 1 equivalent of this amine, 2 equivalents of the appropriate commercially available carboxylic acid ((N-Boc acids were purchased where available. Other acids were purchased as the free amine and Boc protected by the following procedure: The amine was dissolved in a 3:2 THF/H$_2$O solution. 1.1 equivalents of solid NaHCO$_3$ and 1.1 equivalents of Boc$_2$O were added and the mixture was stirred overnight. The reaction was concentrated to remove the THF, and the resulting aqueous layer was partitioned with hexanes. The aqueous layer was then acidified to pH 2 with 1N HCl and then partitioned twice with EtOAc. The combined organic layers were dried over MgSO$_4$ and concentrated in vacuo. The resulting product was used without further purification) example 26, cyclohexanecarboxylic acid; example 27, isonipecotic acid; example 28, D,L-pipecolinic acid; example 31, nipecotic acid; 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et$_2$O and washed twice with 0.1 N H$_2$SO$_4$, twice with saturated NaHCO$_3$, and once with brine. The organic layer was then dried over MgSO$_4$, filtered and concentrated in vacuo. The residue was then purified on silica gel using 5% methanol in DCM as eluent to provide pure methyl ester.

1 equivalent of the resultant methyl ester was dissolved in THF/H$_2$O (3/1) and 3 equivalents of LiOH·H$_2$O was added. The reaction was monitored by TLC (9/1 DCM/MeOH). Upon completion, the mixture was acidified to pH 2 with 1M HCl and then concentrated in vacuo. The resulting solid was re suspended in Et$_2$O and washed twice with 0.1 M HCl and once with brine. The organic layer was then dried over MgSO$_4$, filtered and concentrated in vacuo.

Where appropriate the Boc protected residue was dissolved in a solution of TFA in DCM (1:1). After 20 minutes, the reaction was concentrated in vacuo. The resulting oil was dissolved in toluene and then re concentrated in vacuo. The resulting acid was then purified by reverse phase HPLC, verified by electrospray mass spectrometry and lyophilized to a powder.

Example 6

Synthesis of Compounds 29, 30

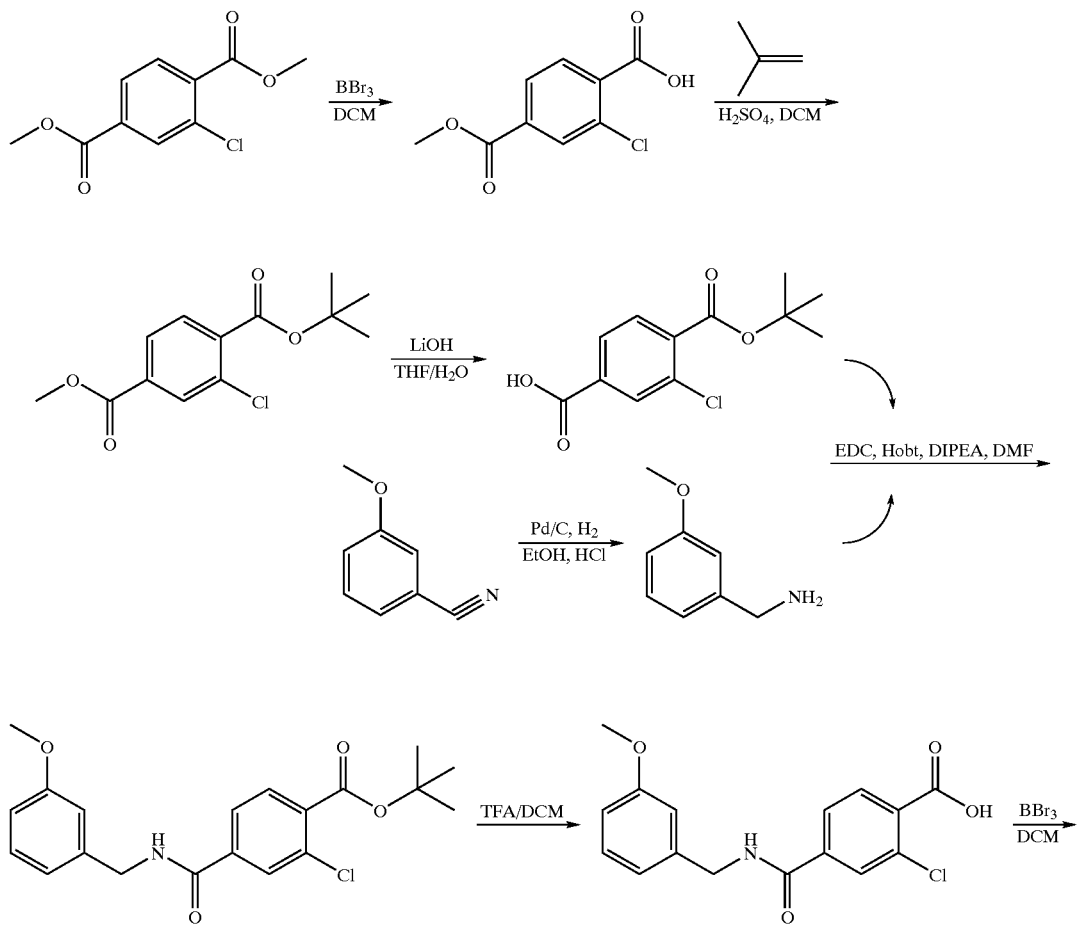

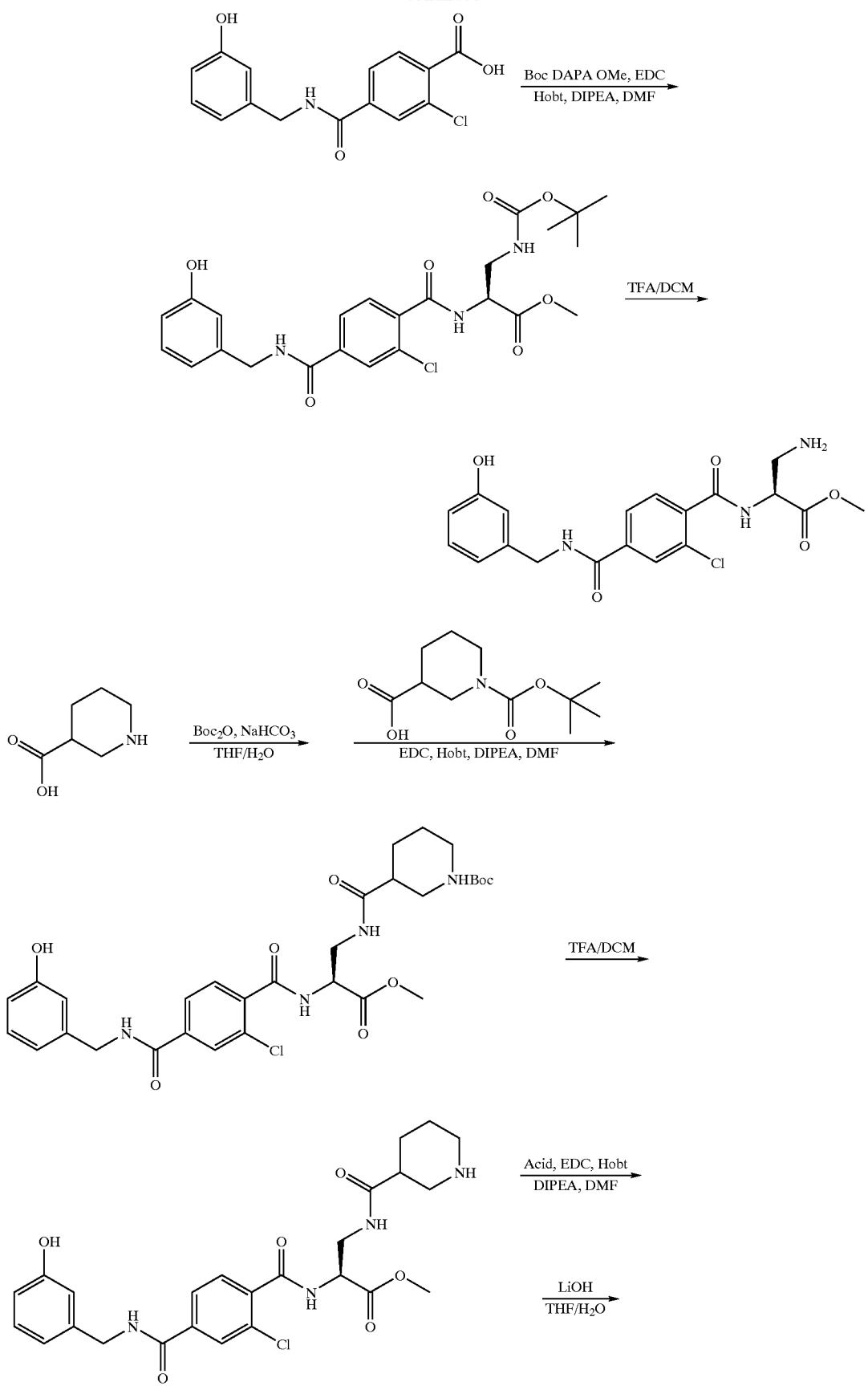

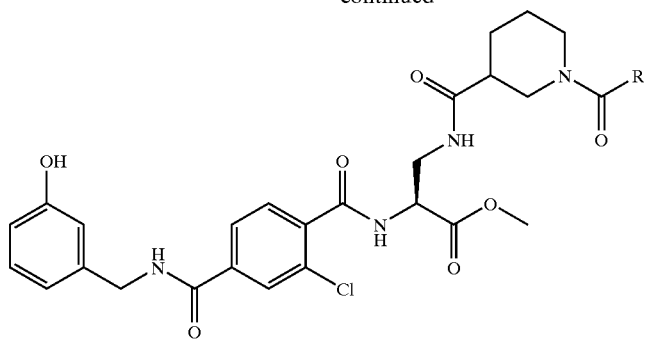

1 equivalent of dimethyl 2-chloroterephthalic acid was dissolved in DCM and cooled to −5° C. in an ice/acetone bath under nitrogen. 1 equivalent of BBr₃ was added drop wise as a solution in DCM over 30 minutes. The reaction was warmed to room temperature and stirred until complete by TLC (DCM/2% HOAc/2% MeOH). The solution was poured onto ice, and the ice was allowed to melt. The mixture was then partitioned with EtOAc and concentrated in vacuo. This product was dissolved in H₂O with the addition of saturated NaHCO₃ until the pH remained above 8. This solution was partitioned one time with and equal volume of DCM to remove unreacted diester. The basic solution was acidified at 0° C. with concentrated HCl to pH=1–1.5, and precipitate was extracted twice with equal volumes of EtOAc. The oraganics were partitioned once with brine and dried over MgSO₄, filtered and concentrated in vacuo. Product was 7:1 of the correct regioisomer by HPLC.

The monoester was dissolved in DCM and transferred to a pre-weighed Parr flask containing a stirring bar. The flask was cooled to −5° C. with a dry ice/alcohol bath under nitrogen. Once cool, ~30 equivalents of isobutylene was pumped into solution with stirring. 2.1 equivalents of concentrated sulfuric acid was added and the flask was sealed with a wired rubber stopper and allowed to warm to room temperature with stirring. The solution was stirred until clarification (1–2 days). Once the solution was clear, it was cooled to 0° C. in an ice bath. The stopper was removed and the excess isobutylene was blown off with nitrogen bubbling. Saturated NaHCO₃ was added to neutralize the acid and the mixture was concentrated in vacuo until no DCM remained. The solution was then partitioned into EtOAc. The oraganics were partitioned twice with dilute HCl, twice with saturated NaHCO₃, once with brine, dried over MgSO₄, filtered and concentrated in vacuo. The resulting product was used with no further purification.

1 equivalent of the methyl ester was dissolved in THF/H₂O (3/1) and 3 equivalents of LiOH·H₂O were added. The reaction was monitored by TLC (9/1 DCM/MeOH). Upon completion, the mixture was acidified carefully to pH 2 with concentrated HCl and then concentrated in vacuo to remove the THF. The resulting aqueous layer was washed twice with Et₂O and the combined organic layers were washed once with brine. The organic layer was then dried over MgSO₄, filtered and concentrated in vacuo. The benzoic acid t-butyl ester was used without further purification.

1 equivalent of 3-methoxybenzonitrile was placed in a Parr bottle with EtOH, 0.02 equivalents of HCl and 10% (w/w) of 10% Pd on carbon. The vessel was placed in the Parr shaker, charged with 50 psi H2, and shaken for 12 hours. The reaction filtered through a pad of celite and diluted 1:10 with Et₂O. Upon standing over night, fine white needles form. The product was filtered, washed with Et₂O and dried in vacuo. The resulting amine hydrochloride salt was then used with out further purification.

3 equivalents of the benzoic acid t-butyl ester was coupled to 1 equivalent of the amine hydrochloride salt using 3 equivalents EDC, 1 equivalent of Hobt and 3 equivalents of DIPEA in DMA. The reaction was monitored by TLC (9/1 DCM/MeOH). Upon completion, the mixture was concentrated in vacuo. The resulting oil was re suspended in Et₂O and washed twice with 0.1 N H₂SO₄, twice with saturated NaHCO₃, and once with brine. The organic layer was then dried over MgSO₄, filtered and concentrated in vacuo. The product was then purified on silica get using 5% methanol in DCM as eluent to provide pure t-butyl ester.

The t-butyl ester was dissolved in a solution of TFA in DCM (1:1). After 20 minutes, the reaction was concentrated in vacuo. The resulting oil was dissolved in toluene and then concentrated in vacuo twice.

The resulting compound was dissolved in DCM and cooled to −5° C. in an ice/acetone bath under nitrogen. 2 equivalents of BBr₃ were added drop wise as a solution in DCM over 30 minutes. The reaction was warmed to room temperature and stirred until complete by TLC (DCM/2% HOAc/2% MeOH). The solution was poured onto ice, and the ice was allowed to melt. The mixture was then partitioned twice with EtOAc and the combined organic layers were dried over MgSO₄. The filtrate was then passed over a plug of silica gel and concentrated in vacuo to afford pure benzoic acid.

1 equivalent of the benzoic acid, 2 equivalents of commercially available □-Boc-diaminopropionic acid methyl ester, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et₂O and washed twice with 0.1 N H₂SO₄, twice with saturated NaHCO₃, and once with brine. The organic layer was then dried over MgSO₄, filtered and concentrated in vacuo. The residue was then purified on silica get using 5% methanol in DCM as eluent to provide pure Boc methyl ester.

1 equivalent of commercially available nipecotic acid was dissolved in a 3:2 THF/H₂O solution. 1.1 equivalents of solid NaHCO₃ and 1.1 equivalents of Boc₂O were added and the mixture was stirred overnight. The reaction was concentrated to remove the THF, and the resulting aqueous layer was partitioned with hexanes. The aqueous layer was then acidified to pH 2 with 1N HCl and then partitioned twice with EtOAc. The combined organic layers were dried over MgSO$_4$ and concentrated in vacuo. The resulting Boc protected nipecotic acid was used without further purification.

The Boc methyl ester was dissolved in a solution of TFA in DCM (1:1). After 20 minutes, the reaction was concentrated in vacuo. The resulting oil was dissolved in toluene and then re concentrated in vacuo. 1 equivalent of this amine, 2 equivalents of resulting Boc protected nipecotic acid, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et$_2$O and washed twice with 0.1 N H$_2$SO$_4$, twice with saturated NaHCO$_3$, and once with brine. The organic layer was then dried over MgSO$_4$, filtered and concentrated in vacuo. The residue was then purified on silica get using 5% methanol in DCM as eluent to provide pure product.

This Boc protected product was dissolved in a solution of TFA in DCM (1:1). After 20 minutes, the reaction was concentrated in vacuo. The resulting oil was dissolved in toluene and then concentrated in vacuo twice to provide pure amine. 1 equivalent of this amine, 2 equivalents of the appropriate commercially available acid (example 29; propionic acid; example 30, acetic acid), 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et$_2$O and washed twice with 0.1 N H$_2$SO$_4$, twice with saturated NaHCO$_3$, and once with brine. The organic layer was then dried over MgSO$_4$, filtered and concentrated in vacuo. The residue was then purified on silica get using 5% methanol in DCM as eluent to provide pure product.

1 equivalent of the resultant methyl ester was dissolved in THF/H$_2$O (3/1) and 3 equivalents of LiOH·H$_2$O was added. The reaction was monitored by TLC (9/1 DCM/MeOH). Upon completion, the mixture was acidified to pH 2 with 1M HCl and then concentrated in vacuo. The resulting solid was re suspended in Et$_2$O and washed twice with 0.1 M HCl and once with brine. The organic layer was then dried over MgSO$_4$, filtered and concentrated in vacuo. The resulting acid was then purified by reverse phase HPLC, verified by electrospray mass spectrometry and lyophilized to a powder.

Example 7

Synthesis of Compounds 32–34

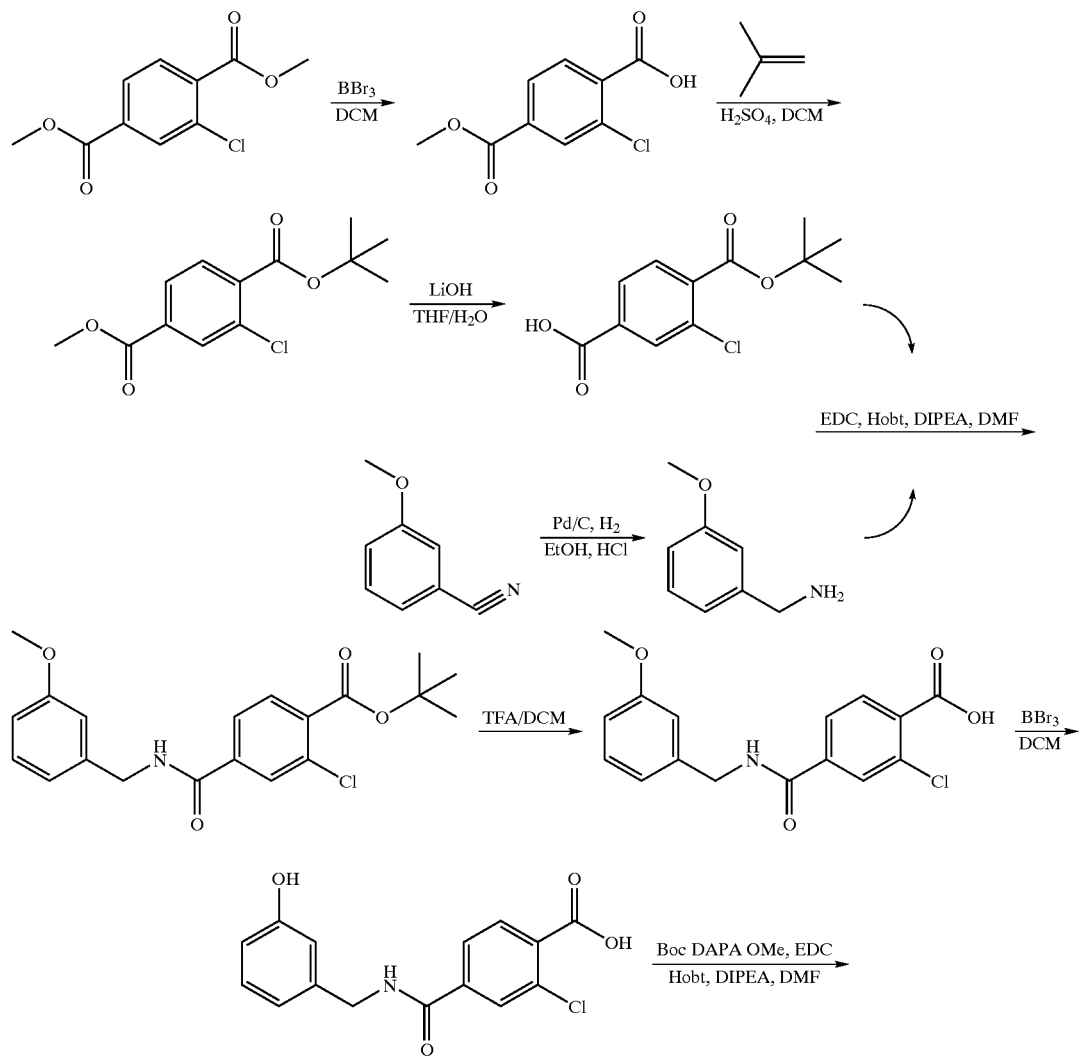

-continued
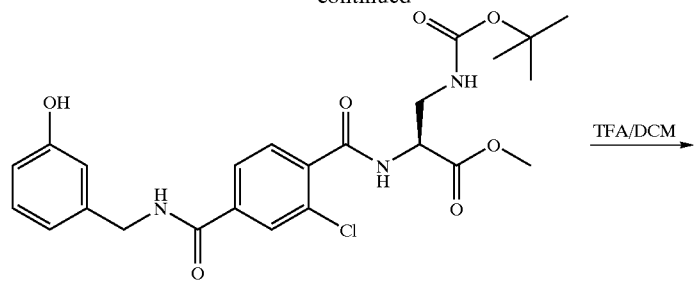
TFA/DCM →
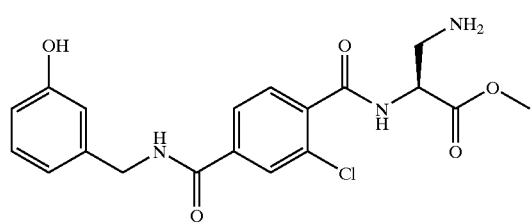
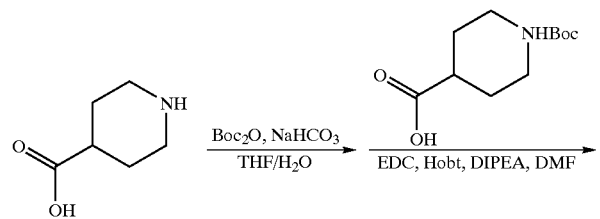
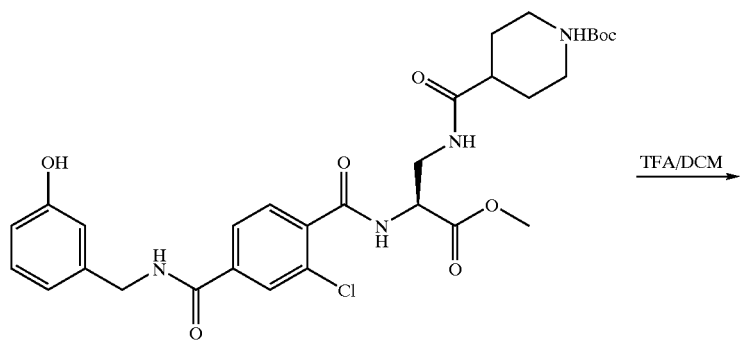
TFA/DCM →
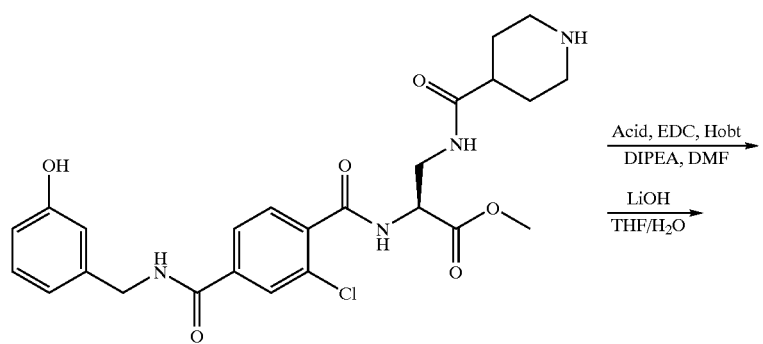
Acid, EDC, Hobt
DIPEA, DMF →
LiOH
THF/H₂O →

-continued

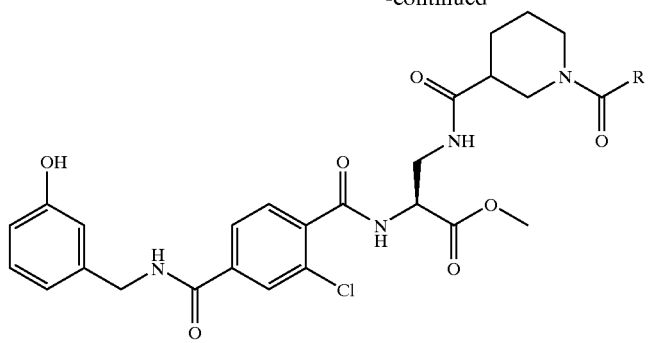

1 equivalent of dimethyl 2-chloroterephthalic acid was dissolved in DCM and cooled to −5° C. in an ice/acetone bath under nitrogen. 1 equivalent of BBr$_3$ was added drop wise as a solution in DCM over 30 minutes. The reaction was warmed to room temperature and stirred until complete by TLC (DCM/2% HOAc/2% MeOH). The solution was poured onto ice, and the ice was allowed to melt. The mixture was then partitioned with EtOAc and concentrated in vacuo. This product was dissolved in H$_2$O with the addition of saturated NaHCO$_3$ until the pH remained above 8. This solution was partitioned one time with and equal volume of DCM to remove unreacted diester. The basic solution was acidified at 0° C. with concentrated HCl to pH=1–1.5, and precipitate was extracted twice with equal volumes of EtOAc. The oraganics were partitioned once with brine and dried over MgSO$_4$, filtered and concentrated in vacuo. Product was 7:1 of the correct regioisomer by HPLC.

The monoester was dissolved in DCM and transferred to a pre-weighed Parr flask containing a stirring bar. The flask was cooled to −5° C. with a dry ice/alcohol bath under nitrogen. Once cool, ~30 equivalents of isobutylene was pumped into solution with stirring. 2.1 equivalents of concentrated sulfuric acid was added and the flask was sealed with a wired rubber stopper and allowed to warm to room temperature with stirring. The solution was stirred until clarification (1–2 days). Once the solution was clear, it was cooled to 0° C. in an ice bath. The stopper was removed and the excess isobutylene was blown off with nitrogen bubbling. Saturated NaHCO$_3$ was added to neutralize the acid and the mixture was concentrated in vacuo until no DCM remained. The solution was then partitioned into EtOAc. The oraganics were partitioned twice with dilute HCl, twice with saturated NaHCO$_3$, once with brine, dried over MgSO$_4$, filtered and concentrated in vacuo. The resulting product was used with no further purification.

1 equivalent of the methyl ester was dissolved in THF/H$_2$O (3/1) and 3 equivalents of LiOH·H$_2$O was added. The reaction was monitored by TLC (9/1 DCM/MeOH). Upon completion, the mixture was acidified carefully to pH 2 with concentrated HCl and then concentrated in vacuo to remove the THF. The resulting aqueous layer was washed twice with Et$_2$O and the combined organic layers were washed once with brine. The organic layer was then dried over MgSO$_4$, filtered and concentrated in vacuo. The benzoic acid t-butyl ester was used without further purification.

1 equivalent of 3-methoxybenzonitrile was placed in a Parr bottle with EtOH, 0.02 equivalents of HCl and 10% (w/w) of 10% Pd on carbon. The vessel was placed in the Parr shaker, charged with 50 psi H2, and shaken for 12 hours. The reaction filtered through a pad of celite and diluted 1:10 with Et$_2$O. Upon standing over night, fine white needles form. The product was filtered, washed with Et$_2$O and dried in vacuo. The resulting amine hydrochloride salt was then used with out further purification.

3 equivalents of the benzoic acid t-butyl ester was coupled to 1 equivalent of the amine hydrochloride salt using 3 equivalents EDC, 1 equivalent of Hobt and 3 equivalents of DIPEA in DMA. The reaction was monitored by TLC (9/1 DCM/MeOH). Upon completion, the mixture was concentrated in vacuo. The/resulting oil was re suspended in Et$_2$O and washed twice with 0.1 N H$_2$SO$_4$, twice with saturated NaHCO$_3$, and once with brine. The organic layer was then dried over MgSO$_4$, filtered and concentrated in vacuo. The product was then purified on silica get using 5% methanol in DCM as eluent to provide pure t-butyl ester.

The t-butyl ester was dissolved in a solution of TFA in DCM (1:1). After 20 minutes, the reaction was concentrated in vacuo. The resulting oil was dissolved in toluene and then concentrated in vacuo twice.

The resulting compound was dissolved in DCM and cooled to −5° C. in an ice/acetone bath under nitrogen. 2 equivalents of BBr$_3$ were added drop wise as a solution in DCM over 30 minutes. The reaction was warmed to room temperature and stirred until complete by TLC (DCM/2% HOAc/2% MeOH). The solution was poured onto ice, and the ice was allowed to melt. The mixture was then partitioned twice with EtOAc and the combined organic layers were dried over MgSO$_4$. The filtrate was then passed over a plug of silica gel and concentrated in vacuo to afford pure benzoic acid.

1 equivalent of the benzoic acid, 2 equivalents of commercially available □-Boc-diaminopropionic acid methyl ester, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et$_2$O and washed twice with 0.1 N H$_2$SO$_4$, twice with saturated NaHCO$_3$, and once with brine. The organic layer was then dried over MgSO$_4$, filtered and concentrated in vacuo. The residue was then purified on silica get using 5% methanol in DCM as eluent to provide pure Boc methyl ester.

1 equivalent of commercially available isonipecotic acid was dissolved in a 3:2 THF/H$_2$O solution. 1.1 equivalents of solid NaHCO$_3$ and 1.1 equivalents of Boc$_2$O were added and the mixture was stirred overnight. The reaction was concentrated to remove the THF, and the resulting aqueous layer was partitioned with hexanes. The aqueous layer was then acidified to pH 2 with 1N HCl and then partitioned twice with EtOAc. The combined organic layers were dried over MgSO₄ and concentrated in vacuo. The resulting Boc protected isonipecotic acid was used without further purification.

The Boc methyl ester was dissolved in a solution of TFA in DCM (1:1). After 20 minutes, the reaction was concentrated in vacuo. The resulting oil was dissolved in toluene and then re concentrated in vacuo. 1 equivalent of this amine, 2 equivalents of resulting Boc protected isonipecotic acid, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et₂O and washed twice with 0.1 N H₂SO₄, twice with saturated NaHCO₃, and once with brine. The organic layer was then dried over MgSO₄, filtered and concentrated in vacuo. The residue was then purified on silica get using 5% methanol in DCM as eluent to provide pure product.

This Boc protected product was dissolved in a solution of TFA in DCM (1:1). After 20 minutes, the reaction was concentrated in vacuo. The resulting oil was dissolved in toluene and then concentrated in vacuo twice to provide pure amine. 1 equivalent of this amine, 2 equivalents of the appropriate commercially available acid (example 32; propionic acid; example 33, butyric acid; example 34, acetic acid), 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et₂O and washed twice with 0.1 N H₂SO₄, twice with saturated NaHCO₃, and once with brine. The organic layer was then dried over MgSO₄, filtered and concentrated in vacuo. The residue was then purified on silica get using 5% methanol in DCM as eluent to provide pure product.

1 equivalent of the resultant methyl ester was dissolved in THF/H₂O (3/1) and 3 equivalents of LiOH·H₂O were added. The reaction was monitored by TLC (9/1 DCM/MeOH). Upon completion, the mixture was acidified to pH 2 with 1M HCl and then concentrated in vacuo. The resulting solid was re suspended in Et₂O and washed twice with 0.1 M HCl and once with brine. The organic layer was then dried over MgSO₄, filtered and concentrated in vacuo. The resulting acid was then purified by reverse phase HPLC, verified by electrospray mass spectrometry and lyophilized to a powder.

Example 8

Synthesis of Compounds 36

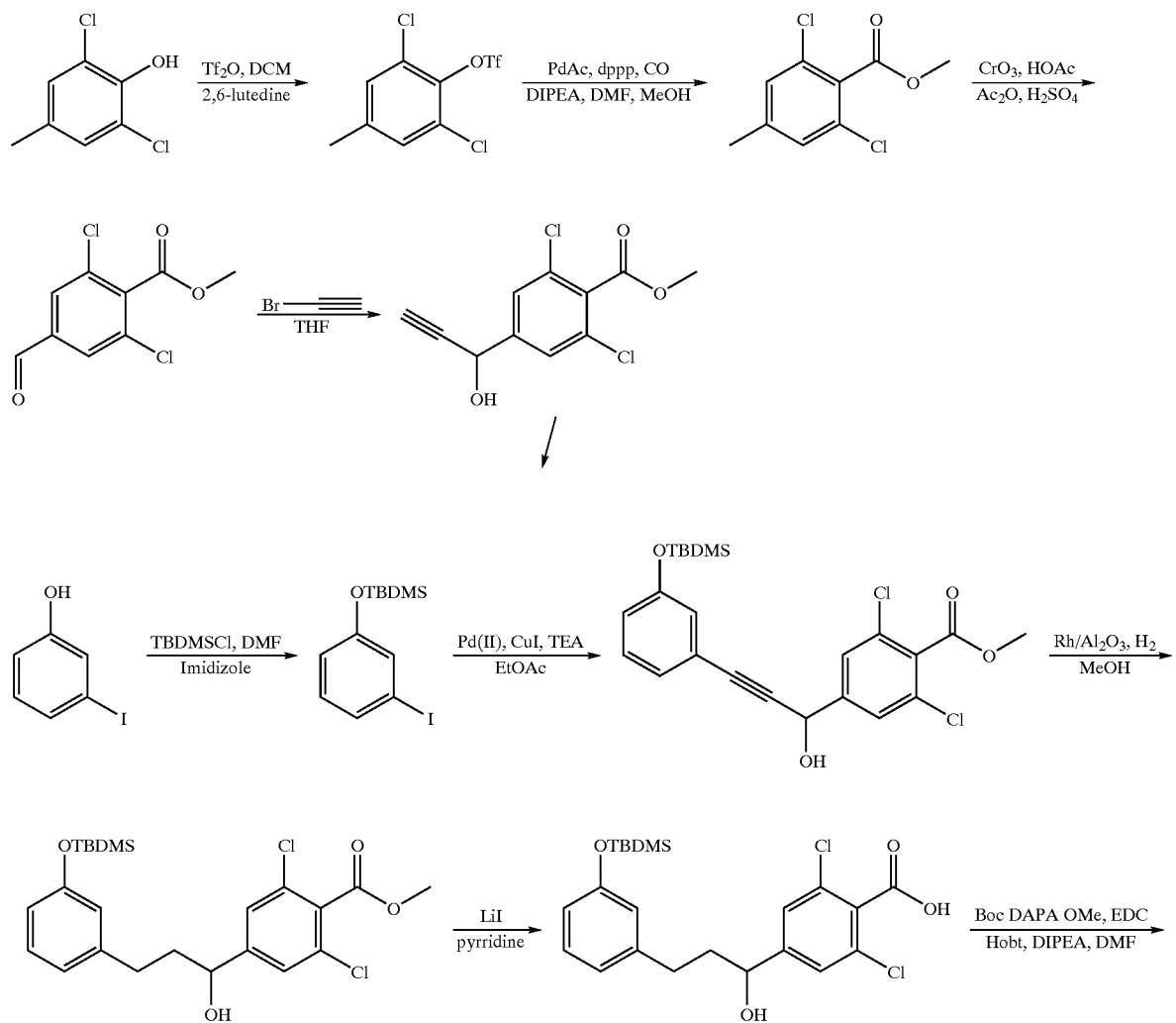

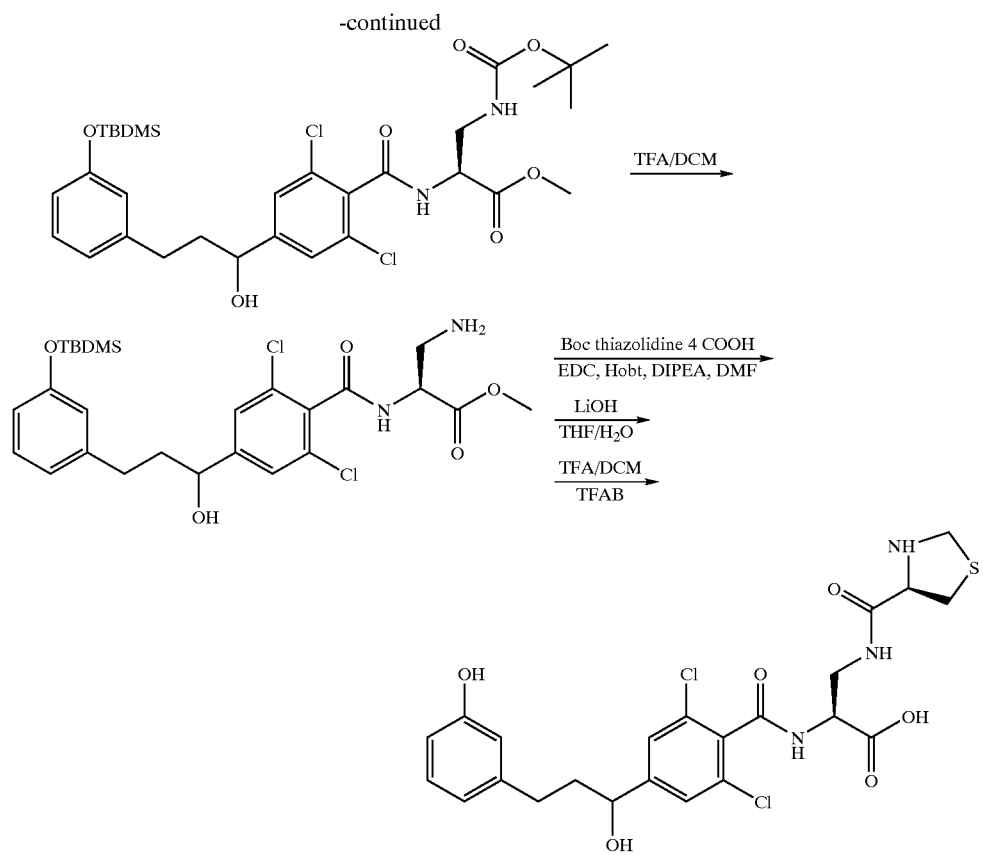

1 equivalent of 2,6-Dichloro-4-methyl phenol was dissolved in DCM containing 2.6 equivalents of 2,6-lutidine and the mixture was cooled to −78° C. After adding 1.25 equivalents of triflic anhydride the stirring reaction was allowed to warm to room temperature overnight. The reaction was then concentrated, and the residue was partitioned between Et$_2$O and H$_2$O. The aqueous layer was extracted with Et$_2$O and the combined organic layers were dried over MgSO$_4$ and concentrated in vacuo. The residue was purified by silica gel flash chromatography (9:1 hexane/Et$_2$O) to provide the pure triflate.

To a stirring solution of 1 equivalent of the triflate in a 2/1 mixture of DMF/MeOH was added 0.15 equivalents of 1,3-bis(diphenylphosphino)-propane and 2.5 equivalents of TEA. Carbon monoxide gas was bubbled through this solution for 15 minutes, then 0.15 equivalents of Pd(OAc)2 was added and the reaction was stirred at 70° C. for 5–7 hours under an atmosphere of CO (using a balloon filled with CO). The reaction was then concentrated in vacuo, and the residue was partitioned between Et$_2$O and H$_2$O. The aqueous layer was extracted twice with Et$_2$O and the combined organic layers were dried over MgSO$_4$, filtered through a plug of silica gel and concentrated in vacuo. The residue was purified by silica gel flash chromatography (9:1:0.02 hexane/DCM/Et$_2$O) to provide the pure tolyl methyl ester.

1 equivalent of the tolyl methyl ester was dissolved in acetic anhydride and HOAc, then cooled in an ice-salt bath (−5° C.) before concentrated H$_2$SO$_4$ was added. A solution of CrO$_3$ (2.6 equivalents) in acetic anhydride and HOAc was added drop wise and the reaction was stirred for 3.5 hours at −5° C. The reaction was poured into ice H$_2$O and stirred for 30 min. The mixture was extracted three times with ethyl ether. The combined organic layers were washed with saturated NaHCO$_3$ and brine, then dried over MgSO$_4$ and concentrated in vacuo to an oil. Toluene was added to the oil and the solution concentrated in vacuo again. This was repeated to obtain a crystalline solid. The solid was dissolved in methanol and concentrated HCl and heated at reflux for 12 hours. The reaction was concentrated in vacuo and the residue was purified by silica gel flash chromatography (9:1 hexane/Et$_2$O) to provide the pure aldehyde.

A solution of 1 equivalent of the aldehyde in THF was cooled to −78° C. and 1.1 equivalents of 0.5M ethynylmagnesium bromide/THF was added. After stirring the reaction at room temperature for 3 hours, it was diluted with Et$_2$O and washed twice with 10% citric acid. The combined aqueous layers were back-extracted once with Et$_2$O. The combined organic layers were washed twice with saturated aqueous NaHCO$_3$, dried over MgSO$_4$ and concentrated in vacuo. The residue was purified by silica gel flash chromatography (4:1 to 3:2 hexane/Et$_2$O) to provide the pure alkyne.

1 equivalent of 3-Iodophenol, 2.2 equivalents of t-butyldimethyl silyl chloride and 3 equivalents of imidizole were dissolved in DMF and stirred at room temperature. The reaction was monitored by TLC (9/1 DCM/MeOH). Upon reaction completion, the mixture was concentrated in vacuo. The resulting oil was re suspended in Et$_2$O and washed twice with saturated NaHCO$_3$, and once with brine. The organic layer was then dried over MgSO$_4$, filtered and concentrated in vacuo. The product was then used with out further purification.

1 equivalent of the silyl iodide was dissolved in EtOAc and the solution was degassed by passing N2 through a pipette and into the solution for 10 minutes. 1.25 equivalents of the alkyne was added, followed by 0.02 equivalents of dichlorobis(triphenylphosphine)-palladium(II), 0.04 equivalents of CuI and 5 equivalents TEA. The reaction was stirred for 14 hours, diluted with EtOAc, washed twice with 5% Na$_2$.EDTA, brine and then dried over MgSO$_4$ and concentrated in vacuo. The residue was purified by silica gel flash chromatography (gradient elution, using Et$_2$O to EtOAc) to provide the pure aryl alkyne.

1 equivalent of the aryl alkyne was dissolved in MeOH and the solution was degassed by passing N2 through a pipette and into the solution for 10 minutes. The 5% Rh/Al$_2$O$_3$ was added, one balloon-full of hydrogen was passed through the solution, and the reaction was stirred under an atmosphere of H$_2$ (using a balloon) for 7 hours, after which the reaction was filtered through a pad of celite and concentrated in vacuo. The residue was purified by silica gel flash chromatography (gradient elution, using Et$_2$O to EtOAc) to provide the pure product.

2.3 equivalents of lithium iodide was added to 1 equivalent of the methyl ester in pyridine, and the mixture heated at reflux for 8 hours. The reaction was concentrated in vacuo and the residue was partitioned between EtOAc and 1N HCl. The aqueous layer was extracted three times with EtOAc, and the combined organic layers were washed with 1M NaHCO$_3$, dried over MgSO$_4$ and concentrated in vacuo. The residue was dissolved in NMM and the solution concentrated in vacuo. The residue was taken up in DCM and then washed three times with 1N HCl. The organic layer was dried over MgSO$_4$ and concentrated in vacuo to provide the benzoic acid in high enough purity to be used without further purification.

1 equivalent of the acid, 2 equivalents of commercially available β-Boc-diaminopropionic acid methyl ester, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et$_2$O and washed twice with 0.1 N H$_2$SO$_4$, twice with saturated NaHCO$_3$, and once with brine. The organic layer was then dried over MgSO$_4$, filtered and concentrated in vacuo. The residue was then purified on silica get using 5% methanol in DCM as eluent to provide pure methyl ester.

The Boc protected amine was dissolved in a solution of TFA in DCM (1:1). After 20 minutes, the reaction was concentrated in vacuo. The resulting oil was dissolved in toluene and then reconcentrated in vacuo. 1 equivalent of this amine, 2 equivalents of Boc-L-thiazolidine-4-carboxylic acid, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in Et$_2$O and washed twice with 0.1 N H$_2$SO$_4$, twice with saturated NaHCO$_3$, and once with brine. The organic layer was then dried over MgSO$_4$, filtered and concentrated in vacuo. The residue was then purified on silica get using 5% methanol in DCM as eluent to provide pure methyl ester.

1 equivalent of the resultant methyl ester was dissolved in THF/H$_2$O (3/1) and 3 equivalents of LiOH·H$_2$O was added. The reaction was monitored by TLC (9/1 DCM/MeOH). Upon completion, the mixture was acidified to pH 2 with 1M HCl and then concentrated in vacuo. The resulting solid was re suspended in Et$_2$O and washed twice with 0.1 M HCl and once with brine. The organic layer was then dried over MgSO$_4$, filtered and concentrated in vacuo. The Boc, silyl residue was dissolved in a solution of TFA in DCM (1:1) with 3 equivalents of TBAF. After 20 minutes, the reaction was concentrated in vacuo. The resulting oil was dissolved in toluene and then reconcentrated in vacuo. The resulting acid was then purified by reverse phase HPLC, verified by electrospray mass spectrometry and lyophilized to a powder.

Example 9

Synthesis of Compounds 37

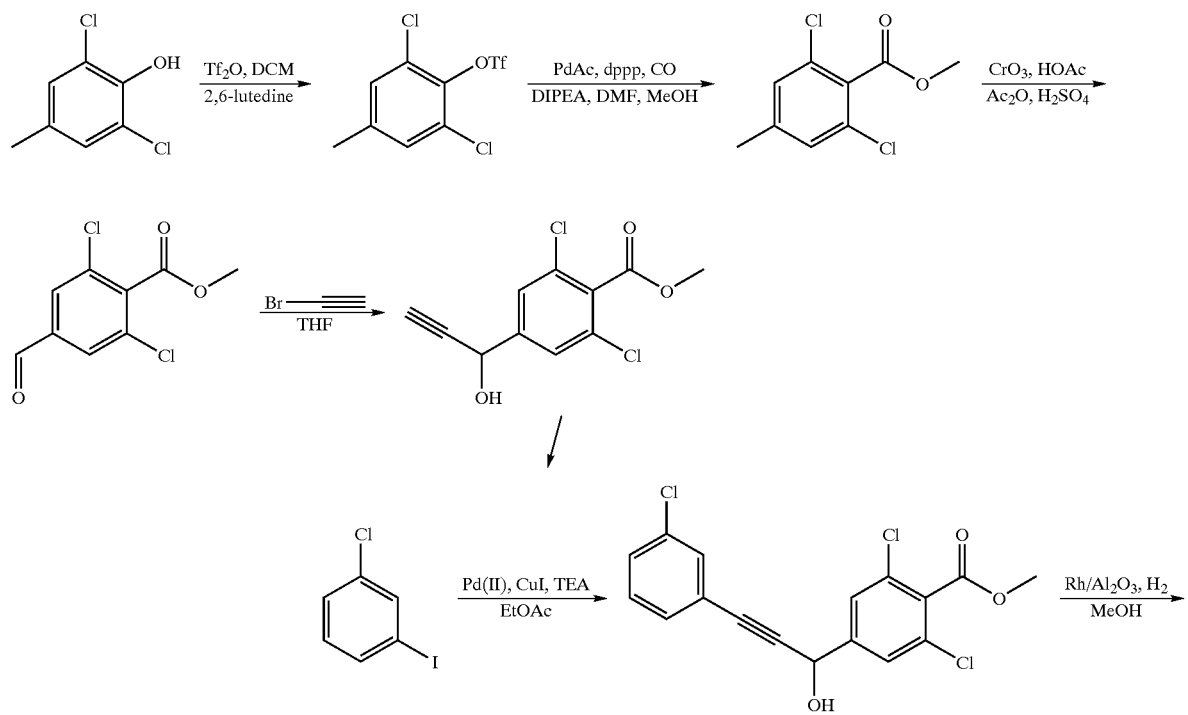

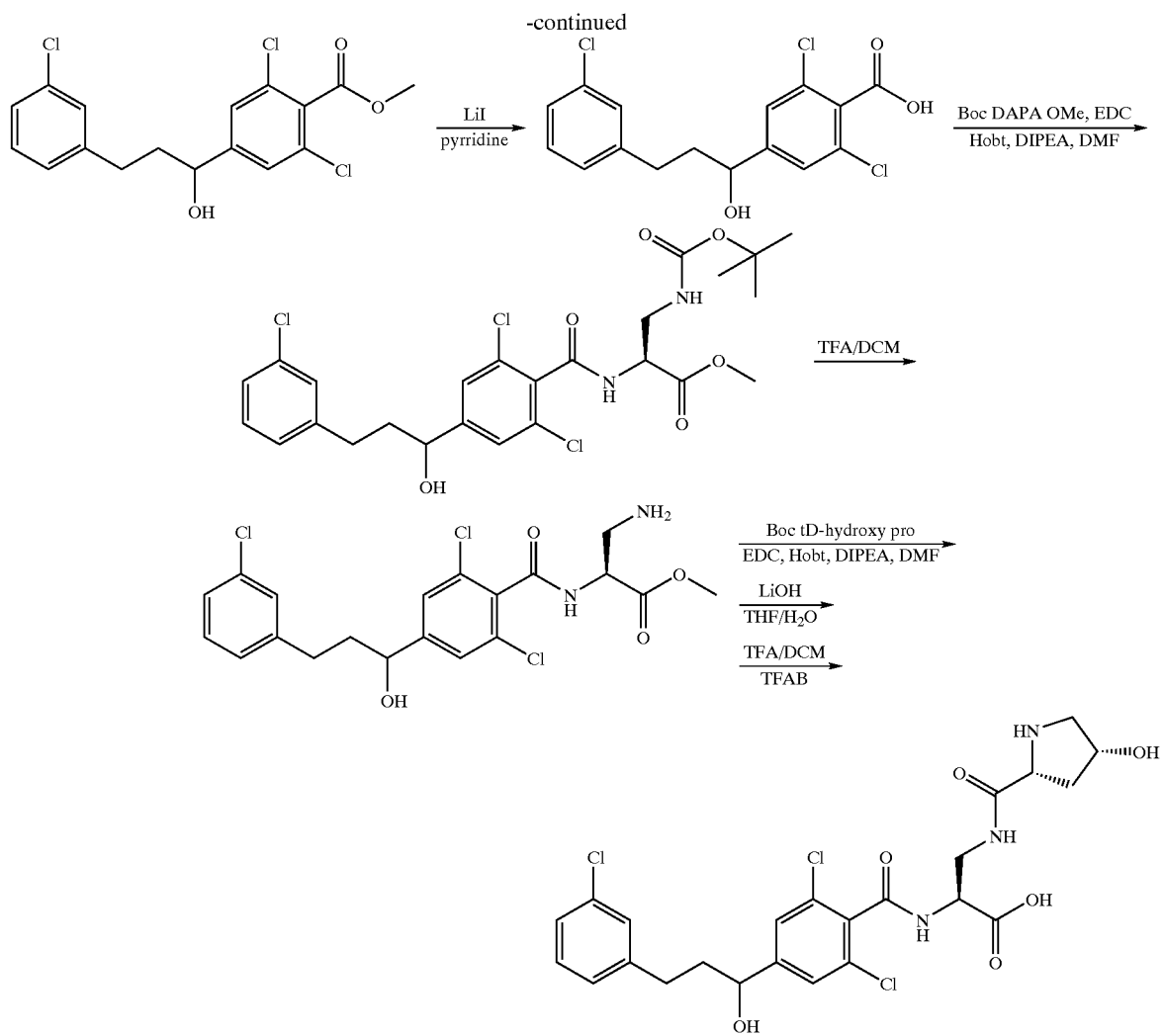

1 equivalent of 2,6-Dichloro-4-methyl phenol was dissolved in DCM containing 2.6 equivalents of 2,6-lutidine and the mixture was cooled to −78° C. After adding 1.25 equivalents of triflic anhydride the stirring reaction was allowed to warm to room temperature overnight. The reaction was then concentrated, and the residue was partitioned between $Et_2O$ and $H_2O$. The aqueous layer was extracted with $Et_2O$ and the combined organic layers were dried over $MgSO_4$ and concentrated in vacuo. The residue was purified by silica gel flash chromatography (9:1 hexane/$Et_2O$) to provide the pure triflate.

To a stirring solution of 1 equivalent of the triflate in a 2/1 mixture of DMF/MeOH was added 0.15 equivalents of 1,3-bis(diphenylphosphino)-propane and 2.5 equivalents of TEA. Carbon monoxide gas was bubbled through this solution for 15 minutes, then 0.15 equivalents of Pd(OAc)2 was added and the reaction was stirred at 70° C. for 5–7 hours under an atmosphere of CO (using a balloon filled with CO). The reaction was then concentrated in vacuo, and the residue was partitioned between $Et_2O$ and $H_2O$. The aqueous layer was extracted twice with $Et_2O$ and the combined organic layers were dried over $MgSO_4$, filtered through a plug of silica gel and concentrated in vacuo. The residue was purified by silica gel flash chromatography (9:1:0.02 hexane/DCM/$Et_2O$) to provide the pure tolyl methyl ester.

1 equivalent of the tolyl methyl ester was dissolved in acetic anhydride and HOAc, then cooled in an ice-salt bath (−5° C.) before concentrated $H_2SO_4$ was added. A solution of $CrO_3$ (2.6 equivalents) in acetic anhydride and HOAc was added drop wise and the reaction was stirred for 3.5 hours at −5° C. The reaction was poured into ice $H_2O$ and stirred for 30 min. The mixture was extracted three times with ethyl ether. The combined organic layers were washed with saturated $NaHCO_3$ and brine, then dried over $MgSO_4$ and concentrated in vacuo to an oil. Toluene was added to the oil and the solution concentrated in vacuo again. This was repeated to obtain a crystalline solid. The solid was dissolved in methanol and concentrated HCl and heated at reflux for 12 hours. The reaction was concentrated in vacuo and the residue was purified by silica gel flash chromatography (9:1 hexane/$Et_2O$) to provide the pure aldehyde.

A solution of 1 equivalent of the aldehyde in THF was cooled to −78° C. and 1.1 equivalents of 0.5M ethynylmagnesium bromide/THF was added. After stirring the reaction at room temperature for 3 hours, it was diluted with $Et_2O$ and washed twice with 10% citric acid. The combined aqueous layers were back-extracted once with $Et_2O$. The combined organic layers were washed twice with saturated aqueous $NaHCO_3$, dried over $MgSO_4$ and concentrated in vacuo. The residue was purified by silica gel flash chromatography (4:1 to 3:2 hexane/$Et_2O$) to provide the pure alkyne.

1 equivalent of 1-chloro-3-iodobenzene was dissolved in EtOAc and the solution was degassed by passing N2 through a pipette and into the solution for 10 minutes. 1.25 equivalents of the alkyne was added, followed by 0.02 equivalents of dichlorobis(triphenylphosphine)palladium(II), 0.04 equivalents of CuI and 5 equivalents TEA. The reaction was stirred for 14 hours, diluted with EtOAc, washed twice with 5% $Na_2.EDTA$, brine and then dried over $MgSO_4$ and concentrated in vacuo. The residue was purified by silica gel flash chromatography (gradient elution, using $Et_2O$ to EtOAc) to provide the pure aryl alkyne.

1 equivalent of the aryl alkyne was dissolved in MeOH and the solution was degassed by passing N2 through a pipette and into the solution for 10 minutes. The 5% $Rh/Al_2O_3$ was added, one balloon-full of hydrogen was passed through the solution, and the reaction was stirred under an atmosphere of $H_2$ (using a balloon) for 7 hours, after which the reaction was filtered through a pad of celite and concentrated in vacuo. The residue was purified by silica gel flash chromatography (gradient elution, using $Et_2O$ to EtOAc) to provide the pure product.

2.3 equivalents of lithium iodide was added to 1 equivalent of the methyl ester in pyridine, and the mixture heated at reflux for 8 hours. The reaction was concentrated in vacuo and the residue was partitioned between EtOAc and 1N HCl. The aqueous layer was extracted three times with EtOAc, and the combined organic layers were washed with 1M $NaHCO_3$, dried over $MgSO_4$ and concentrated in vacuo. The residue was dissolved in NMM and the solution concentrated in vacuo. The residue was taken up in DCM and then washed three times with 1N HCl. The organic layer was dried over $MgSO_4$ and concentrated in vacuo to provide the benzoic acid in high enough purity to be used without further purification.

1 equivalent of the acid, 2 equivalents of commercially available β-Boc-diaminopropionic acid methyl ester, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in $Et_2O$ and washed twice with 0.1 N $H_2SO_4$, twice with saturated $NaHCO_3$, and once with brine. The organic layer was then dried over $MgSO_4$, filtered and concentrated in vacuo. The residue was then purified on silica get using 5% methanol in DCM as eluent to provide pure methyl ester.

1 equivalent of commercially available D-hydroxy proline was dissolved in a 3:2 $THF/H_2O$ solution. 1.1 equivalents of solid $NaHCO_3$ and 1.1 equivalents of $Boc_2O$ were added and the mixture was stirred overnight. The reaction was concentrated to remove the THF, and the resulting aqueous layer was partitioned with hexanes. The aqueous layer was then acidified to pH 2 with 1N HCl and then partitioned twice with EtOAc. The combined organic layers were dried over $MgSO_4$ and concentrated in vacuo. The resulting N-Boc-D-hydroxy proline was used without further purification.

The Boc protected amine was dissolved in a solution of TFA in DCM (1:1). After 20 minutes, the reaction was concentrated in vacuo. The resulting oil was dissolved in toluene and then reconcentrated in vacuo. 1 equivalent of this amine, 2 equivalents of Boc-D-hydroxy proline, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in $Et_2O$ and washed twice with 0.1 N $H_2SO_4$, twice with saturated $NaHCO_3$, and once with brine. The organic layer was then dried over $MgSO_4$, filtered and concentrated in vacuo. The residue was then purified on silica get using 5% methanol in DCM as eluent to provide pure methyl ester.

1 equivalent of the resultant methyl ester was dissolved in $THF/H_2O$ (3/1) and 3 equivalents of $LiOH·H_2O$ was added. The reaction was monitored by TLC (9/1 DCM/MeOH). Upon completion, the mixture was acidified to pH 2 with 1M HCl and then concentrated in vacuo. The resulting solid was re suspended in $Et_2O$ and washed twice with 0.1 M HCl and once with brine. The organic layer was then dried over $MgSO_4$, filtered and concentrated in vacuo. The Boc, silyl residue was dissolved in a solution of TFA in DCM (1:1). After 20 minutes, the reaction was concentrated in vacuo. The resulting oil was dissolved in toluene and then reconcentrated in vacuo. The resulting acid was then purified by reverse phase HPLC, verified by electrospray mass spectrometry and lyophilized to a powder.

Example 10

Synthesis of Compound 35

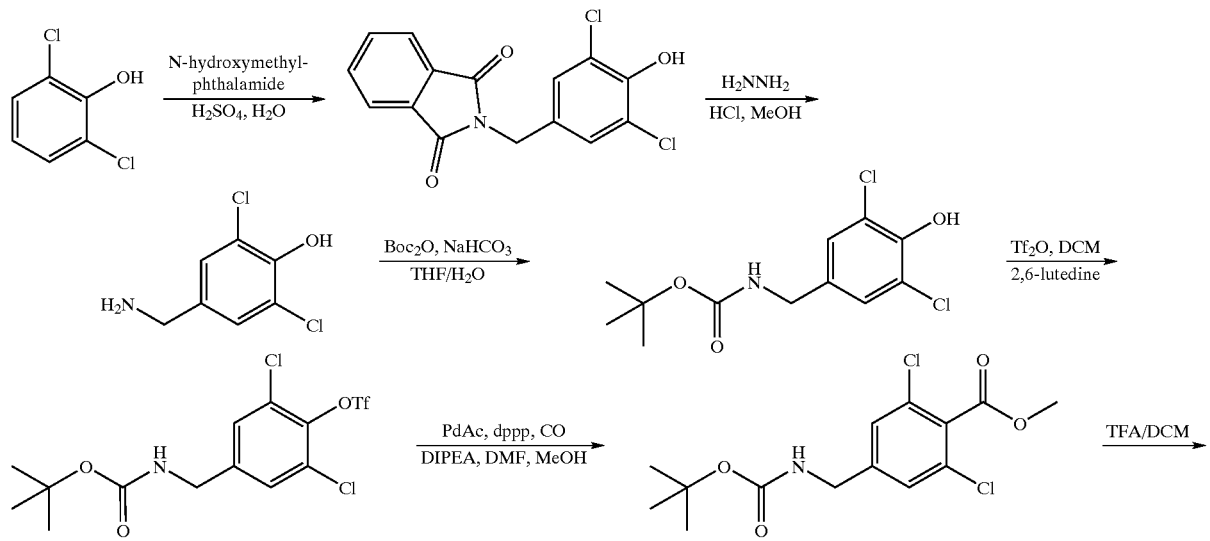

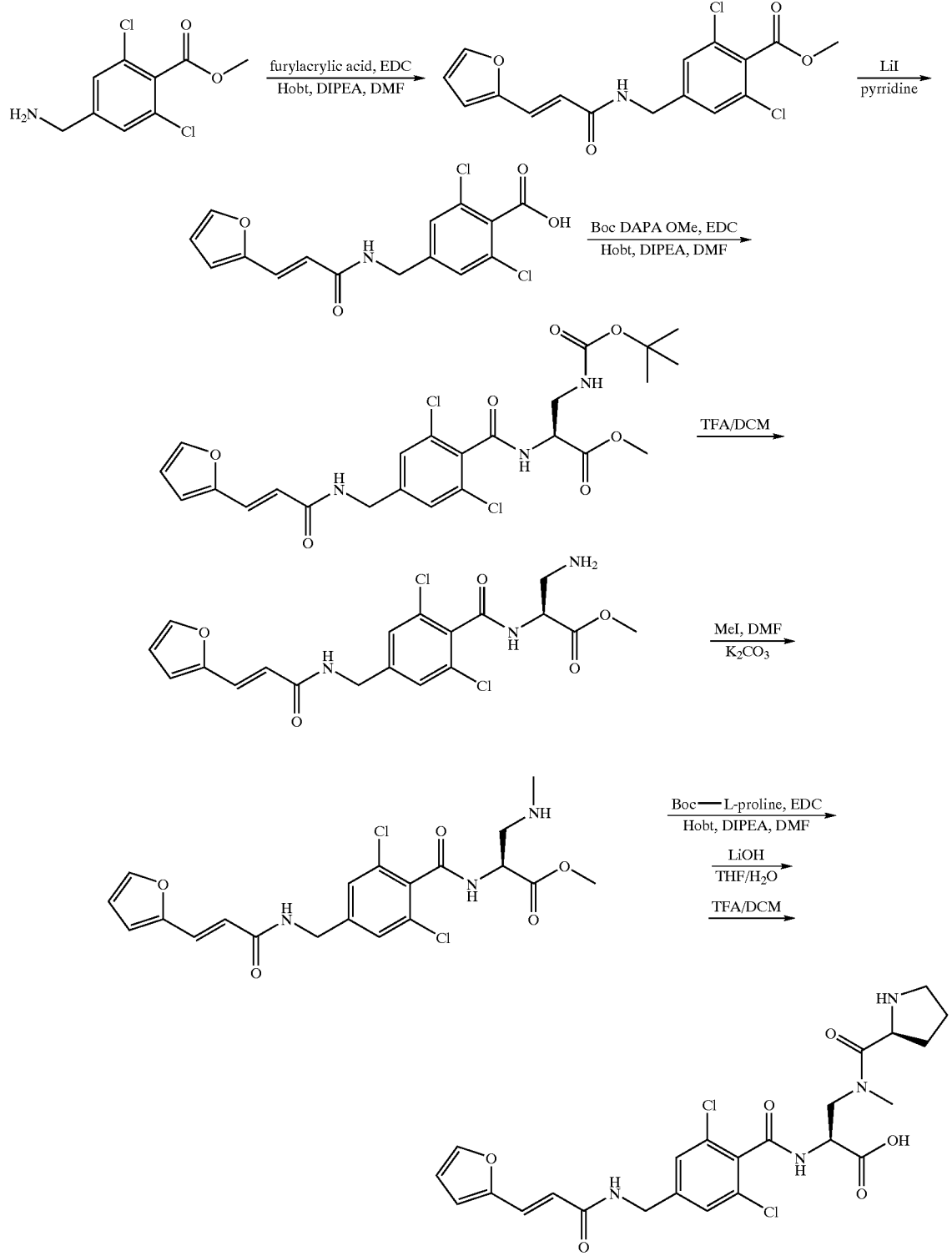

A round bottom flask was equipped with an efficient overhead stirrer and charged with concentrated $H_2SO_4$ (2.7× volume of $H_2O$) and $H_2O$ and cooled to ~−5° C. with an ethanol/ice bath. Once cool, 1 equivalent 2.6 dichloro phenol and 1 equivalent of N-(hydroxymethyl)phthalimide were added with vigorous stirring. The reaction was kept cool for 4 hours and then allowed to warm to room temperature overnight with constant stirring. The reaction generally proceeds to a point where there was just a solid in the round bottom flask. At this point EtOAc and $H_2O$ were added and stirred into the solid. Large chunks were broken up and then the precipitate was filtered and washed with more EtOAc and $H_2O$. The product was then used without further purification after drying overnight under vacuum.

1 equivalent of the dry product and methanol (22.5 ml×#g of starting material) was added to a round bottom flask equipped with a $H_2O$ condenser and stirring bar. 1.2 equivalents of hydrazine mono hydrate was added and the mixture refluxed for 4 hours. After cooling to room temperature, concentrated HCl (4.5 ml×#g of starting material) was carefully added. Upon completion of the addition, the mixture was refluxed overnight (>8 hours). The reaction was cooled to 0° C. and the precipitated by-product was removed by filtration. The filtrate was then concentrated in vacuo.

The crude amine residue was dissolved in a 3:2 THF/$H_2O$ solution. 1.1 equivalents of solid $NaHCO_3$ and 1.1 equivalents of $Boc_2O$ were added and the mixture was stirred overnight. The reaction was concentrated, and the residue was partitioned between $H_2O$ and $Et_2O$. The aqueous layer was extracted with $Et_2O$ and the combined organic layers were dried over $MgSO_4$ and concentrated in vacuo to a solid. Recrystallization from hot methanol and $H_2O$ provided pure product.

1 equivalent of the Boc protected amine and 1.5 equivalents of 2,6-lutidine was dissolved, with mild heating if necessary, in DCM in a round bottom flask. Once the starting material has completely dissolved, the mixture was cooled to −78° C. under $N_2$ with a dry ice ethanol bath. Once cool, 2.5 equivalents of triflic anhydride was added and the reaction was allowed to slowly come to room temperature with stirring. The reaction was monitored by TLC and was generally done in 4 hours. Upon completion, the reaction was concentrated in vacuo and the residue partitioned between EtOAc and $H_2O$. The organic layer was washed twice with 0.1N $H_2SO_4$, twice with saturated $NaHCO_3$, once with brine, dried over $MgSO_4$ and concentrated in vacuo. The residue was then purified on silica gel using DCM as eluent to provide pure triflate.

1 equivalent of triflate was dissolved in DMF and MeOH in the glass insert of a high pressure Parr bomb. The starting material was then degassed while stirring with CO for 10 minutes. 0.15 equivalents palladium(II) acetate and 0.15 equivalents of 1,3-bis(diphenylphosphino)propane were then added and the mixture was then degassed while stirring with CO for another 10 minutes at which time 2.5 equivalents of diisopropyl ethyl amine was added. After properly assembling the bomb, it was charged with 300 psi CO gas and heated to 70° C. with stirring overnight. The bomb was then cooled and vented. The mixture was transferred to a round bottom flask and concentrated in vacuo. The residue was then purified on silica gel using DCM with 1% acetone and 1% TEA as eluent to provide pure methyl ester.

The Boc protected amine was dissolved in a solution of TFA in DCM (1:1). After 20 minutes, the reaction was concentrated in vacuo. The resulting oil was dissolved in toluene and then reconcentrated in vacuo. The TFA salt of the amine was dissolved in $Et_2O$ and washed twice with a 10% solution of $K_2CO_3$ in $H_2O$ and once with brine. The organic layer was then dried over $MgSO_4$, filtered and concentrated in vacuo.

1 equivalent of the free based amine, 3 equivalents of furylacrylic acid, 3 equivalents of EDC and 1 equivalent of Hobt were dissolved DMA. The reaction was stirred at room temperature and monitored by TLC (9/1 DCM/MeOH). Upon completion, the mixture was concentrated in vacuo. The resulting oil was re suspended in $Et_2O$ and washed twice with 0.1 N $H_2SO_4$, twice with saturated $NaHCO_3$, and once with brine. The organic layer was then dried over $MgSO_4$, filtered and concentrated in vacuo. The residue was then purified on silica get using 5% methanol in DCM as eluent to provide pure methyl ester.

2.3 equivalents of lithium iodide was added to 1 equivalent of the methyl ester in pyridine, and the mixture heated at reflux for 8 hours. The reaction was concentrated in vacuo and the residue was partitioned between EtOAc and 1N HCl. The aqueous layer was extracted three times with EtOAc, and the combined organic layers were washed with 1M $NaHCO_3$, dried over $MgSO_4$ and concentrated in vacuo. The residue was dissolved in NMM and the solution concentrated in vacuo. The residue was taken up in DCM and then washed three times with 1N HCl. The organic layer was dried over $MgSO_4$ and concentrated in vacuo to provide the benzoic acid in high enough purity to be used without further purification.

1 equivalent of the acid, 2 equivalents of commercially available β-Boc-diaminopropionic acid methyl ester, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in $Et_2O$ and washed twice with 0.1 N $H_2SO_4$, twice with saturated $NaHCO_3$, and once with brine. The organic layer was then dried over $MgSO_4$, filtered and concentrated in vacuo. The residue was then purified on silica get using 5% methanol in DCM as eluent to provide pure methyl ester.

The Boc protected amine was dissolved in a solution of TFA in DCM (1:1). After 20 minutes, the reaction was concentrated in vacuo. The resulting oil was dissolved in toluene and then re concentrated in vacuo.

To 1 equivalent of this amine was added 1.05 equivalents of methyl iodide and 2.1 equivalents potassium carbonate in DMF. The reaction was stirred at room temperature and followed by TLC (9/1 DCM/MeOH). Upon completion of the reaction, it was diluted with EtOAc and $H_2O$. The aqueous layer was partitioned again with EtOAc and the combined organic layers washed with brine, dried over $MgSO_4$ and concentrated in vacuo.

1 equivalent of this amine, 2 equivalents of Boc-L-thiazolidine-4-carboxylic acid, 2 equivalents of EDC, 1 equivalent of Hobt and 3 equivalents of DIPEA were dissolved DMA. The reaction was stirred at room temperature and monitored by TLC (9/1 DCM/MeOH). Upon completion, the mixture was concentrated in vacuo. The resulting oil was re suspended in $Et_2O$ and washed twice with 0.1 N $H_2SO_4$, twice with saturated $NaHCO_3$, and once with brine. The organic layer was then dried over $MgSO_4$, filtered and concentrated in vacuo. The residue was then purified on silica get using 5% methanol in DCM as eluent to provide pure methyl ester.

1 equivalent of the resultant methyl ester was dissolved in THF/$H_2O$ (3/1) and 3 equivalents of LiOH·$H_2O$ was added. The reaction was monitored by TLC (9/1 DCM/MeOH). Upon completion, the mixture was acidified to pH 2 with 1M HCl and then concentrated in vacuo. The resulting solid was re suspended in $Et_2O$ and washed twice with 0.1 M HCl and once with brine. The organic layer was then dried over $MgSO_4$, filtered and concentrated in vacuo. The residue was dissolved in a solution of TFA in DCM (1:1). After 20 minutes, the reaction was concentrated in vacuo. The resulting oil was dissolved in toluene and then re concentrated in vacuo. The resulting acid was then purified by reverse phase HPLC, verified by electrospray mass spectrometry and lyophilized to a powder.

Example 11

PLM2 Antibody Capture LFA-1:ICAM-1 Assay

A non-function blocking monoclonal antibody against human CD18, PLM-2 (as described by Hildreth, et al., *Molecular Immunology*, Vol. 26, No. 9, pp. 883–895, 1989), is diluted to 5 µg/ml in PBS and 96-well flat-bottomed plates are coated with 100 µl/well overnight at 4° C. The plates are blocked with 0.5% BSA in assay buffer (0.02M Hepes, 0.15M NaCl, and 1 mM $MnCl_2$) 1 h at room temperature. Plates are washed with 50 mM Tris pH 7.5, 0.1M NaCl, 0.05% Tween 20 and 1 mM $MnCl_2$. Purified full-length recombinant human LFA-1 protein is diluted to 2 µg/ml in assay buffer and 100 µl/well is added to plates and incubated 1 h at 37° C. Plates are washed 3x. 50 µl/well inhibitors, appropriately diluted in assay buffer, are added to a 2x final concentration and incubated for 30' at 37° C. 50 µl/well of purified recombinant human 5 domain ICAM-Ig, diluted to 161 ng/ml (for a final concentration of 80 ng/ml) in assay buffer, is added and incubated 2 h at 37° C. Plates are washed and bound ICAM-Ig is detected with Goat anti-HuIgG(Fc)-HRP for 1 h at room temperature. Plates are washed and developed with 100 µl/well TMB substrate for 5–10' at room temperature. Colorimetric development is stopped with 100 µl/well 1M $H_3PO_4$ and read at 450 nM on a platereader. Results of the PLM2 assay are shown in tables 1–4 below.

Example 12

Serum/Plasma Protein Binding

Binding of test compounds was performed according to procedures described in Borga et al (Journal of Pharmacokinetics & Biopharmaceutics, 1997, 25(1):63–77) and Godolphin et al (Therapeutic drug monitoring, 1983, 5:319–23). Duplicate samples of 10 µl of test compound stock solution (1 µg/µL) was spiked into 1 mL of either buffer or serum/plasma adjusted to pH 7.4 using $CO_2$ at room temperature. Samples were equilibrated by incubating vials in a water bath with shaker at 37° C. for 15 minutes. 200 µl of the buffer spiked sample was saved as prefiltrate. 800 µl of buffer spiked samples and 1 ml of serum spiked samples were centrifuged at 1500 g, 37° C., for 30 minutes in a Centrifree ultrafiltration device (Amicon Inc.). Pre and post-filtrates were then analyzed by LC/MS-MS and percent binding of test compound to serum/plasma protein was determined from the post and prefiltrates accounting for any non-specific binding determined from the buffer control.

Compounds of the invention incorporating a non-aromatic ring at substituent Cy surprisingly exhibit low serum plasma protein binding characteristics which is advantageous for maintaining therapeutically relevant serum levels. As illustrated in tables 1–4, reference compounds (ref) having an aromatic ring at substituent Cy consistently show higher % plasma protein binding compared to the equivalent compound of the invention having a non-aromatic ring.

TABLE 1

| cmpd no. | LFA-1 PLM2 $IC_{50}$ (µM) | Mac-1 $IC_{50}$ (µM) | % plasma protein binding | structure |
| --- | --- | --- | --- | --- |
| ref | 0.071 | | 98.3 | 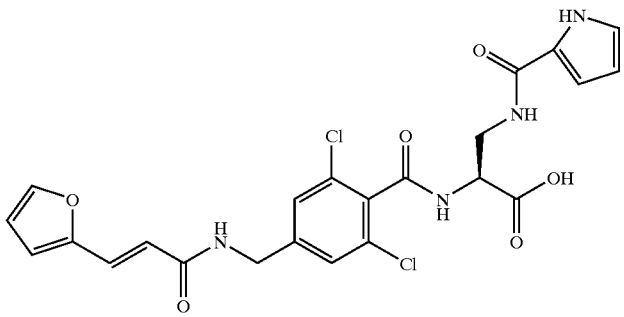 |
| 4 | 0.004 | | 82.9 | 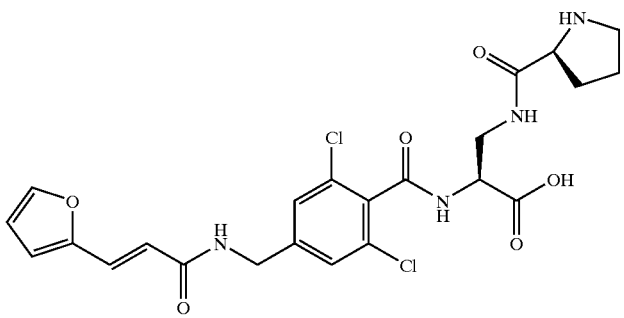 |

TABLE 1-continued

| cmpd no. | LFA-1 PLM2 IC$_{50}$ ($\mu$M) | Mac-1 IC$_{50}$ ($\mu$M) | % plasma protein binding | structure |
|---|---|---|---|---|
| 5 | 0.008 | | 83.1 | 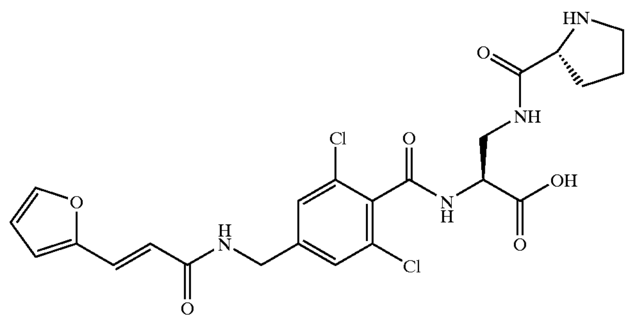 |
| 35 | 0.009 | | 51.36 | 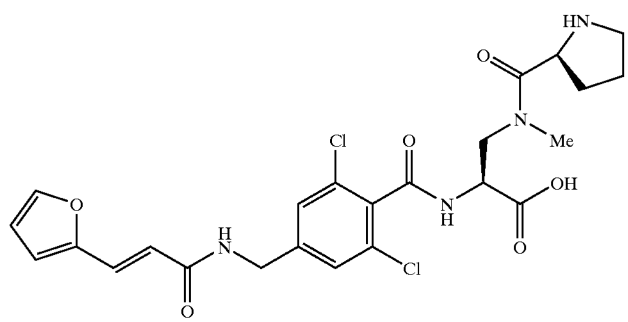 |
| 17 | 0.003 | | 84.61 | 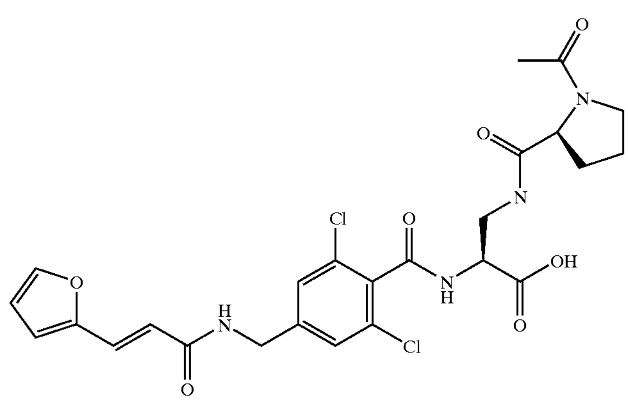 |
| 10 | 0.003 | | 65.91 | 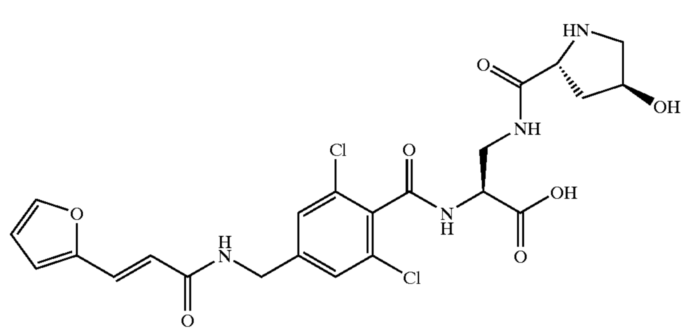 |

TABLE 1-continued

| cmpd no. | LFA-1 PLM2 IC$_{50}$ ($\mu$M) | Mac-1 IC$_{50}$ ($\mu$M) | % plasma protein binding | structure |
| --- | --- | --- | --- | --- |
| 12 | 0.002 | | 79.48 | 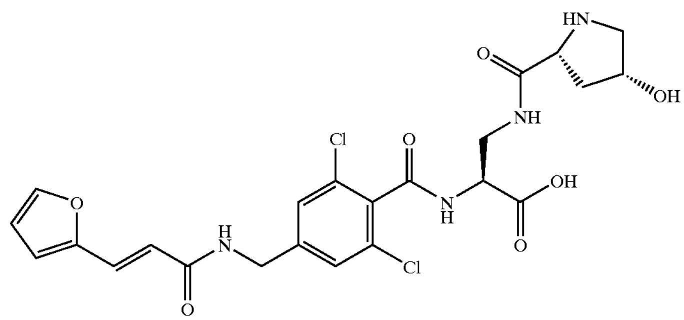 |
| 13 | 0.004 | | 77.58 | 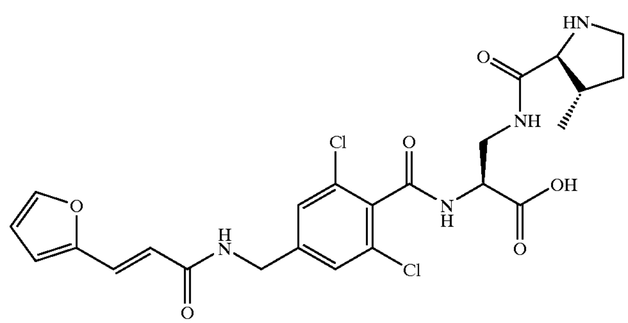 |
| 14 | 0.002 | | 72.60 | 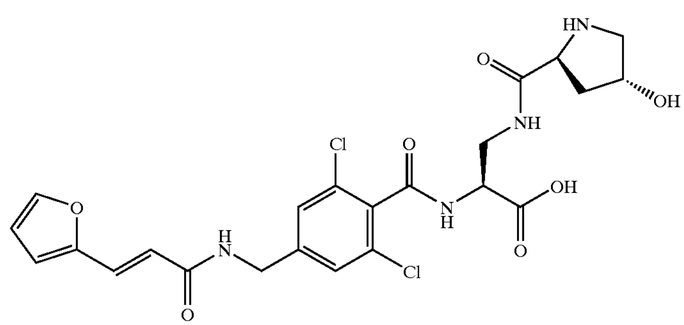 |
| 41 | 0.003 | | 84.83 | 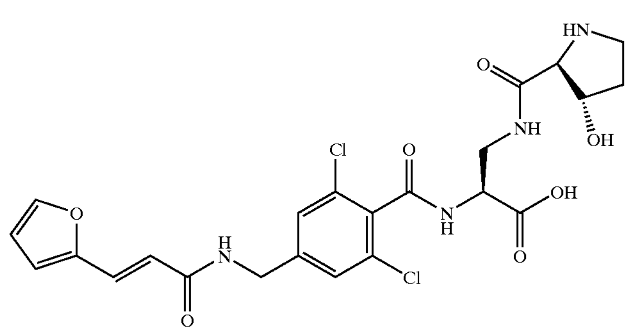 |

TABLE 1-continued

| cmpd no. | LFA-1 PLM2 IC$_{50}$ ($\mu$M) | Mac-1 IC$_{50}$ ($\mu$M) | % plasma protein binding | structure |
|---|---|---|---|---|
| 44 | 0.002 | | 82.97 | 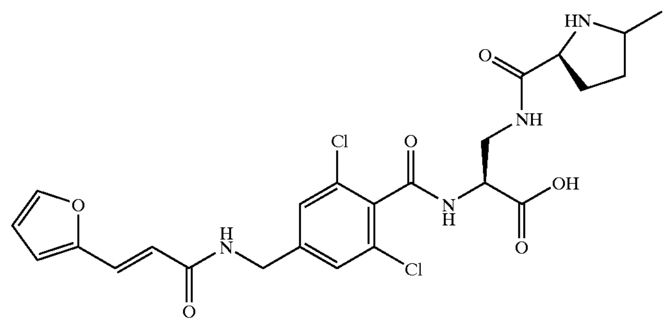 |

TABLE 2

| cmpd no. | LFA-1 PLM2 IC$_{50}$ ($\mu$M) | Mac-1 IC$_{50}$ ($\mu$M) | % plasma protein binding | structure |
|---|---|---|---|---|
| ref | 0.005 | | 98.12 | |
| ref | 0.004 | 161 | 99.5 | |
| 6 | 0.007 | 2509 | 95.43 | 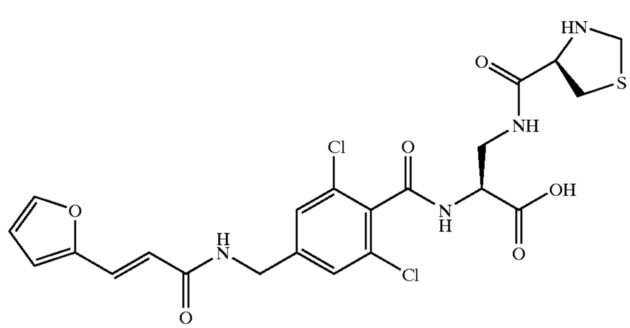 |

TABLE 2-continued

| cmpd no. | LFA-1 PLM2 IC$_{50}$ (μM) | Mac-1 IC$_{50}$ (μM) | % plasma protein binding | structure |
|---|---|---|---|---|
| 15 | 0.004 | | 92.51 | 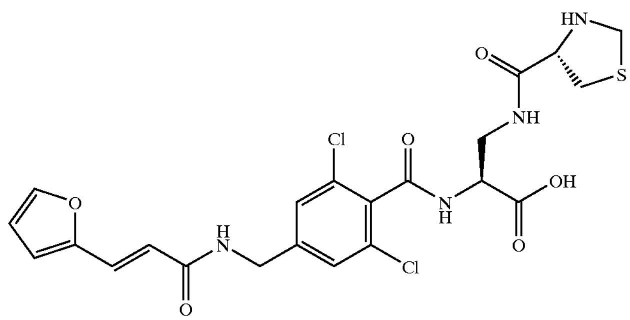 |
| 36 | 0.002 | 65 | 92.84 | 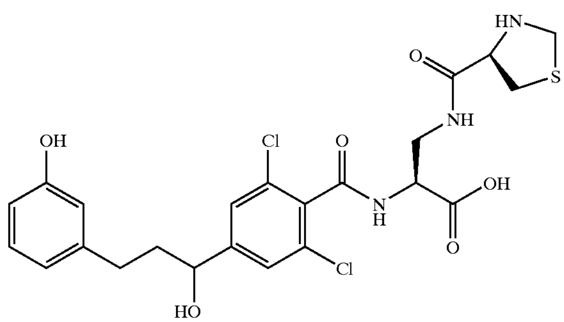 |
| 37 | | 35.54 | 93.19 | 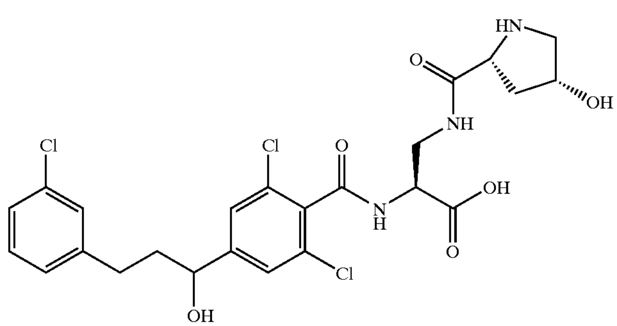 |
| 38 | 0.012 | 7609 | 93.29 | 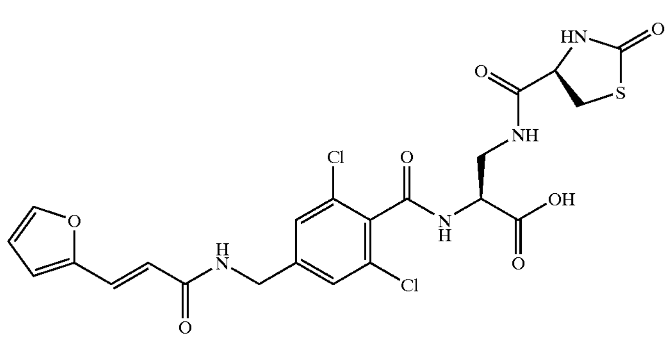 |

TABLE 2-continued

| cmpd no. | LFA-1 PLM2 IC$_{50}$ (μM) | Mac-1 IC$_{50}$ (μM) | % plasma protein binding | structure |
|---|---|---|---|---|
| 40 | 0.002 | 1427 | 96.93 | 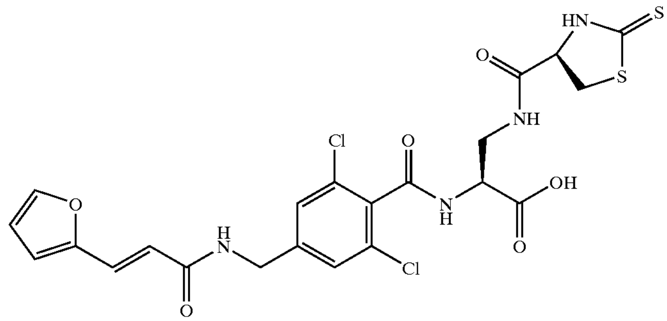 |
| 42 | 0.003 | | 91.4 | 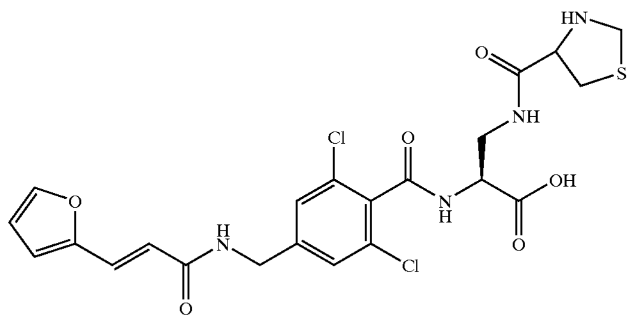 |

TABLE 3

| cmpd no. | LFA-1 PLM2 IC$_{50}$ (μM) | Mac-1 IC$_{50}$ (μM) | % plasma protein binding | structure |
|---|---|---|---|---|
| ref | 0.015 | | 99.4 | 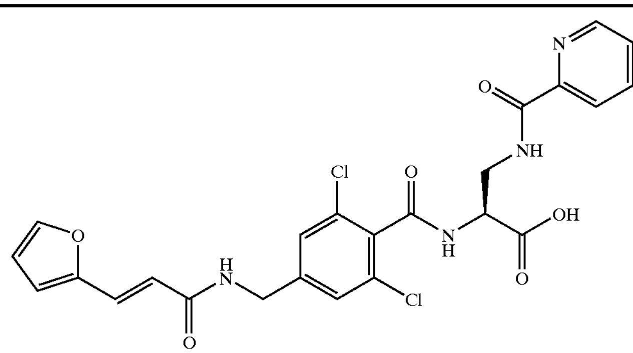 |
| 9 | 0.002 | | 77.17 | 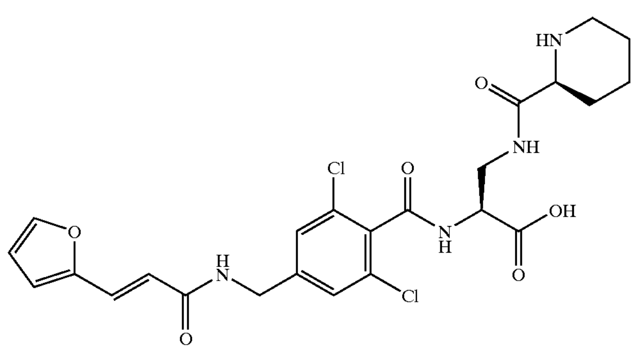 |

TABLE 3-continued

| cmpd no. | LFA-1 PLM2 IC$_{50}$ ($\mu$M) | Mac-1 IC$_{50}$ ($\mu$M) | % plasma protein binding | structure |
|---|---|---|---|---|
| 3 | 0.011 | | 80.8 | 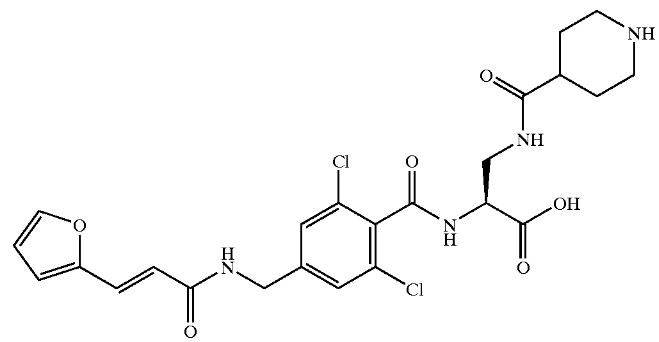 |

TABLE 4

| cmpd no. | LFA-1 PLM2 IC$_{50}$ ($\mu$M) | Mac-1 IC$_{50}$ ($\mu$M) | % plasma protein binding | structure |
|---|---|---|---|---|
| ref | | | 99.2 | |
| ref | 0.002 | 1683 | 99.70 | |
| 51 | 0.005 | 2362 | 92.8 | 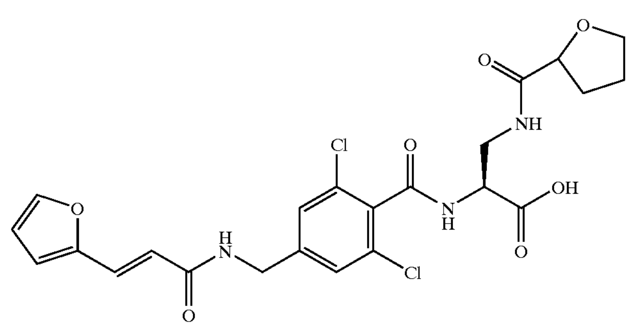 |

We claim:

1. A compound of formula (I)

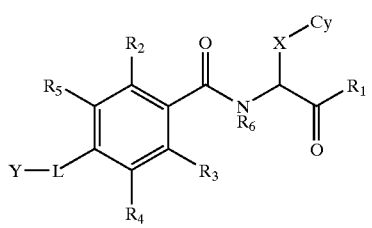

wherein
Cy is a non-aromatic heterocycle optionally substituted with hydroxyl, mercapto, thioalkyl, halogen, oxo, thio, amino, aminoalkyl, amidine, guanidine, nitro, alkyl, alkoxy or acyl;
X is —CH$_2$—NR$_6$—[divalent hydrocarbon chain]— wherein said divalent hydrocarbon chain is optionally substituted with hydroxyl, mercapto, halogen, amino, aminoalkyl, nitro, oxo or thio;
Y is a carbocycle or heterocycle optionally substituted with hydroxyl, mercapto, halogen, oxo, thio, thioalkyl, amino, aminoalkyl, carbocycle or heterocycle ring, hydrocarbon, a halo-substituted hydrocarbon, amino, amidine, guanidine, cyano, nitro, alkoxy or acyl;
L is a divalent hydrocarbon chain optionally substituted hydroxyl, halogen, oxo or thio
R$_1$ is H, OH, amino, O-carbocycle or alkoxy optionally substituted with amino, a carbocycle or heterocycle;
R$_{2-5}$ are independently H, hydroxyl, mercapto, halogen, cyano, amino, amidine, guanidine, nitro or alkoxy; or R$_3$ and R$_4$ together form a fused carbocycle or heterocycle optionally substituted with hydroxyl, halogen, oxo, thio, amino, amidine, guanidine or alkoxy;
R$_6$ is H or a hydrocarbon chain optionally substituted with a carbocycle or a heterocycle; and
salts, solvates and hydrates thereof.

2. A compound according to claim 1, wherein Cy is a 5- or 6-member non-aromatic heterocycle optionally substituted with hydroxyl, mercapto, thioalkyl halogen, oxo, thio, amino, aminoalkyl, amidine, guanidine, nitro, alkyl, alkoxy or acyl.

3. A compound according to claim 2, wherein said heterocycle comprises one or two heteroatoms and is optionally substituted with hydroxyl, oxo, mercapto, thio, alkyl or alkanoyl.

4. A compound according to claim 3, wherein said heterocycle is selected from the group consisting of piperidine, piperazine, morpholine, tetrahydrofuran, tetrahydrothiophene, oxazolidine, cyclopropa-pyrrolidine and thiazolidine optionally substituted with hydroxy, oxo, mercapto, thio, alkyl or alkanoyl.

5. A compound according to claim 4, wherein said heterocycle is selected from the group consisting of piperidine, piperazine, morpholine, tetrahydrofuran, tetrahydrothiophene, oxazolidine, thiazolidine optionally substituted with hydroxy, oxo, mercapto, thio, alkyl or alkanoyl.

6. A compound according to claim 1, wherein X is —CH$_2$—NR$_6$—C(O)— wherein the carbonyl —C(O)— portion thereof is covalently bound to Cy and R$_6$ is H or alkyl.

7. A compound according to claim 1, wherein Y is a carbocycle or heterocycle optionally substituted with hydroxyl or halogen.

8. A compound according to claim 7, wherein Y is furan-2-yl, thiophene-2-yl or phenyl, wherein said phenyl is optionally substituted with halogen or hydroxyl.

9. A compound according to claim 1, wherein L is —CH(OH)—(CH$_2$)$_2$—, —(CH$_2$)$_2$—CH(OH)—, —(CH$_2$)$_3$—, or —CH(OH)—CF$_2$—CH$_2$—.

10. A compound according to claim 9, wherein R$_1$ is H, OH, amino, O-carbocycle or alkoxy optionally substituted with a carbocycle.

11. A compound according to claim 10, wherein R$_1$ is H or C$_{1-4}$ alkyloxy.

12. A compound according to claim 1, wherein at least one of R$_2$ and R$_3$ is halogen and the other is H or halogen.

13. A compound according to claim 12, wherein R$_2$ and R$_3$ are both Cl.

14. A compound according to claim 13, wherein R$_4$ and R$_5$ are both H.

15. A pharmaceutical composition comprising a compound according to claim 1 with a pharmaceutically acceptable adjuvant, diluent or carrier.

16. A method of treating a disease or condition mediated by LFA-1 binding to an ICAM protein ligand in a mammal comprising administering to said mammal an effective amount of a compound according to claim 1 wherein said disease or condition is arthritis, psoriasis, organ transplant rejection, asthma, and inflammatory bowel disease.

17. A method of treating an inflammatory disease or condition in a mammal comprising administering to said mammal an effective amount of a compound according to claim 1 wherein said disease or condition is arthritis, psoriasis, organ transplant rejection, asthma, and inflammatory bowel disease.

18. The compound of claim 1 having the formula (Id)

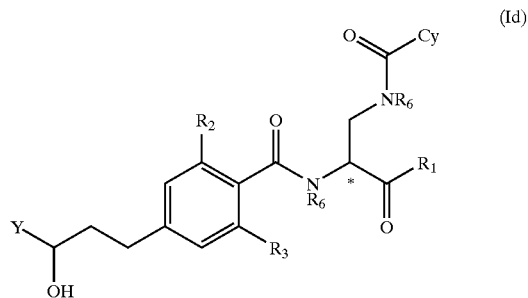

Cy is a non-aromatic heterocycle optionally substituted with hydroxyl, mercapto, thioalkyl, halogen, oxo, thio, amino, aminoalkyl, amidine, guanidine, nitro, alkyl, alkoxy or acyl;
Y is a carbocycle or heterocycle optionally substituted with hydroxyl, mercapto, halogen, oxo, thio, thioalkyl, amino, aminoalkyl, carbocycle or heterocycle ring, hydrocarbon, a halo-substituted hydrocarbon, amino, amidine, guanidine, cyano, nitro, alkoxy or acyl;
R$_1$ is H, OH, amino, O-carbocycle or alkoxy optionally substituted with amino, a carbocycle or heterocycle;
R$_2$ and R$_3$ are independently H, hydroxyl, mercapto, halogen, cyano, amino, amidine, guanidine, nitro or alkoxy;
R$_6$ is H or a hydrocarbon chain optionally substituted with a carbocycle or a heterocycle; and
salts, solvates and hydrates thereof.

19. The compound of claim 1 having the formula (Ie)

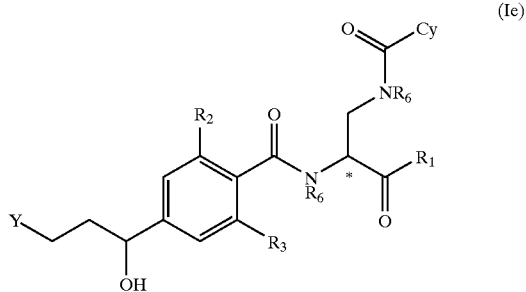

Cy is a non-aromatic heterocycle optionally substituted with hydroxyl, mercapto, thioalkyl, halogen, oxo, thio, amino, aminoalkyl, amidine, guanidine, nitro, alkyl, alkoxy or acyl;

Y is a carbocycle or heterocycle optionally substituted with hydroxyl, mercapto, halogen, oxo, thio, thioalkyl, amino, aminoalkyl, carbocycle or heterocycle ring, hydrocarbon, a halo-substituted hydrocarbon, amino, amidine, guanidine, cyano, nitro, alkoxy or acyl;

$R_1$ is H, OH, amino, O-carbocycle or alkoxy optionally substituted with amino, a carbocycle or heterocycle;

$R_2$ and $R_3$ are independently H, hydroxyl, mercapto, halogen, cyano, amino, amidine, guanidine, nitro or alkoxy;

$R_6$ is H or a hydrocarbon chain optionally substituted with a carbocycle or a heterocycle; and salts, solvates and hydrates thereof.

20. The compound of claim 18 wherein the chiral carbon marked with * has an S-configuration.

21. The compound of claim 19 wherein the chiral carbon marked with * has an S-configuration.

* * * * *